US007749366B2

(12) United States Patent
Quaiser et al.

(10) Patent No.: US 7,749,366 B2
(45) Date of Patent: Jul. 6, 2010

(54) ISOLATION AND CLONING OF DNA FROM UNCULTIVATED ORGANISMS

(75) Inventors: Achim Quaiser, Spaichingen (DE); Torsten Ochsenreiter, Woods Hole, MA (US); Alexander H. Treusch, Messel (DE); Arnulf Kletzin, Darmstadt (DE); Christa Schleper, Berjeu (NO); Patrick Lorenz, Lorsch (DE); Jürgen Eck, Heppenheim (DE)

(73) Assignee: B.R.A.I.N. Biotechnology Research and Information Network AG (DE)

( * ) Notice: Subject to any disclaimer, the term of this patent is extended or adjusted under 35 U.S.C. 154(b) by 363 days.

(21) Appl. No.: 10/525,708

(22) PCT Filed: Aug. 20, 2003

(86) PCT No.: PCT/EP03/09223

§ 371 (c)(1), (2), (4) Date: May 22, 2006

(87) PCT Pub. No.: WO2004/018673

PCT Pub. Date: Mar. 4, 2004

(65) Prior Publication Data

US 2006/0240423 A1 Oct. 26, 2006

(30) Foreign Application Priority Data

Aug. 20, 2002 (EP) ................................. 02018210

(51) Int. Cl.

*G01N 33/559* (2006.01)
*C40B 60/10* (2006.01)
*C12M 1/00* (2006.01)

(52) U.S. Cl. ....................... 204/456; 506/38; 435/287.2

(58) Field of Classification Search ................. 204/456; 506/38; 435/287.2

See application file for complete search history.

(56) References Cited

U.S. PATENT DOCUMENTS

| | | | | |
|---|---|---|---|---|
| 5,817,225 | A | 10/1998 | Hinton | |
| 5,849,491 | A | 12/1998 | Radomski et al. | |
| 6,001,574 | A | 12/1999 | Short et al. | |
| 6,054,267 | A | 4/2000 | Short | |
| 6,057,103 | A | 5/2000 | Short | |
| 6,261,842 | B1 * | 7/2001 | Handelsman et al. | 435/479 |
| 6,280,926 | B1 | 8/2001 | Short | |
| 6,770,698 | B1 * | 8/2004 | Chu et al. | 524/458 |
| 6,989,249 | B2 | 1/2006 | Nalin et al. | 435/91.1 |

FOREIGN PATENT DOCUMENTS

| | | |
|---|---|---|
| WO | 98/58085 | 12/1998 |
| WO | 99/00168 | 1/1999 |
| WO | WO 99/00168 * | 1/1999 |
| WO | 99/10539 | 3/1999 |
| WO | 01/40497 | 6/2001 |
| WO | 01/040497 A2 | 6/2001 |
| WO | 01/040497 A3 | 6/2001 |
| WO | 01/81357 | 11/2001 |

OTHER PUBLICATIONS

Young et al., 1993, Polyvinylpyrrolidone-agarose gel electrophoresis purification of polymerase chain reaction-amplifiable DNA from soils, Applied and Environmental Microbiology, 59(6): 1972-1974.*

Berthelet et al., 1996, Rapid, direct extraction of DNA form soils for PCR analysis using polyvinylpolypyrrolidone spin columns, FEMS Microbiology Letters, 138: 17-22.*

Wang et al., 2002, Separation of double-stranded DNA fragments by capillary electrophoresis using polyvinylpyrrolidone and poly(N,N-dimethylacrylamide) trasient interpenetrating network, Electrophoresis, 23: 1460-1466.*

Song et al, 2001, Separation of double-stranded DNA fragments by capillary electrophoresis in interpenetrating networks of polyacrylamidde polyvinylpyrrolidone, Electrophoresis, 22: 3688-3698.*

Amann, et al., "Phylogenetic Identification and In Situ Detection of Individual Microbial Cells without Cultivation," *Microbiological Reviews* (1995) 59(1):143-169.

Berthelet, et al., "Rapid, direct extraction of DNA from soils for PCR analysis using polyvinylpolypyrrolidone spin columns," *FEMS Microbiology Letters* (1996) 138:17-22.

Brady, et al., "Cloning and Heterologous Expression of a Natural Product Biosynthetic Gene Cluster from eDNA," *Organic Letters* (2001) 3(13):1981-1984.

Cottrell, et al., "Chitinases from Uncultured Marine Microorganisms," *Applied and Environmental Microbiology* (1999) 65(6):2553-2557.

Entcheva, et al., "Direct Cloning from Enrichment Cultures, a Reliable Strategy for Isolation of Complete Operons and Genes from Microbial Consortia," *Applied and Environmental Microbiology* (2001) 67(1):89-99.

(Continued)

*Primary Examiner*—Amber D. Steele
(74) *Attorney, Agent, or Firm*—Pillsbury Winthrop Shaw Pittman LLP

(57) ABSTRACT

The present invention relates to a device for the isolation and/or purification of nucleic acid molecules suitable to bind and/or inactivate inhibitors of the activity of reagents or enzymes used for DNA manipulation and to separate a plurality of nucleic acid molecules with respect to their size. Moreover, the invention relates to a method for the isolation of a nucleic acid molecule comprising applying a sample to the device of the invention wherein said nucleic acid molecule preferably represents a fraction of the metagenome of a given habitat. Furthermore, the invention relates to a method for the generation of at least one gene library comprising nucleic acid molecules isolated by the method of the invention and to a nucleic acid molecule isolated by the method of the invention.

13 Claims, 13 Drawing Sheets

OTHER PUBLICATIONS

Handelsman, et al., "Molecular biological access to the chemistry of unknown soil microbes: a new frontier for natural products," *Crosstalk* (1998) 5(10):R245-R249.
Henne, et al., "Construction of Environmental DNA Libraries in *Escherichia coli* and Screening for the Presence of Genes Conferring Utilization of 4-Hydroxybutyrate," *Applied and Environmental Microbiology* (1999) 65(9):3901-3907.
Henne, et al., "Screening of Environmental DNA Libraries for the Presence of Genes Conferring Lipolytic Activity on *Escherichia coli*," *Applied and Environmental Microbiology* (2000) 66(7):3113-3116.
Holben, et al., "DNA Probe Method for the Detection of Specific Microorganisms in the Soil Bacterial Community," *Applied and Environmental Microbiology* (1998) 54(3):703-711.
Jackson, et al., "A Simple, Efficient Method for the Separation of Humic Substances and DNA from Environmental Samples," *Applied and Environmental Microbiology* (1997) 63(12):4993-4995.
Miller, "Evaluation of gel filtration resins for the removal of PCR-inhibitory substances from soils and sediments," *Journal of Microbiological Methods* (2001) 44:49-58.
Rondon, et al., "Cloning the Soil Metagenome: a Strategy for Accessing the Genetic and Functional Diversity of Uncultured Microorganisms," *Applied and Environmental Microbiology* (2000) 66(6):2541-2547.
Schmidt, et al., "Analysis of a Marine Picoplankton Community by 16S rRNA Gene Cloning and Sequencing," *Journal of Bacteriology* (1991) 173(14):4371-4378.
Schwecke, et al., "The biosynthetic gene cluster for the polyketide immunosuppressant rapamycin," *Proc. Natl. Acad. Sci. USA* (1995) 92:7839-7843.
Smalla, et al., "Rapid DNA extraction protocol from soil for polymerase chain reaction-mediated amplification," *Journal of Applied Bacteriology* (1993) 74:78-85.
Somerville, et al., "Simple, Rapid Method for Direct Isolation of Nucleic Acids from Aquatic Environments," *Applied and Environmental Microbiology* (1989) 55(3):548-554.
Straub, et al., "Removal of PCR Inhibiting Substances in Sewage Sludge Amended Soil," *Wat. Sci. Tech.* (1995) 31(5-6):311-315.
Tebbe, et al., "Interference of Humic Acids and DNA Extracted Directly from Soil in Detection and Transformation of Recombinant DNA from Bacteria and a Yeast," *Applied and Environmental Microbiology* (1993) 59(8):2657-2665.
Torsvik, "Isolation of Bacterial DNA from Soil," *Soil Biol. Biochem.* (1980) 12:15-21.
Torsvik, et al., "Determination of Bacterial DNA in Soil," *Soil Biol. Biochem.* (1978) 10:7-12.
Tsai, et al., "Rapid Method for Separation of Bacterial DNA from Humic Substances in Sediments for Polymerase Chain Reaction," *Applied and Environmental Microbiology* (1992) 58(7):2292-2295.
Tsai, et al., "Extraction of Nucleic Acids from Environmental Samples," in *Environmental Molecular Microbiology: Protocols and Applications*, Horizon Scientific Press, Wymondham, U.K., pp. 15-30 (2001).
Wang, et al., "Novel Natural Products from Soil DNA Libraries in a Streptomycete Host," *Organic Letters* (2000) 2(16):2401-2404.
Young, et al., "Polyvinylpyrrolidone-Agarose Gel Electrophoresis Purification of Polymerase Chain Reaction-Amplifiable DNA from Soils," *Applied and Environmental Microbiology* (1993) 59(6):1972-1974.
Zhou, et al., "DNA Recovery from Soils of Diverse Composition," *Applied and Environmental Microbiology* (1996) 62(2):316-322.
Database WPI, Section Ch, Week 198934, Derwent Publications, Ltd., London, GB; Class B04, AN 1989-246867 & SU 1 439 124 A (Anti-Plague Mikrob), Nov. 1988, Abstract, X002266614.
MacNeil et al., "Expression and Isolation of Antimicrobial Small Molecules from Soil DNA Libraries", *Journal of Microbiology and Biotechnology*, Apr. 2001; 3(2): 301-308, XP 001050545.
Beja et al. "Construction and analysis of bacterial artificial chromosome libraries from a marine microbial assemblage" *Environmental Microbiology*, Oct. 20000; 2(5): 516-529, WP002277482.
Quaiser et al, "First insight into the genome of an uncultivated crenarchaeote from soil", *Environmental Microbiology*, Oct. 2002; 4(10): 603-611, XP002266613.
Roose-Amsaleg et al. , "Extraction and purification of microbial DNA from soil and sediment samples", *Applied Soil Ecology*, Sep. 2001; 18(1): 47-60, XP002266612.
LeBrenton et al., "Demonstration of extraction and PCR amplification of DNA from phytoplankton of lakes with high humic acid content", *Hydrobiologia*, Nov. 2000; 438(1): 91-97, XP008026153.

* cited by examiner

Model structure of humic acid (Stevenson 1982)

Model structure of fulvic acid by Buffle

Polyvinylpyrrolidone (PVP)

2-Phase Column-purification of DNA

SEQUENCE LISTING

<160> NUMBER OF SEQ ID NOS: 35

<210> SEQ ID NO 1
<211> LENGTH: 33925
<212> TYPE: DNA
<213> ORGANISM: Crenarchaeote

<400> SEQUENCE: 1

```
cacagccttg ttgatcataa cattaaaact taattcttcc agagaaattc ttttttctc      60
caagttttct gcaattgatt gcactatttt ttttatcttt tcctttgctc tttcaaagtc    120
tttttctgaa aatatttctt taaggacatt taatatgtca tagaaagctt gtcttattat    180
tggaggtgta tgagacttct tccctgttaa tcctttaaca tctacagttc cgtcctccaa    240
tacacctagg taattttttt ttagttcact aaaaaccacg tagcgatatc ttttatctat    300
ctccaaatct atgcctagtt cttttttaga ccaggatgaa attccactta atccttcctt    360
ggaaggattc tttaggaaca gagaatccgt atcaccgtaa ataacctcaa tcttttcttc    420
gttgcatttt tcaatagttt ttgttgtggt catccttcca accgctgcgg tagcctcagc    480
tacaggtaaa caatagagcg gaaatatttc agcacccata accccatacg tagcatttaa    540
aataaccttt atggcctgac tgataacact gtatagctgt ttatcctctt tatccaaaga    600
attatccttt gatagatatt tgtaataatt aacccttaga tcccttaggg ttcctatcaa    660
tatggaggtc atcccttgct tttccttgca aacccaatgg tttgtttgct caatatgtgt    720
tgatggatcc cttctgcaat tttcatgagg acaattgact gtttcgtaag ataaattgtg    780
aactttaatt atgctaggat acagactagc aaaatctaca actatgacat tgaaatgaat    840
tcctaaaacg ggctcaacca ccagacctcc tcgatatttt ttttccttta taatggcaac    900
tgtagacgat gttccttttt tctgtaattc atctttacgg ggaataatga tattttgctg    960
cctatgttca aaaaacatca tggacctaat ccattgattc accccgaatc ttgttatatc   1020
ttctattgac attcgggata tcctagaaat gataatcaac aattttatca gtaaattgtc   1080
attgaaagat gtcagacgaa atgtcaagtc tgcatctttg aggcaatact cggccagttt   1140
ttccaatgga agatcaccta tgctttcatc aaagtctatt tttgactcgt ttaatagggc   1200
ttcgcagata gcatttaaag taaactcaga gtatttatga ctaaaagcat aattctgtac   1260
agatttattt tgaaatgtcc tgaataaatc gatatggatt ccatgcttta aggaaaccgg   1320
atccgcctga ataccccttt ttataaaaga gtcttttttta actaaaatag gcaccaattc   1380
tttactaatg ggtttttttgt gtacagggtc tatcgatggg tcttgagatc tagcatataa   1440
ataaggtaaa tcaaaatcat caccattaaa ggttaaaact attggataat tttgaataat   1500
agcaaaaact tttagtatca tgtctttttc gctatcacat aattcaacgg ttgttgaatc   1560
tagtttagag ggatcaaaat ttggatcttt tcttaagacg aataccttc taaatccatc   1620
cgatgccgat aaacccactg cagtaattac tttatcgtga tctctggctg tgggcatcct   1680
tccctcttca gagtccactt ctatatccaa agaaattctt ttgatatccg gaataggctg   1740
gtttaacaat cttgaccact ttattagaaa ctcattatat tcactacttt ttggctcatt   1800
ttctttaaaa ttaggtttta tgagattatc cagatattcg tcaactttct ctggcattgg   1860
gaattcatga aaaactaaat tattgcctat tctgttataa aacgctcccg gaattagacc   1920
caaatcgaat aaataacttt catggtattt gatatcagcc tcccaagaag taacctttc   1980
cctaaaacta ctatctgttc caccaatgga aagggggtca ggggcaatta ttttaaaaac   2040
```

-continued

```
cgatatttcc ttgtcctcaa tatcgtccat tttttttatt ttttctagtc taaacctatg   2100
tggctctttg ctaactattg ttttaacctg atcagaatag agttccttta caaagcaata   2160
aggttgatgt ttatttatat gattttcaat aaaagactcg ctccaaaaat atatttgaga   2220
atcttctgga ttgtaaaact tcaaaaacac tgattttttt tctcctatgt aaacggaaga   2280
aagtaacaat gatggaatat tttctggaag ttctttttga taataactat ttttctcctc   2340
cagaggcaag tcggatttta tcaccatatt tttatttcat tcatcctttt aaaaattaat   2400
gacttgtttt agaaaactat caaatttgat ttacctagca ccatcaaggc tgatgtctga   2460
ctaggttatt tttagcatta ctgatttatt tttctttgag gacaaacctt cttaagaata   2520
tacccattat attattcaag cgtgtcaatc gttaactcag tattatcaat atcgacagca   2580
atgtgagaac aagagggttt ggatgtggat ggatgatcaa tggttgattt tcaaattcct   2640
gtatgaaata ttgtgagcaa tcgatatatc attagataaa agaagattta gttaggacat   2700
cttgataata tattcgtgta gattgatttg aaaaaacagc agcaataaga aaatttaata   2760
cgataaaata cgataacttc gactaactaa catcccttgg gaaaagaact taatgcccga   2820
tccccttttt tttgtttttt aaagaaaaaa gaagatttat attaacaatc ctaccataag   2880
tagtagaacg cgtccaagac aaaaggcggc gtcggtgatg aagttggttt gtgccataaa   2940
gtgatttact gacctccaga tgcgctcgtt acattactgg ttaacgatat aatattaaaa   3000
tagtgggata atggggattc gatcaacaca tcggaactga cttgatggat cggatctgac   3060
atgggaagat cagacagaca ttgaaaaaga ttcattataa cagcacaaaa gatatcattg   3120
caggcattgt ttgtatgtgt gtgacaatac aatacagcat atgcttgtga gttaatctaa   3180
caaataacca aataaacaaa tcagaaggtt attagagttt ttctttcttt ttcgatcgta   3240
ctctctttcc ctgcttttta aaggcaggga gaaaactcaa taaacgttct tttgtgtttg   3300
ccaatggctt ttccctcttt ctcttaccgt cttctcggat gtgagggcgg aggcgggaag   3360
gttgttggca gagaccaaag caacgcgtat atacaccata aagcaaaagt caaccgatag   3420
gtaacaaatg gcgcacgttt gtgttttttt ccttgtggcg ttttgcctct ctcaaaaaag   3480
gcaaggcaaa acccatatgt gtgcgtttgt catctgttat gtttttcacc atcatcattt   3540
tttttgaat ccggttgatc ctgccggacc cgactgctat cagagtggga ctaagccatg   3600
cgagtcaaca tagcaatatg tggcatacgg ctcagtaaca cgtagtcaac atgcccaggg   3660
gacgtggata acctcgggaa actgaggata aaccgcgata agtcactact tctggaatgg   3720
gtaatgactt aaatctatat ggcccctgga ttggactgcg gccgatcagg ctgttggtga   3780
ggtaatggcc caccaaacct gtaaccggta cgggctctga gaggaggagc ccggagatgg   3840
gcactgagac aagggcccag gccctatggg gcgcagcagg cgcgaaacct ctgcaatagg   3900
cgaaagcctg acagggttac tctgagtgat ttccgttaag gagatctttt ggcacctcta   3960
aaaatggtgc agaataaggg gtgggcaagt ctggtgtcag ccgccgcggt aataccagca   4020
ccccgagtgg tcgggacgtt tattgggcct aaagcatccg tagccggttc tacaagtctt   4080
ccgttaaatc cacctgctta acagatgggc tgcggaagat actatggagc taggaggcgg   4140
gagaggcaag cggtactcga tgggtagggg taaaatccgt tgatccattg aagaccacca   4200
gtggcgaagg cggcttgcca gaacgcgctc gacggtgagg gatgaaagct gggggagcaa   4260
accggattag atacccgggt agtcccagct gtaaacgatg cagactcggt gatgaattgg   4320
cttcatgcca attcagtgcc gcagggaagc cgttaagttt gccgcctggg gagtacggtc   4380
```

-continued

```
gcaagactga aacttaaagg aattggcggg ggagcaccac aaggggtgaa gcctgcggtt   4440
caattggagt caacgccgga aatcttaccg gggcgacag cagaatgaag gtcaagccga   4500
agactttacc agacaagctg agaggaggtg catggccgtc gccagctcgt gccgtgaggt   4560
gtcctgttaa gtcaggtaac gagcgagacc cctgcctcta gttgctacca ttattctcag   4620
gagtagtgga gctaattaga gggactgccg tcgctgagac ggaggaagga gggggctacg   4680
gcaggtcagt atgccccgaa accctcgggc cacacgcggg ctgcaatggt aaggacaatg   4740
agtatcgatt ccgaaaggag gaggcaatct ctaaacctta ccacagttat gattgagggc   4800
tgaaactcgc cctcatgaat atggaatccc tagtaaccgc gtgtcactat cgcgcggtga   4860
atacgtccct gctccttgca cacaccgccc gtcgcttcat cgaagttggt tcttggcgag   4920
gtgatgccta attggtacta tcgaacctgg ggtcagcaac gagggagaag tcgtaacaag   4980
gtggccgtag gggaacctgc ggccggatca cctccttagt tatcatatct tgcaacacag   5040
aacaaaatag acaaaaagag aaaaatgggt gggaatgaag gaaaaactct acccaccgtt   5100
taatttgttt ccttgggatc ttggtcagct tggtttacaa acatgaatgc tgcagagtat   5160
acatcacaca tgcaaaaaca aagcctgcag tggtatctgt gcaagtgtta taatggacat   5220
ggatagggat atgggcatgg atgtgggcaa cacaacacaa agtagtgttg ctagaccaga   5280
tccgctctgc tcagtgagag tggaacaaat ttgctagtga cctgtctcta tctgaatgaa   5340
tgtgtctgtc tgtctggtct tttgcgtatg cgtacccgtc ccgtgccaaa gagtcggtcg   5400
gtggttaagc caacacaata accatcagag taaaaaaaac agagtaatgc acgcacacac   5460
acatgtgcac acagaaaaag cagaaaggaa aagagaaaga aagaaaagga aggaaagaaa   5520
gaaaaaaagt gaatacggat gcaattcttt gtcactaaac tgaggagttg gagagacaaa   5580
ggatgaaggt gacatagcag gcaacaccta gacaaatatc agaaggttgt tgtttgcgat   5640
gatgtcgtgt ataggatcaa accattaaaa gatataacaa tacattagat atattaaaaa   5700
tataatgatt cacgtaaaaa tgaaatagtg aaaaattata aaaaaatgta tatctggttg   5760
tagtgcagtg taatacataa aaagcgaatg attttatcat gaaaaccgaa aattaattag   5820
ttattaccat caatagaaaa caaaattgga aactggaact ggtgcaaaga cgccggttgg   5880
tggatgactc ggcttgataa gcgaagaagg acgtggcaag ctgcgataag cctggggtag   5940
gtgcatgcga ccgtcgatcc cgggatgtcc gaatgaggtc tctctttaca ctcccttgct   6000
ttgttgcttg ggagagcgaa ccgtccgaag tgaagcatct gagtaggacg aggaggagaa   6060
atcaattgag attccgtcag tagcggcgag cgaaagcgga acagcccaaa ctgaatctgc   6120
cgtggtaaca cggcagagat gtggtgttgc ggttatagcg cataggatcc tgcctttgga   6180
gctgaagtgt actggaatgt accggaacag agggtgatac cccgtaggc aaatggaggc   6240
gggattctgc tatatccaga gtagctggcc ttggcagtgg ccagtgaagg tgggtgaaag   6300
tagtatccaa ggctaaatat tcatcaagac cgatagaaaa ctagtaccgt gagggaaagt   6360
tgaaaagtac ccggaaggg gggttaaaag cgcctgaaac caaccggtta cagacgtgta   6420
tggctcgaaa ggataaaatc tagagtcata cgttccgtct agaaacacgg gccagggaga   6480
ttgctgtcat ggcaagctta acctttaca aagggaatgc gaagggaaac cgaatttgcg   6540
cattttctct ttattgagaa aagaggcaat ggatctgaaa gggtctcaag tcatggcagt   6600
aaggctagaa accggacgat ctattcctgg ataagacgaa ggtgagtgaa aactcgctgg   6660
aggtctgcaa gggtcctgac gtgcaaatcg gtcccctgat ctgggattag gggtcaaaaa   6720
ccaatctagt ccggtgatcg ctagttccca ccgaagtgga tcgcagtcct gccttagctg   6780
```

-continued

```
agatggcctg tattgtagag caccgatcgg gcggtaaggg ctcgaaagag ctcgccatcc   6840
attcgaactc cgaatatacg ggcgtcgtag aagctaggag gcgggtttat gtggggtaag   6900
cctcataacc gagaggggga caacccagac taaagttaag gtccccaaat gtctactaag   6960
tgtcaaacca aagggtgttt tcgagcagag acagcaggaa ggtaggctca gaagcagcca   7020
ttctttaaag agtgcgtaac agctcacctg ccgagctcga aagccccgaa aatgtacggg   7080
gctcaagtag actaccgata ctttagacca ccgacgatgt cggtgcgtgg taggtgggcg   7140
tagtgtttgg gtagaagctg ggctgtaaag tccagtggac cgaactacta gtgcagatcc   7200
tggtggtagt aacagcatag ccgggtgaga atctcggcga ccgcatgggc aagggtttcc   7260
cggcaatgcg tcatcagccg ggagttagcc ggtcctaaaa acaacctcaa cagaattgtt   7320
tgaatgggaa actggttaat attccagtgc cttgaaagtt cgttaacacc ttttctgtcg   7380
cttccggata gggtaagcag aaccgtcgtt ctgtccaagt attctagctt tgaggagtac   7440
cgtaatggcg agaatcaaag cgagatacga atggcccttc gcaaggaggg tttgcttgag   7500
tccaggagac actgaaagca gaaacaggga gatactttca agaccgtacc gagatccgac   7560
actggtgccc tggatgagaa gtctaaggtc tatcgggtat accgtatggc aagggaactc   7620
ggcaaaatag ctccgtacct atggtataag gagtgcctgc agtttttacg aggagtaggg   7680
attgcaggtc gcagtgacta gggggtcccg actgtttaat aaaaacacag gtggtcgcta   7740
gtccgaaagg atgtgtatgg cctctgtatc ctggccagtg gcggtaccta aaacctgggt   7800
acaaccgggc taagggccgc taaacgccgg gagtaactct gactctctta aggtagccaa   7860
atgccttgtc gggtaagttc cgacgtgcat gaatggaaca acgagggccc cgctgtccct   7920
gcctacaacc cggtgaagcc acataacgtg gacgaacagt ccacgaacct ctgtcgggga   7980
gagaagaccc tgtggagctt tactgcagcc tgttgttgcg atatggttgc aaatgcagag   8040
agtagctggg agccgttatg gtcagttctc cgggactgat ctaggcgaca gtgtaacacc   8100
agccatttgt taccgtatcg ctaacctgct tatgcaggga catcggcagg tgggcagttc   8160
ggctggggcg gcaccccctt gaaaatgtat cgagggggcc caaagattgg ctcaggcggg   8220
acagaactcc gccggtgagg gcaaagccaa aagccagtct gactggattc ccaatgatac   8280
gggattcaga ggcgaaagcc gggcttagcg atccatcatg tcctcactat tgggggctgg   8340
tggtgacaga aaagttaccc tagggataac aggctcgtcg cgggcgagag ctcccatcga   8400
ccccgcggtt tggtacctcg atgtcggctc ttcccatcct ggttctgcag caggagccaa   8460
gggtggggct gctcgcccat taaaggggaa cgtgagctgg gtttagaccg tcgtgagaca   8520
ggtcggtctc tgcctgacag gggcgtggtt gtctgagggg aagttgcccc tagtacgaga   8580
ggaacagggc agcgcagcct ctggtttatc agttgtccga cagggcaagc tgagcagcta   8640
agctgtttag gataactcct gaaagcatct aaggaggaag cctttcccga gacaagacaa   8700
ccttccgtaa ggagaagggc ggccatagaa gatggcgttg atggaatgga ggtgtaagca   8760
ccaagctttc aagcgaggtg ttcagcctgc catcaccaat agcccaacgc acctgttgac   8820
aaaacaaaaa aaaccgacag acagaaaaaa ttgaaaatct ataactaaat atacatattt   8880
ttttgttggt tcattatttc atgcgtaaag agtcaattat agaccaattt gatatatcta   8940
ctgattattg ttatatagaa ttttttaatg gatattgatc ataaaatttt agtatatttc   9000
atattatcta ttaacaaaat aattattaca atgggtttgg tttcggatag acaaagaaac   9060
gagacaatgg attttataaa aatactggga tataacatca gatatataaa aatagatcaa   9120
```

-continued

```
gtcaagtcaa atgaaaccat aattctgctt catggtatag gagcttccgc agaacgatgg   9180
tcagaattag tcccattttt gtataattgc aatataatta taccagacat cattggtttt   9240
ggttacagtg aaaaaccaag gatagagtac aacatagatt tatttgtaaa gtttttggat   9300
gaattgtttc tgaaacttga aatcaaaaac cccataataa tgggttcgtc ttttggtggt   9360
caattgattt tagaatatta tttcaggcac aaagactttt ttaaaaaaat gattctagtg   9420
tccccggccg gtacccaaga gagaccgaca ctagcgttaa ggcaatacac ttactcatgt   9480
ttatacccaa caagagaaaa taccgaaaga gcatttaaga tgatgtcgca tttcaatcac   9540
acagtaaaag attcaatgat aaaggatttt attaatagaa tgaagcagcc caacgcaaaa   9600
cactcgtttg tttcaacact tttagcacta aggaaaaata gtgatttaca agacaacctg   9660
agggaaatca aaatcccaac tttagtaata tggggaaaag aggacaacac cattccagta   9720
gaaaatatag agtatttcag ggcatccct tttgtaaaaa catgcataat gagtgattgc   9780
ggtcatgtgc cttttgttga aaagcctctt gagttttata aaatagtcaa agagtttatc   9840
gactcctaat ttctaatata agtattatat tcaacattaa aatattattg aatcaatcca   9900
cttctatgag taatgagaat gaagaaaata aagatataga ttttaagaaa tccattgaaa   9960
aggctgcgga attccagcag gatttgttgc gacagttctc tacaattcaa tacaatgcgt  10020
ttcagaatat gttttcatct ttgcaaggat ttacaaatta taatgccatg tttaaaacca  10080
ccgtacagac gggtggcagg atctcaattc ccgaagcaga aagaaatgct ttggggattg  10140
aagagggtga tctagtccag gttataatta taccgttgac aaggaaaaag aaaaacacaa  10200
gttaaaataa caaatccgtt aatgtgtttg aatccatttt ccaatttttg gtaaaacatt  10260
tttctgtgaa aagttgctag caattagccc tacatgccct gttggaaatt tcatcaggct  10320
tttatcctga cttgaaatta ggttgtttag ggagctactg ctgtcagacg ttacaaggtg  10380
gtcaaattca gctacaacat taagaacggg aaccttaatg tttgacaaat ttatcttgtt  10440
ttcacccaca atcatcttgt tttttgcaaa aaggttttgc tgatagatat cctttaccca  10500
ttgcctaaag gtttcccccg caataggagg tgtgtcatac agccatttct ctattcttaa  10560
aaagttctgt acaaaacttt catcttcaaa gtttttaaat aaattatagt atttgtttac  10620
accttgcttg aatggtttta gtgatgcata aaccagatac agtaattcat atggaaagtt  10680
ttcgtgatag gacagtactt tgtcaatatc catgtgctca gccatgtttt ttattacgga  10740
tttgtctttc tcggcatcaa caattggagc aatggtgact agatttttaa tgttttttg   10800
atatagcgaa gtgtacatca aggacattgt accccccatg caatatcctt gtaatgaaat  10860
ctgatcaatg ttttctatgt tttttatgta ttctacacac tcataaataa acaaattgac  10920
ataatcatca acagtgatgt atttatccag ttttgacggg ggtttccagt caatcagata  10980
gacatttatg ccctgctcta gcaggttcct tatccaactt ttgtcgttct gcagatccaa  11040
aatatatgat ttgtttatta atgcataaac aatcaacaaa gggtacttga aagtttgttg  11100
ctttaggggt ttataatgta gtaaacggaa gagggttgtt tcccttatta cctcatattc  11160
gcttgatcca gtctttatgt tttctatatt cgacaatttt ttcctgattt cttttaattt  11220
tgaaatgtta tcaggatccc ttacaaacgt aaaataatca ttcactaaat aattaattaa  11280
ggaattattc atttttttc tcatttaatt tttttttgat ttccaatgat attttttga   11340
tttcatagag attataaaat aacaggtctt tttcttcttt tgacagttgt tgttgtgacc  11400
taaacaaaac ggcatttgaa tcgtaaattt tttgataact tttgatgaca tcaatgctgg  11460
aattcaataa attgttataa ttgattgaaa agtctgttga ctgcaacatt gacgagaaca  11520
```

-continued

```
catcctcaaa agtatttatg attattttcc taatatcgtc ggggtttttt tcatctatag  11580
cagacgatac cttgtttacg gccaacaaat aagcatttat catacgggaa aagtataggt  11640
tgagaaatga ctgatatctc agtaacaaat taccgtgttc ctttaatgta tttaaattaa  11700
ggtttggatc attcattaaa gaggtgaatg gccccaaggt tgtaaggcta tttaactctg  11760
ttaattgttt tataaagttt tcaaatacag actgaagtcc tgcctcttca gatagagtgt  11820
ttttactgtt tttttcctct ccaatattgt tattttctaa ttgcaaatga ttgattcacc  11880
tcggattcga aactcttgta attgtaataa tttttcatca acaatactat attctttact  11940
ttttgtcatt ataaactttt tttagggtta ggaagaaatg aaatttattg tcatttaaca  12000
aacttgaaaa gcaattatcg caggtcaagt gtatgttaca ttgacaattc cttttagtag  12060
agagcagttc ctaaaaactg tcaaaatgga cggatggtaa aaacccattt ccaggcaaaa  12120
gcgcaactgg aatcagaaag tgtttattcc aaagtttgac catccctctg gactctattt  12180
taacgggtct gataatttta atatccttcg gttatacaaa atatggcaca tgacactgat  12240
ttaatgcttt tatgctttga ttatcacctt tttatattga aaaaacgact catgcattaa  12300
aatagtaaaa ttattctaaa taattttaga tattcacatt taggcaaata attagaagat  12360
aaagccaagg caggcccaac aattttataa ggtaatccta ccaagacgac tgggggtccg  12420
tagctcagca tggatagagc gcctgccttc tatctttacg ggagatagcc ggaagtcgag  12480
ggatcgaagc cctccgggcc cgttaacctt atggggttca aatatttttt cagttctaat  12540
gcccatagaa ggagtatgaa tggacacatc attgcctgaa gttaacaaca accatcacaa  12600
aaatgaagaa gagaaaggca taattagttg acgaatgtga tgtcggagtt cttttattgt  12660
ttggccggtg tctacgcgtc agaaaactgc caaaacgggc tgctcgaggt actggcaaga  12720
catcccgaac agccttgtga tcttctttag ccactgaaaa acatgatggc gtaaggggct  12780
acctcccttc agcgatatat cgctaaccgc actgcacttc cctagcggtc agatttcaag  12840
tacacagcca tcagtagcct ctaccctgta cgcgaatgac gatattcctt gttgcaaact  12900
tttgttctga atgacatccg tcgcagtatg cagcactagc caggcgtatg catccttcag  12960
atcgccaaag caaaagtgga tgtattcgtt accccttcca tgtgagcaga cgtccctcac  13020
attgtcactt gcactcctgg gcgtggggcg ctagatttgg gttgcccagt aatcattgcg  13080
ggcccaaagg cggggtttgt ttctgggtgg cccggcataa tttgcaaaaa aaggagaaaa  13140
agaacctgac ccttgtcaaa aaatttatat ataggtagag atggttgtct atttttgtat  13200
acaggcacat gagtaattac ccaaatatta tctatggcga aaccatatat agaaacaatg  13260
agccaaggca gacatttgcc aaaaccattc gtttgtggat ggattctttc tattgtcccc  13320
cacataaccc tcttcccgag gctgatacag catcttagtt tttgggtatg cgcatacccg  13380
cccaccatgt caaaagaatg tatacatacc accgctggtt tggacatgta taaaacatct  13440
gaacttgtag gcatgtctca tgcaatgcgc catatggacg atgcggtgac ggtggatttg  13500
ccttactgct gcaaaaactc aaacaaggta ggccccattg gaaggacagc atgttctaag  13560
tcggggaaaa cggggcatgc gggtcatttt caggaggaga gtaatatccg tagccccatg  13620
ccaaatgctt gcagtctcaa ggccttgatt tgcgctctgc gcgtttgttt ctttttgaat  13680
acttaactta aggtctggtg cctgttacag ttgatattcc accataggtt gtagatgcag  13740
agttattgct attatcagaa gtcggatttc cgggtgtctt gaaatcttgt atggagtgag  13800
tgtgctttgc ggtaccatct atcttaacca tataaaaagc agcattgaag acaactgtgg  13860
```

-continued tggaattaat atttgcgaat ttatatacgc caacaactat ccacgcagga tgagttgaac 13920
taccattgtt tgttgtgctg gttatagccc tatagcccct tttatatcat tctatcaagg 13980
tttgtaggat tttgtgaatg gcatatttga atctggctca tcaatatcac aatggcagaa 14040
attattacta ttgaagacaa tgataggagt ttatgtttat tgccatgcat attaagaact 14100
gaattaaaaa catggcatat aaaattctat ttttgtgact gggataaaga ataacatatt 14160
ttgtgttatg ggtcatactc aagaattgag actcatcata gttggtgttt ttggttttag 14220
aatcaaaaga agaaaagaac aacagcaata caagttcaaa aagacgttac ccgatcgcta 14280
atgacaatga tttggaactt ctttctattt ttaactattt tgattaggtt acagattcta 14340
ttgttgtcat tacatttttt gccactgtct gccagtttgg gagttggaaa ctgacctttt 14400
ttccttcagt cgccttttg attatgccat atttatttag catttttacg cactcttctg 14460
caaacagggt ggtttctcca tattctatta gttttatgtt tgtattacca ttttttaagt 14520
atagttcttc aaaaacgggg agtttccagg caacagtggg aacacacgaa actaaggcct 14580
cagccacagc aatgccaaaa ccctctctgg atgatggaaa aataaagact ttagatttag 14640
aataaaggct aatcttttct tcctcggaga caaagcctct gtgatctata cccgcattac 14700
gtagttttgc agccttatca gggggtatgc gcccaaccat tacaaaatta gattctggtc 14760
tgagtgtttt tattgcagtc caaatttcct ccagtccatg aaatttttct atccttccga 14820
tacaaagaaa atcaatgtcc tttttattgt tgattactcc tctgttggaa tcctttaaaa 14880
agatattttt atctattcca gttcctacaa tggcaattct gttggtcaga tttttgcta 14940 attccctggt tttttattt gctgtttcct tcaaattatt gattttgcta acccctattc 15000
catagactgt gttgagttca tgctttgacg cttgactcac ggtcaaaatc atatcagaat 15060
ccttaagcat caccgcagta gccttttgta ttagataatt gtacagaaat tcaaaatagt 15120
tcttgcaaat agatatccgc ggttcatggt gatgaaacac aacaaagatc ttggtttttg 15180
gcttgaatag cctaagtagc agccaaagga caatattaga ttcgccccaa gaatccaaaa 15240
tggcaatatc tggacgtttg gcaaggggcc gttaaagcat tgtatgtgtc ggttataatc 15300
ctatttggta tttttttgc ggagttatgg ttgtatatct tcaagacaga atagcagccg 15360
cttttgtcta tcaggtctgc aactttttc atccagagaa atcctccggt gtaattcttt 15420
aaacttgaag ggtaaccaaa gaataataat ttaatttgtt ttgcgttgct tttaatcatc 15480
ctcgttgtta tatataacta taaagaacac ttattttata attgttattg ttaagaacaa 15540
gataatcaac attttggaca aacatgataa aagaattgaa aaaatgacac aataaattaa 15600
aatatttgga taatcgtcat ttacccttca acactgtgga cgatgcaaaa tatcgttttt 15660
gcagtattca tatttttctt tgcgcatatc catgaaaatg aggtttggag gttcatcagt 15720
tccttggcaa tatgtttttt gaaatattct ccaaatacat ctgtatatgc ggctccaaac 15780
tccagatttg ttccttttca aaaagatgcc catatctttg tgagctgccg ataagctccc 15840 ttttttcaa tttgtccaga taactagaat taaccttgga ttccgtaaaa ccattttca 15900 tggccaaagt attgagggtg ttgtgtatcc cagaaccatg ctgagctgct tcctttattc 15960
tatacgctat ctcttttgga atccctagtt tttctgcaag tttgcggtga accctttttc 16020
ctaggttgtc atagttattg ccattgtttt gaatattgag tcgcggatct attctcagta 16080
ccgtgtctat cagattagta tctaaaaagg gttcgcgtaa ctctatgctt tgagacatgg 16140
ttattttgtc ctctctttcc agtgtttctt tgtaaagtaa cttaatgtcc tctatcaggt 16200
atccctgaat tttttcgtat ccgtgttttt taacaatttt ggaataccag gaatatccgc 16260

-continued

```
caaacagttc gtctgccccc tgacctgtaa gcattacccg tattccctgt tcgtgagcca  16320
atttaaccgc gccatatatt ggaatggcaa cctcaacctg tcccatgttg tcatcttcaa  16380
ttatgctgat tatttttgga atggtacttt caacatcact ttcagtcatc tgttctattt  16440
ccaacttgag gtcaagtttt tctgctatct caagtgagtt gaggatatca cttgaacctt  16500
taatcccaga cgtatagcaa ataacttcgg gggccatttg ttttgccaaa tacgctacaa  16560
ttacactgtc aatcccaccg gagaaaacaa taccgatttt tttaaagtca ctcacacgtt  16620
ttctcataga ttcaaccaat gtatcaccat atgcgttaac cgcagaatcg atgtctgtgt  16680
acaggattga atatttctca catattgatt tttttgtatt tacagaaatc ggaaacaatg  16740
tagtcttgaa attggaggac ccttccttcc gcgaaatgac aagagcatag cctggcaaaa  16800
gtcttttgat ttggtcggac atagcaattt tccataaggc ttttctttct gatgcaaatg  16860
caatgaaatc actactttca ccatagtaaa tttgtcttac tccaatgcca tcccgtacca  16920
gcacaatatc tcctgtggac tgctctctaa tcgccaaaac ataaattcca tcaagctggg  16980
taacggttct ccttatagct tcgattagat cgcctttagt gttttgataa tggtcttcaa  17040
gaaggtgaac aataacttca ctatcagtcg aggtagtaaa agtgtgatgt gcagaaaggt  17100
tctttctgat ttctttatag ttatatattt caccattatg ctccagaatg agttttttat  17160
cacaactcac aaacggctgc tgaccacagg agccaccaac tattgccaaa cgactgtgac  17220
ctaaaacgtc atgcccctct acctgtgaaa acaatggatt atcaaaggta tcagaataaa  17280
ctatttgatt ctctgtagac aaacccatgc catccggacc ccggtttttc atacaggata  17340
gcatttttcc tatcaagggg gcaacatttc tctctttttt acttaaaatt ccaacaattc  17400
cacacatctt aaaatttcc tatacggtat ttattgatga acaaaatata aaagtaacca  17460
ctattgttgc cattatgggt tctaaacggt tctactctat aaaatcaagg acaccaatca  17520
tatccggtgt gtttacctta tttattgttt catttatata tttatcctta ggcatatatg  17580
cgatacctat tcctgcctgc tttatcatgc acaggtcacc tttagtatcg ccaatagcaa  17640
ttgtattttt tatgtctgca cagattttct ttgcatggat ttccatgtga tatctcttac  17700
acacagaatt cttgcaaaaa cagtctattt tttcccatcc taacggcata tttatttctc  17760
cggtgactat cccattgtct accttcaatt catttgcata aaaaaagtcc aaatcaagtt  17820
tgttcaccaa ggcctgagca gcaacactgt aactatctgt aattatccct attctgaacc  17880
ctttttctt cagcaaagat atcacctcct ggctgttctt tgcagggggg atggagtcca  17940
aagcaatttc tatttccctt tcttctattc ccctaatcac agcggctatc ttctgtgtct  18000
taacatagcc tggaatggat ttgtcggact ggatgtgtct gacctgagca tacaagccaa  18060
acttttttga caatacctca attagccttc catcaattag cgtcccatcc atatcaaaaa  18120
cggccaatgt agatttaaat tccataggat acaacaaaca aggaatgtca aagaatatta  18180
ctatttagcg acagcctatt agccaaaatg tttttatagg ttggggacat cattattcaa  18240
ttgggatgtc ttgggcacca attttttat ttcattagat atagccctat aaaaaggtta  18300
cattaaaaag tgttcgttag atcaatttta tgtatgtcat ttataaacga atatgcacat  18360
atagaaatat aaacacatga gattagatta tccacctaac tataccgaga ggataggagc  18420
agttagtatc catgcgcttc aaaagattta tgagatcgat tccggaaaga tgcccaagtt  18480
taatggcctg catcagcatc agtctataaa ggcctttggt tatgacgaac tgtcaagcat  18540
attccaagaa cttgccatag tcattccagt aaagaacgaa aaaatcagcc ttcttgaagg  18600
```

-continued

```
agtattgagc ggtattccaa atgaatgtct catcatcata gtttccaata gccaaaggac  18660
tcctgtcgac agatttgcca tggaggttga aatggtaagg cagtactcta gttttgcaga  18720
caagaaaata atgattattc accaaaatga tcctgagctg gctaatactt ttaagaaaat  18780
aaagtataga tccatcctca acaccaaaag tcaggttcgt agtggaaagg ctgaaggaat  18840
gataattgga atattgctgg caaaaatgca cctaaaagag tacattggat ttattgacag  18900
tgataattat tttccaggag cagtaaatga atatgtcaag atctttgcag cgggatttgg  18960
aatggcaacc accccataca gcaatatcag aatatcgtgg cgttccaaac ccaaaatcgt  19020
aaacaactca ctacaattcc caagatgggg tagaatttca gaatccagta acaaatacct  19080
gaacgctcta atatcccaca tcacagggtt tgaaagggag attatcacga ctggaaatgc  19140
aggtgagcat gcattatcca tgtcccttgc agaaaatctc aactattcaa gcggatattc  19200
ggttgagccc tatgagttta tcaacatttt agaaaagttt ggaggtctac tcccatcaaa  19260
caatcctgac atcatagaaa agggtatcga aatatttcaa atagagacca ggaatccaca  19320
ctttcatgag gaaaaaggaa atgatcattt ggcaggcatg atgcaagaat ctcttctcgc  19380
aataaacaac agcaaaattt gcaacacaga actgaccagg gaaataaatg accatttact  19440
catgcttcag gtaaaacaca ataatgatat gaccaaactc aactttaaga aaaaacacct  19500
tataatggat cccataaaaa taatacccat cgacaaattc gccgaatttg tagttaagaa  19560
ttctaaaacc ttcattagaa ttggataaaa atatgcagga atgcatattt ttgagaacaa  19620
caggtttggg aaattttgac tgatttttta gatccctcaa actgcacctt tatccatcct  19680
gttttatcaa gcctgaccaa gcgaatgcat aattatccga ccgtgttttg agcaaccaca  19740
gaggccactt tttttagaaa caacgtaaag ggataaaaaa cagttgttca ccaacatttc  19800
actagctggt gaataaatta tatcttcaaa cctttattct ccacccctac aaaccgaagg  19860
atcacagtac tcgcccatcg ctacctgaaa aaaaataagc aatagtcagt ttcggatttc  19920
aaaatttcaa attttccaga gaattaattt tcccctcatc atcaatgccg tcaattactc  19980
tgaagggtat ttttccagct ctttggtatt tttgtttatt acatattttt ctggatcata  20040
tccatatttt ttgcctaact cattcatgta ctcctgaaca tcatgccaag ctttttgctt  20100
gtcatatgga ttgccattta ggctgctacc tccactgccc aacgtagatt ttgatgaagc  20160
atccaatgca gtttggtata gctttgatat cttgctaaat tcctcatcag tcaaccttat  20220
atttttatta ttgttgttac tggtcattta ttattacccc attagtaaat atttgatgtt  20280
caaacttatc tttttctttt gataaaatgg agtcagcctt tgtagcacat tttggatatt  20340
aaacccaata cgacgcgtta cggaaaagat aaaagcacct aacacccttc aaaaacattc  20400
aacgatatga ctgaaagtag ccaaagaatt tgagaatatg ttctttctca tttatcagag  20460
actttttgtt tgggtttata attaattgat taacgttctg attgataaaa aagcgcaaaa  20520
tagcaaacca tgtaaatttg aaaaggggag tacatttggt tatggcttaa caatactgtg  20580
gttgtctcca aaatagtaaa ttttataatc taaaagtaga aaattcccta tgagtgatgc  20640
tatcgaaaat gtcctgatcc ttcagggagg aggatctttg ggtgcatttg gttgcggggt  20700
ctacaaagca ctagtaaaca ataacataaa acttgatatc ctgtctggca catcaattgg  20760
cggtttgaat gccacagtta ttgccggcag taaagaagat cgtccagaaa aatcattgga  20820
gaatttttgg atggaaatag ctgatactaa taatggtaat attaatacat accttaattt  20880
ccccttttttt gaaagtccct ttcctgggca aattcctttc cccttggcat cagaatcaac  20940
actatcattc tacagctctg ccatttatgg aaatagaaaa atctttctgc caagatgggg  21000
```

-continued

```
acctgaaaat atctttaaag atccacagta tttcacacct agcaaatgga catatttgta  21060
tgaccattca cctttggtaa aaaccttgga aaagtacatt gattatagca aattacagcc  21120
aaacggtaag cccaacgcaa ggctaataat aaccgcagtt aacgtgatga cggcggagcc  21180
ccttattttt gacagtgcca agcaacaaat aaccccaaaa cacatacttg caaccactgc  21240
ctatccaaca tatttttttc aatgggtgga attggaaaaa gggctttttg cctgggatgg  21300
aagtttacta agcaataccc cgctaagaga agtaatagac gcatcgcccg caaaggacaa  21360
aagaatcttt cttgtcgaga actatcctaa aaatattgaa aagcttccgt caaacctaca  21420
ggaagtcaag catagggcaa gagacataat gttcagcgac aagaccgtcc acagtataca  21480
catgtccaaa gcaattaccc ttcaacttaa gcttattgat gatctgtata aaatgctaga  21540
gtattacttt aattcagaaa aaatcgagga aaaggagaag tttgaaaaaa ttcgtgcgag  21600
atacaaaaaa gtttcagaag aacacggcgc agagattaaa ggtgtctact atataacacg  21660
ggacgagcca tccccctccc tttatgagaa tgcagacttt tcaaaaaatg caataaaggc  21720
atcgattaat gatggagaac aaaaggctga caggataata aaagaaatcc aaacgaaagg  21780
aaaacgaaaa taatgagcca gaaaacacca accaagttgc aatttcaaca accatttttt  21840
ttatttggcc tgtattcccc tttttgtcaa aatttttttg caggccaaaa tccaaaccaa  21900
aaggaaaatt cctaatgtct gcaaatttta tttgaaagtg aattatccat attaccatag  21960
agaggcaaat ccagttcgcc ataaaatcct aaacaaaaca atactttttg atccctgcca  22020
gaaaagcaac atcagctatc tcagatgtat tggactgagc gctgccatac cacgcgcaac  22080
tttgaaaaca tcgccacacc cataactctt ataccaaatt ttttaccaac agaaataaca  22140
catgaattaa aacccaagaa atcagcaata tacccatttt gcaaagtcaa ggcattttag  22200
gtaatcgtta ataacaacaa taacagatta tacagtaaga tcattttggc aggcctaaaa  22260
aaagaccgtt ttatttaaga aaaaagcaat tctcgttatg tgggtattat cattgacgat  22320
taaccaaatt aaatcaggtc aaatcaggtc aatgactttg cctatttgat aaggtgataa  22380
taccttaggc caaacaatca gcaatatcga ttgtttttttg cattaattat ctattttttta  22440
tatttctttt aaaaaacgaa tagaaataat caaatatgtc caaactaaaa tcaagaatta  22500
gaaaaatccg tgacagttat ataatatgtt aataataatc aactaatgac aagttcaagt  22560
gaaaatagta gtgataaaga atttgaagag ggcgcagcag gcacaaataa agatagaaaa  22620
agtgatccat tgaaagagta tgaaagtaaa gagccaatga caccagcaaa aataaatgaa  22680
ggagaaccaa cggctgtaaa gagagaccca tcagaccaaa agataacagg agaaggtcaa  22740
acaggagcag ataccgaaca agcagatgaa caattgcgta aacgtggcat gaccaaaatc  22800
gattctgatt cttctaacac atctcaataa tcaaaaccaa aataaaaaga ataggatact  22860
tcatatcaat atctttattt tttcttttgt gacgcctttc acccggcaca aattcattat  22920
aaactaatcc aaatgcttcg tttcttgatt gtccaatagc aataaacagc gattagcaaa  22980
ccaaacatca acggcatcaa acatcaaaga aataaaaagg tgtgaaaaaa tacataacga  23040
cttgtcgtta tacgaaaatg aaaatatgta ttaaatctct tccataacta gatggaaatc  23100
taattttacc ttcaccgata cccattgata agaatcatat ttttctttgc gcattgttat  23160
tattgtgcat agattgatag aaatttacga cgttaaatat ccaggaggtt gctatatggt  23220
caatttttga atttgaaata ccatgtgctt tatataaaat atttcacgat atatttaaaa  23280
attacaaaaa aacatcgttt gctcgtcatt aaaaacgcaa aaaaacgggc aaaaaaaata  23340
```

-continued

```
ttatatgcat tatatataga atattgtccc tatagtgttt acaatgatac ataatcttaa  23400
attaacaaca acccttattg ctttgcttat tgttccaata attccaatga tgaccctggg  23460
aataattcca gatgtgattg cacaacagaa cacgacagga attgcagact tgactgaaag  23520
caatggcgtt ccagatgctg ccgttggcgg cagtagtggc accaacagta gcataggtgg  23580
taacactagt ggctcaagtg aaactatgag tggtaataac ggtggcgaag gcaccgtaga  23640
caaatttcaa tgaggcattt tgccacccct caactttatt aacggccaac cttgccgtct  23700
ataagtgatt tgtgacacct tttccttttt attattgtta ccttagttga tatcgaaaag  23760
agactgtatc caaccattta aaatatttgg ttattatggc gggttcaggc cctaaaaaag  23820
gaactgcagg caaatagggt tggcctgatg ccactttttt tggtttgcct caataccaca  23880
tctattattt caactccaca aaaacattta cagggatgcc atttgctctc agtccaatcc  23940
taatccttcc ctgctcatat tcaatgtccc caatactatc ttttaatccc cttgaagcaa  24000
aatgtaaacg attacttttt agctttacct tatatgttcc cgtttttttca ttatgggctg  24060
cagacacaaa ctgtatattt tctccgtcaa ccaactcata aagctcccta caaacaggtt  24120
tgattacctc ccatgtttct ttatctgtta aatccttgtc caataccata aacgggtgct  24180
tcctattttt attgtttaga tatatttgat tatgatatgc agtaaagtat atttctttga  24240
caaatttaaa atcgatttgc tctatttggg taaattataa aatcatacca acaataagga  24300
ttttcacaga tgatttgatt ttcacggtga atctgcccag agggatttca aaaggattgc  24360
cagcttatag ttttgtttaa acatttatgt atttaagtag gcataatcag ttagttactg  24420
tggtttcata cacctaaatt tttgccatat tgtattaaca aaattacggt aaaaaaatac  24480
cacgcaataa atcacttaaa atgtaatacc tactttccta tattgccttt ttcaaaacgc  24540
atttaactcg ttattgagaa ctattaatgt tgaatccaaa tggaacttaa cgcagcagta  24600
attgtgaaac tcgagccgga tttttctgaa gggaatgtaa gctataattc agacggaaca  24660
cttaacagag cagaaacaaa aaacattttg gggccccata gcgcagcagc atccctagca  24720
gccctgtact caaaagtaaa acatggaacg catgtttctg tgggcacaat gggtcctcca  24780
atagcagaat cggccttaca gcaatctcaa ctgatttgcg acgctgatga actgcatctt  24840
tatagtgatc gcatctttgc aggagccgac accctggcca cagctgaagt tttgatagca  24900
ggaataaaaa aaatggcaaa tggtcaagat gtggacattg ttttctcagg gcacagggca  24960
tctgatggcg aaacagggca aacaggaccc cagacagcat ggaaattagg ttatccgttc  25020
cttggaaatg ttattgatta cgatattgac gttgtgaaga gaattgtaag ggtacaacgt  25080
ctaatcaaga tttacggtca tcctgatatt atagaggaga tggaggcgcc tctaccggtt  25140
tttatcacac tggacccatc ctacaatccg tcttttaaca cggtatccca aaggctcaga  25200
ctagcacgaa acctacagga agcccatgat agatcacaaa ggtataagga atatctcaaa  25260
actttcaatg ccatggaact agaagtcaat ccaaagtctg tcggactgcc tggctctccc  25320
accatagttt ataaagttga aaaaatacca agggcaaagg caaatagaaa agcagatgtt  25380
gtggatgggt ctaaccagga tagtctaagg caggttgcac gccgaatcca tgatgtttta  25440
gggggtgtag tcataaagtg acatcatcac tatctgccat acctgacgct aaactagacg  25500
aaaggccaaa ccaaaatgcc catgttaatg acaacccaga aaaagaaagg ggagacaaca  25560
acaggcatct gtatgttgtg atagaacaag aggaaggcac catattacct gtgagttttg  25620
aaatgcttgg tgaggcaaga aggctaatgg atgattttaa tcacaaatac aagccagagg  25680
aaaaagtggt tgcgattata ctcggccata acatcaagca cctgtgccag gaactaatcc  25740
```

-continued

```
accatggtgc agacgcagtg atttatgccg accacccgga gctccgccac ccaagaaatc  25800
ttctttatac aaaggttgtc tgccaaattg ctacggacaa agagagcgcc gccagaattt  25860
ggccatcaaa tcccgatttt aacagacccc gttacatgtt tttttccgca gatgacacag  25920
gaaggcattt atcatcaacc gttttggcag aattgcaatc agggctggca tcagacataa  25980
acaaacttgt tatcaatgat ttagaaataa ggcatgaaca caagacaaag ggtaaaccca  26040
ttgtctatga aaagacactt gaaatgtaca gaccagactt ttcaggcttt ctttggacca  26100
ccatactctg cttggataat ataaatcccg agaacagaag gaaattccat ccacaggcat  26160
gcagtataat cccaggcgtc tttccccaaa tggaaggaga tacggataga aagggtacca  26220
taatagagtt cagcccaacc atagcccagg aagaccttag aataaaaata atcaacagaa  26280
gagtaatcaa aagcaaagtc gattttagca ataaaaaaat aatcgttagt tttggaaggg  26340
gaataaagga gtctcccgaa caaaacataa aactgataga gaaccttgca aaggaaatag  26400
aagcagaaat aggaatatca ctgcccattt caaagaaacc ctatccaata agcgaaagtc  26460
tgtcgtcaac ctatatgatt cctgacaggg ttatcggcac aagcggaaga aaggtaaatc  26520
ctcaggtgta ttttgcaata ggaataagcg gggctgtcca acacatagcc gggatgaaag  26580
aatcggaatt tgtgatttcc atcaatccag acagtgaagc tcccataata gatgaatccg  26640
atgttttaat caaaggaaaa atcgagcagg tgctgcctct cctgataaat gaattaaaaa  26700
aatacaaaga gagactgcaa ataccacagg agatagaatg acaatggaaa gttttgatgt  26760
ggcgataatt ggtggagggt ctgctggact tgcggcactt gagcacctct ccaatttggg  26820
aaaacaggca atcctcatag aggcaggaaa aaaaatagga accaaaaacg tgtctggggg  26880
catattgtat tccaaaaaaa cagcaactgg aaaggtccac aatgtagaag atgtgtttga  26940
taattttctg gcagacgctc cgctggaaag gaagataata aaatacatgc ttcacgccgt  27000
ctcaagggaa aaagcgttct ctctggacct gactttggca cacgactatc aaacgaattt  27060
tgggtacacc gtcctgctca acaaactact ttcatggttt gcaagggaag catctcaaag  27120
tgcagaaaaa ctgggtggag ggataataac aggtgtccat ttaaggtcga taatctggaa  27180
agatgacagt accataatta tagagacaga tgaacttgag ccgttccagg taaaggcagt  27240
cattgcagct gacggggtta actcagaggt tgcgcaaata acaggtgcca gaagcaagtt  27300
cacaccgtct gacctctacc agggcgtaaa ggtggtggca aaattaccag aggggttgct  27360
tgaagagaga ttcggggtct cggaaaacga gggagcggct caccttttt caggcgacat  27420
aacgctaaac cacattggag gagggttcct ttacacaaac agggacacca tctcaattgg  27480
cgcagtatac cattatgact ctctaattga aaagcctaca gagcccaatg cgctggtcaa  27540
tgcgttactg tcaaatccgt ttgtgatgga attgataaag gacgaggttc caaggatcaa  27600
ggaggactac agggatcttt caaaggatga agaactaagg attaggttca aatccaataa  27660
attgataaaa agctggaatg acctacacca cacatattat tcaccatctg ccgttgcaga  27720
gcttgtggcg cagggaaaat acaaatcaag ggaggagatc aaggacaaaa ttgattcatt  27780
gtacaatgag cttgtaacaa aatacaacac agaatttgaa acaaattacg tggagttaga  27840
gtacagcgcc aaactggttc cagatggaaa aaggtgcaga atgaaaaaac cctactttaa  27900
aaacatctta tttgtcggtg atgctgcggg caggggcatt ttccttgggc cacgcataga  27960
gggcctcaac gtaggcattg atgacgcggt tagggccgca gaagctgtct caaagtcaat  28020
agatcaaaat aactttcagt ttgacaacat tggtgaacgc tacactaaat cagtggatga  28080
```

-continued

```
aagtccatat accgcagaca tgagcaggat cgacgcaaac tatctcaaag ccgttcttga  28140
ttgcacaaaa aaggttccca aaaacactct tgggtttaag tatgggtcta ttgtcaaatt  28200
gatgtcaaat agcaccttta ggaatgtatc cataggaatt gcaaactcta tagggtacaa  28260
aaggctttta cctgtgattg agtcagacaa aacctacaat caaattccca tcgagattgc  28320
ggagagaaat ggcaaagatt tgcggaaaag ctattccata gagattccca ccattgccga  28380
gcgtattgct aatctgaact ataatgacga ttcactgtca cacatcaagg ttttgaactc  28440
gcaaagtgac tttatgaaaa aaatggtcca actgtgccct accaaatgct acagtattga  28500
gaatgagcgg ataatgctac agcacgaagg atgcatagag tgtgggacat gcgcaagaga  28560
aacagaatgg aggcatcctc gtggggaaaa aggaataatc tataattacg ggtaagccat  28620
aaccggaatc catcaacata tcctttctgg aaaaaaagtc ggggataaca cacgcaacaa  28680
aaaaaacaac gaatggattt caggttctaa atttttgggt gtttacacct tatctctgct  28740
ttcaccgctt ttattttttt tttgatggat tctatttctt caatcaactc atcaacatac  28800
tccctgattt tttcgtggct ccccgataac cctccagccc ctgcatactc agttagagaa  28860
tcagtttgtt tccggatcac tgtctgcatt ttttcatcaa gctcttcaat caactgtatg  28920
attgacggaa taagcctctc catatgattg gtaaagccac caacaattat aaagcttacg  28980
cagtgtatta atgcgtatta cagtctatat ggttataaac aaccaaacaa aatccgaatc  29040
aaaagtaaat gaataacaca taatactaca atgggccatg aaacaaatta catcaaagcg  29100
tcacatttta agcaacgtca actgctagtt ttgaaagtta tgtatttctt tagattattt  29160
tctattctat tttcattgtt gtagttggtt gttgcagcag cagttgttgc agttgccaaa  29220
ctcatggtca ttttccttca tcgttttttt ctggcatgtc ttttgtcggc atatgggaag  29280
gcagggagac aggtatgaca aatttgaatg tggcgcctat ttttccttca ctgccaaggt  29340
ggtgcagtat ttcatcaatg ccttcgtctt tatctttagt gttgttcctg ctgctgctgt  29400
tgccgccctt gctgtttgtc tcctcaaacc atatttttcc accatgctcc tcaacaattt  29460
tccttgacag gtataggcca aggccggttc cctggtttga ctttgtgaca aatttctgaa  29520
acagctgatc ccttattttg gagttgagcc caaccccggt gtcctgcact gtgactagca  29580
ccgcgccttc tttctgcctc ccgatgtggt caccaccatt gtcaccacca ccgttgtcgc  29640
tgtcgctgct gctatccact ctgcccccat tgcctttacc agctgtagca gtgtttgagg  29700
tatcactttc ctgagaggtg gaagtgaagg gagaagactc acccatcact gccgtggaaa  29760
caacaatctt gccgtcattg gtgaacttca ttgcgttgtc cagcaggttg aaaacaacct  29820
ggcttatctt ttgcggatca cagtctacat acaaaaggtg gttggggcca tttacgggtt  29880
ctacccactg ctctttttgc tgcgtctctt tttgcgcctg ttttgctcct gccgctgcct  29940
ttaccccttc tgcctttgcg ccgccgccac ctctggagta cccgccattt ctgttgccgt  30000
cagatggcaa aaacactatc gccaccttgt ttgccttctc cttgtaggcg tatttttctt  30060
caatgtcctc tatcacctgg gaaatcaggt tgtggatatc cacattttttt tggatgtcca  30120
ggctaaagct tccgctttcg attctgctca cctgcagaat gctttcggca aggttctgca  30180
gccgggacgc gtttcttgtt atcatgtcaa gctcccgctg aaactctgtt tttctttcgc  30240
caagcttctc ctccagtatc tccacaccgt ttaggatggg catgattggc gttcgcaact  30300
catgcgcagc cacgtttatg aactcgcttt tgactttgtc gttttggtca agctgctgga  30360
acaggacact ctggtcatag aggacctcaa atatggacga gtaagacaat accgttggct  30420
cgctgttgga gtagattgaa aagccgattg cggcggttgc cacctcctcc cttgcgtgta  30480
```

-continued tcagctccat caccagcgac tcctttctgt ccacaaccag tgtctttatc ttgatgccaa 30540
tgcttggcgc aatgtcctgg acttggatgt tgggcctgta ttttgtgagg agcctcaagg 30600
acaaggactc tcgcactgag gcatccatcg gcgtgaggat gttgatcctc aggctgtcgt 30660
tttgctccac catctccttc aagagttgca gtgtgccgcc tttttcctgc aggtggaacg 30720
cgttaaccgt ggagtacatt atcagtatct cccttttggc cctgcttatc atttcaaact 30780
ccctttggac cgcgtccttg tagttggaga agaccagtga gacgggcatg acaaccccat 30840
cctccagctc ctttatcctg tgctctgcgg gcaacgccct gccccaaaag ctgtcaaaca 30900
caaactgctg ctgctctgca atctcaggga ggttgctgaa caaaagctgg ggtattgact 30960
gtgccgcatg aagggtggcg acagccacat actccctctg gtcggccacc tcaaagtttc 31020
ccttcagccc atccaggtgc ctaatctccg aaaacgagag catctccttg acatagccga 31080
cgttgtcctt tgttatttcg gttacatacc gcagtttaag gcccctgttt ttgaccgcgt 31140
caaccctttt ctcccttatg gcgtcaaccc ctatcatcac ggacggggcc acggagttta 31200
tgcaagagtc tatcttcaca ttggccctgt ctatgaacct caaaatggcg ttgtttgcgt 31260
tttcagggcc atagtacacc tttgtggtgg gtgcaccggc gtcaacacca ccatcattat 31320
cgttctcgtt attgttgacg tcaccaaaac cgcgtttgtg cgacaaaccg gggtttgcgt 31380
caatgtattt attttcacat acattatcat tatttgtgcc aatgtcatgg agattattat 31440
tatgtattag agaagaacct tccaaccgtt atcacgatat cctattttgt tcactatatt 31500
aatttgagct taaaacttta taaataccgt atatacggta acaggattat tattctaaaa 31560
aaacacttaa aggtacttga caaaattctg aacaaaagat cccccatatt tactaaatac 31620
caagatttct gcaaatcgat gtgatgtgat gtatgcatag taccaatatc taggcaaacg 31680
tttttggcat tagaaaggaa tacgaataga taatcaaaga atgaaatggt cgaacacaaa 31740
ccaacaccat ggctttcaca cactgtcatt attatgtgaa actttatctg gcctctaatc 31800
tttgtcagga attaaactgt tttttattgc caattctata atgatatgct ataagcagtt 31860
agattacctt ttgatggtag tggttgttcc agtagtggtt tctccagtaa tatcatgagt 31920
ttaaagaccc ggctgatggt agcgatagaa tgcttaattg catctattga ggaaagtgtt 31980
gttgaaggta caacgctcaa tactatcaat tgaggacaac agggattgag aattgttttg 32040
acaatgataa tccattcata aaaaaaattg caagataaag catatgccgc gattgttgac 32100
cccctatttt gcatgcgttc caacaaaaag ttgtcttaac tttgcagaca tttgaataaa 32160
ttaaaaagat gttgttgact ttcgtttatt gattgattaa gattacggtt ttattttacc 32220
aaggatttaa gcattacttg cctacacgaa attaaattgc gagcaggaaa acaggaatgt 32280
gtttacataa taagaatata cccctaacca agtctttttc ctatcgcatt tttttttggt 32340
tacgccaggg cgaagaatat acttttggta acaatgattg gtaaaccctt taaccttgct 32400
tttgcgtgaa ttgtcataat tgatgttcgt aaagataaaa gcaataaaaa gaaatagtca 32460
ttatgtagaa taacacattt tttttataac ccgttataat ttaattgcaa agcagtcatc 32520
tttctaaaat aatcacaatt tgcagaatgc cgtcacttca tcttgttgca tatggtttaa 32580
ttttggatat tttcgaaagc ccaatcacaa ggttaaacgg tagaacaagt cacttgatta 32640
ttaaaatata tccacatatg gataacaata caaggatgag ttctttagca atcgagtttt 32700
ttttatccct tttttcaata acgttacttt ctaaaagaat ataccaacca gtgaaatcaa 32760
agtcatatac ctaccatgac aagcatccat ttcagtacaa gatggaggat tatgcaaacc 32820

-continued

```
acaacaaaat tgtagactat aaaaactgct tacttttttt tcaagtatcg atgttacaaa  32880

aaaataaaat aattaggatt cgggttccag gtttgtttta tacaggtggc tggatttccc  32940

tcacactaaa gtttttgata tccacatcat ttgcaccatc ccacctgaaa gtagcaatgg  33000

ggcctcccca ggatataatc tgatccggct caccaccaca ctcttcacca tcatttccaa  33060

acccacctga gtcagtgaat gtgtatacct tttgccaatt gttcttcaga gtcgggctat  33120

ccgggtttct gtctacccat atttcagtgg tgactacggt ctcaccacca gccaattggt  33180

ggttatagat catggcttta aatccaatga atctatcaaa actagacgcc gaaggtgagg  33240

gtgtggtagt gcttgaaaac acataggaga catgccactg ctcttttgca agcctaaccc  33300

ttccatcata gaatagatct gctttatatg ctgagccctc gcatccttcg ccatcatagt  33360

gcctaccacc cctgtcatac caagcgaaat tttcagaatc atctccacta ttaaccctta  33420

caatacccgt catttccaca ttcttccaat catttggata ctgcatgtat ccttgtgttg  33480

cgagtaccga gtgatcgtaa gtctcaatat cctctggatg gtaccctgat gatgtaaaca  33540

cgttatatct gacctgatcg tcattaacgt tccaactgcc atctgggttt aggtccatgt  33600

caggtgggtt tgttcgtgga tcattgttcg ggttttgcat attcataaac catttttctc  33660

caccacccgc cttatcgggg taaatctggg ttatcccaaa ctggtctaat gtccctccgc  33720

ctccagaagg ggcaacagag aacgtccata ccttgtcggc agccaatggg acaccagtcg  33780

catccgtagc accggttgtt attctggcag tgtatgtggc accaggtgtt aaatctgcag  33840

aggggtttag ggtcgcaact gtgttggttg gtgaattcat gcttacggtt gcgggcacag  33900

gtgcgcctcc gcttgttagc agtgt                                        33925
```

```
<210> SEQ ID NO 2
<211> LENGTH: 2367
<212> TYPE: DNA
<213> ORGANISM: Crenarchaeote

<400> SEQUENCE: 2
```

```
atggtgataa aatccgactt gcctctggag gagaaaaata gttattatca aaaagaactt     60

ccagaaaata ttccatcatt gttactttct tccgtttaca taggagaaaa aaaatcagtg    120

tttttgaagt tttacaatcc agaagattct caaatatatt tttggagcga gtcttttatt    180

gaaaatcata taaataaaca tcaaccttat tgctttgtaa aggaactcta ttctgatcag    240

gttaaaacaa tagttagcaa agagccacat aggtttagac tagaaaaaat aaaaaaaatg    300

gacgatattg aggacaagga aatatcggtt tttaaaataa ttgcccctga ccccctttcc    360

attggtggaa cagatagtag ttttagggaa aaggttactt cttgggaggc tgatatcaaa    420

taccatgaaa gttatttatt cgatttgggt ctaattccgg gagcgtttta taacagaata    480

ggcaataatt tagtttttca tgaattccca atgccagaga aagttgacga atatctggat    540

aatctcataa aacctaattt taaagaaaat gagccaaaaa gtagtgaata taatgagttt    600

ctaataaagt ggtcaagatt gttaaaccag cctattccgg atatcaaaag aatttctttg    660

gatatagaag tggactctga agagggaagg atgcccacag ccagagatca cgataaagta    720

attactgcag tgggtttatc ggcatcggat ggatttagaa aggtattcgt cttaagaaaa    780

gatccaaatt ttgatccctc taaactagat tcaacaaccg ttgaattatg tgatagcgaa    840

aaagacatga tactaaaagt ttttgctatt attcaaaatt atccaatagt tttaaccttt    900

aatggtgatg attttgattt accttattta tatgctagat ctcaagaccc atcgatagac    960

cctgtacaca aaaaacccat tagtaaagaa ttggtgccta ttttagttaa aaaagactct   1020
```

-continued

```
tttataaaaa ggggtattca ggcggatccg gtttccttaa agcatggaat ccatatcgat   1080

ttattcagga catttcaaaa taaatctgta cagaattatg cttttagtca taaatactct   1140

gagtttactt taaatgctat ctgcgaagcc ctattaaacg agtcaaaaat agactttgat   1200

gaaagcatag gtgatcttcc attggaaaaa ctggccgagt attgcctcaa agatgcagac   1260

ttgacatttc gtctgacatc tttcaatgac aatttactga taaaattgtt gattatcatt   1320

tctaggatat cccgaatgtc aatagaagat ataacaagat tcggggtgaa tcaatggatt   1380

aggtccatga tgttttttga acataggcag caaaatatca ttattccccg taaagatgaa   1440

ttacagaaaa aaggaacatc gtctacagtt gccattataa aggaaaaaaa atatcgagga   1500

ggtctggtgg ttgagcccgt tttaggaatt catttcaatg tcatagttgt agattttgct   1560

agtctgtatc ctagcataat taaagttcac aatttatctt acgaaacagt caattgtcct   1620

catgaaaatt gcagaaggga tccatcaaca catattgagc aaacaaacca ttgggtttgc   1680

aaggaaaagc aagggatgac ctccatattg ataggaaccc taagggatct aagggttaat   1740

tattacaaat atctatcaaa ggataattct ttggataaag aggataaaca gctatacagt   1800

gttatcagtc aggccataaa ggttatttta aatgctacgt atggggttat gggtgctgaa   1860

atatttccgc tctattgttt acctgtagct gaggctaccg cagcggttgg aaggatgacc   1920

acaacaaaaa ctattgaaaa atgcaacgaa gaaaagattg aggttattta cggtgatacg   1980

gattctctgt tcctaaagaa tccttccaag gaaggattaa gtggaatttc atcctggtct   2040

aaaaaagaac taggcataga tttggagata gataaaagat atcgctacgt ggtttttagt   2100

gaactaaaaa aaaattacct aggtgtattg gaggacggaa ctgtagatgt taaaggatta   2160

acagggaaga agtctcatac acctccaata ataagacaag ctttctatga catattaaat   2220

gtccttaaag aaatatttc agaaaaagac tttgaaagag caaaggaaaa gataaaaaaa   2280

atagtgcaat caattgcaga aaacttggag aaaaaaagaa tttctctgga agaattaagt   2340

tttaatgtta tgatcaacaa ggctgtg                                        2367
```

<210> SEQ ID NO 3
<211> LENGTH: 789
<212> TYPE: PRT
<213> ORGANISM: Crenarchaeote

<400> SEQUENCE: 3

```
Met Val Ile Lys Ser Asp Leu Pro Leu Glu Glu Lys Asn Ser Tyr Tyr
1               5                   10                  15

Gln Lys Glu Leu Pro Glu Asn Ile Pro Ser Leu Leu Leu Ser Ser Val
            20                  25                  30

Tyr Ile Gly Glu Lys Lys Ser Val Phe Leu Lys Phe Tyr Asn Pro Glu
        35                  40                  45

Asp Ser Gln Ile Tyr Phe Trp Ser Glu Ser Phe Ile Glu Asn His Ile
    50                  55                  60

Asn Lys His Gln Pro Tyr Cys Phe Val Lys Glu Leu Tyr Ser Asp Gln
65                  70                  75                  80

Val Lys Thr Ile Val Ser Lys Glu Pro His Arg Phe Arg Leu Glu Lys
                85                  90                  95

Ile Lys Lys Met Asp Asp Ile Glu Asp Lys Glu Ile Ser Val Phe Lys
            100                 105                 110

Ile Ile Ala Pro Asp Pro Leu Ser Ile Gly Gly Thr Asp Ser Ser Phe
        115                 120                 125
```

-continued

```
Arg Glu Lys Val Thr Ser Trp Glu Ala Asp Ile Lys Tyr His Glu Ser
    130                 135                 140

Tyr Leu Phe Asp Leu Gly Leu Ile Pro Gly Ala Phe Tyr Asn Arg Ile
145                 150                 155                 160

Gly Asn Asn Leu Val Phe His Glu Phe Pro Met Pro Glu Lys Val Asp
                165                 170                 175

Glu Tyr Leu Asp Asn Leu Ile Lys Pro Asn Phe Lys Glu Asn Glu Pro
            180                 185                 190

Lys Ser Ser Glu Tyr Asn Glu Phe Leu Ile Lys Trp Ser Arg Leu Leu
        195                 200                 205

Asn Gln Pro Ile Pro Asp Ile Lys Arg Ile Ser Leu Asp Ile Glu Val
    210                 215                 220

Asp Ser Glu Glu Gly Arg Met Pro Thr Ala Arg Asp His Asp Lys Val
225                 230                 235                 240

Ile Thr Ala Val Gly Leu Ser Ala Ser Asp Gly Phe Arg Lys Val Phe
                245                 250                 255

Val Leu Arg Lys Asp Pro Asn Phe Asp Pro Ser Lys Leu Asp Ser Thr
            260                 265                 270

Thr Val Glu Leu Cys Asp Ser Glu Lys Asp Met Ile Leu Lys Val Phe
        275                 280                 285

Ala Ile Ile Gln Asn Tyr Pro Ile Val Leu Thr Phe Asn Gly Asp Asp
    290                 295                 300

Phe Asp Leu Pro Tyr Leu Tyr Ala Arg Ser Gln Asp Pro Ser Ile Asp
305                 310                 315                 320

Pro Val His Lys Lys Pro Ile Ser Lys Glu Leu Val Pro Ile Leu Val
                325                 330                 335

Lys Lys Asp Ser Phe Ile Lys Arg Gly Ile Gln Ala Asp Pro Val Ser
            340                 345                 350

Leu Lys His Gly Ile His Ile Asp Leu Phe Arg Thr Phe Gln Asn Lys
        355                 360                 365

Ser Val Gln Asn Tyr Ala Phe Ser His Lys Tyr Ser Glu Phe Thr Leu
    370                 375                 380

Asn Ala Ile Cys Glu Ala Leu Leu Asn Glu Ser Lys Ile Asp Phe Asp
385                 390                 395                 400

Glu Ser Ile Gly Asp Leu Pro Leu Glu Lys Leu Ala Glu Tyr Cys Leu
                405                 410                 415

Lys Asp Ala Asp Leu Thr Phe Arg Leu Thr Ser Phe Asn Asp Asn Leu
            420                 425                 430

Leu Ile Lys Leu Leu Ile Ile Ile Ser Arg Ile Ser Arg Met Ser Ile
        435                 440                 445

Glu Asp Ile Thr Arg Phe Gly Val Asn Gln Trp Ile Arg Ser Met Met
    450                 455                 460

Phe Phe Glu His Arg Gln Gln Asn Ile Ile Ile Pro Arg Lys Asp Glu
465                 470                 475                 480

Leu Gln Lys Lys Gly Thr Ser Ser Thr Val Ala Ile Ile Lys Glu Lys
                485                 490                 495

Lys Tyr Arg Gly Gly Leu Val Val Glu Pro Val Leu Gly Ile His Phe
            500                 505                 510

Asn Val Ile Val Val Asp Phe Ala Ser Leu Tyr Pro Ser Ile Ile Lys
        515                 520                 525

Val His Asn Leu Ser Tyr Glu Thr Val Asn Cys Pro His Glu Asn Cys
    530                 535                 540

Arg Arg Asp Pro Ser Thr His Ile Glu Gln Thr Asn His Trp Val Cys
```

-continued

```
545                 550                 555                 560

Lys Glu Lys Gln Gly Met Thr Ser Ile Leu Ile Gly Thr Leu Arg Asp
                565                 570                 575

Leu Arg Val Asn Tyr Tyr Lys Tyr Leu Ser Lys Asp Asn Ser Leu Asp
            580                 585                 590

Lys Glu Asp Lys Gln Leu Tyr Ser Val Ile Ser Gln Ala Ile Lys Val
        595                 600                 605

Ile Leu Asn Ala Thr Tyr Gly Val Met Gly Ala Glu Ile Phe Pro Leu
    610                 615                 620

Tyr Cys Leu Pro Val Ala Glu Ala Thr Ala Ala Val Gly Arg Met Thr
625                 630                 635                 640

Thr Thr Lys Thr Ile Glu Lys Cys Asn Glu Glu Lys Ile Glu Val Ile
                645                 650                 655

Tyr Gly Asp Thr Asp Ser Leu Phe Leu Lys Asn Pro Ser Lys Glu Gly
            660                 665                 670

Leu Ser Gly Ile Ser Ser Trp Ser Lys Lys Glu Leu Gly Ile Asp Leu
        675                 680                 685

Glu Ile Asp Lys Arg Tyr Arg Tyr Val Val Phe Ser Glu Leu Lys Lys
    690                 695                 700

Asn Tyr Leu Gly Val Leu Glu Asp Gly Thr Val Asp Val Lys Gly Leu
705                 710                 715                 720

Thr Gly Lys Lys Ser His Thr Pro Pro Ile Ile Arg Gln Ala Phe Tyr
                725                 730                 735

Asp Ile Leu Asn Val Leu Lys Glu Ile Phe Ser Glu Lys Asp Phe Glu
            740                 745                 750

Arg Ala Lys Glu Lys Ile Lys Lys Ile Val Gln Ser Ile Ala Glu Asn
        755                 760                 765

Leu Glu Lys Lys Arg Ile Ser Leu Glu Glu Leu Ser Phe Asn Val Met
    770                 775                 780

Ile Asn Lys Ala Val
785


<210> SEQ ID NO 4
<211> LENGTH: 882
<212> TYPE: DNA
<213> ORGANISM: Crenarchaeote

<400> SEQUENCE: 4

atggatattg atcataaaat tttagtatat ttcatattat ctattaacaa aataattatt     60

acaatgggtt tggtttcgga tagacaaaga aacgagacaa tggattttat aaaaatactg    120

ggatataaca tcagatatat aaaaatagat caagtcaagt caaatgaaac cataattctg    180

cttcatggta taggagcttc cgcagaacga tggtcagaat tagtcccatt tttgtataat    240

tgcaatataa ttataccaga catcattggt tttggttaca gtgaaaaacc aaggatagag    300

tacaacatag atttatttgt aaagtttttg gatgaattgt ttctgaaact tgaaatcaaa    360

aaccccataa taatgggttc gtcttttggt ggtcaattga ttttagaata ttatttcagg    420

cacaaagact tttttaaaaa aatgattcta gtgtccccgg ccggtaccca agagagaccg    480

acactagcgt taaggcaata cacttactca tgtttatacc caacaagaga aaataccgaa    540

agagcattta agatgatgtc gcatttcaat cacacagtaa aagattcaat gataaaggat    600

tttattaata gaatgaagca gcccaacgca aaacactcgt ttgtttcaac acttttagca    660

ctaaggaaaa atagtgattt acaagacaac ctgagggaaa tcaaaatccc aactttagta    720
```

-continued

```
atatggggaa aagaggacaa caccattcca gtagaaaata tagagtattt caggggcatc    780

ccttttgtaa aaacatgcat aatgagtgat tgcggtcatg tgccttttgt tgaaaagcct    840

cttgagtttt ataaaatagt caaagagttt atcgactcct aa                       882


<210> SEQ ID NO 5
<211> LENGTH: 293
<212> TYPE: PRT
<213> ORGANISM: Crenarchaeote

<400> SEQUENCE: 5

Met Asp Ile Asp His Lys Ile Leu Val Tyr Phe Ile Leu Ser Ile Asn
1               5                   10                  15

Lys Ile Ile Ile Thr Met Gly Leu Val Ser Asp Arg Gln Arg Asn Glu
            20                  25                  30

Thr Met Asp Phe Ile Lys Ile Leu Gly Tyr Asn Ile Arg Tyr Ile Lys
        35                  40                  45

Ile Asp Gln Val Lys Ser Asn Glu Thr Ile Ile Leu Leu His Gly Ile
    50                  55                  60

Gly Ala Ser Ala Glu Arg Trp Ser Glu Leu Val Pro Phe Leu Tyr Asn
65                  70                  75                  80

Cys Asn Ile Ile Ile Pro Asp Ile Ile Gly Phe Gly Tyr Ser Glu Lys
                85                  90                  95

Pro Arg Ile Glu Tyr Asn Ile Asp Leu Phe Val Lys Phe Leu Asp Glu
            100                 105                 110

Leu Phe Leu Lys Leu Glu Ile Lys Asn Pro Ile Ile Met Gly Ser Ser
        115                 120                 125

Phe Gly Gly Gln Leu Ile Leu Glu Tyr Tyr Phe Arg His Lys Asp Phe
    130                 135                 140

Phe Lys Lys Met Ile Leu Val Ser Pro Ala Gly Thr Gln Glu Arg Pro
145                 150                 155                 160

Thr Leu Ala Leu Arg Gln Tyr Thr Tyr Ser Cys Leu Tyr Pro Thr Arg
                165                 170                 175

Glu Asn Thr Glu Arg Ala Phe Lys Met Met Ser His Phe Asn His Thr
            180                 185                 190

Val Lys Asp Ser Met Ile Lys Asp Phe Ile Asn Arg Met Lys Gln Pro
        195                 200                 205

Asn Ala Lys His Ser Phe Val Ser Thr Leu Leu Ala Leu Arg Lys Asn
    210                 215                 220

Ser Asp Leu Gln Asp Asn Leu Arg Glu Ile Lys Ile Pro Thr Leu Val
225                 230                 235                 240

Ile Trp Gly Lys Glu Asp Asn Thr Ile Pro Val Glu Asn Ile Glu Tyr
                245                 250                 255

Phe Arg Gly Ile Pro Phe Val Lys Thr Cys Ile Met Ser Asp Cys Gly
            260                 265                 270

His Val Pro Phe Val Glu Lys Pro Leu Glu Phe Tyr Lys Ile Val Lys
        275                 280                 285

Glu Phe Ile Asp Ser
    290


<210> SEQ ID NO 6
<211> LENGTH: 318
<212> TYPE: DNA
<213> ORGANISM: Crenarchaeote

<400> SEQUENCE: 6
```

-continued

```
ttgaatcaat ccacttctat gagtaatgag aatgaagaaa ataaagatat agattttaag      60

aaatccattg aaaaggctgc ggaattccag caggatttgt tgcgacagtt ctctacaatt     120

caatacaatg cgtttcagaa tatgttttca tctttgcaag gatttacaaa ttataatgcc     180

atgtttaaaa ccaccgtaca gacgggtggc aggatctcaa ttcccgaagc agaaagaaat     240

gctttgggga ttgaagaggg tgatctagtc caggttataa ttataccgtt gacaaggaaa     300

aagaaaaaca caagttaa                                                   318


<210> SEQ ID NO 7
<211> LENGTH: 105
<212> TYPE: PRT
<213> ORGANISM: Crenarchaeote

<400> SEQUENCE: 7

Met Asn Gln Ser Thr Ser Met Ser Asn Glu Asn Glu Glu Asn Lys Asp
1               5                   10                  15

Ile Asp Phe Lys Lys Ser Ile Glu Lys Ala Ala Glu Phe Gln Gln Asp
            20                  25                  30

Leu Leu Arg Gln Phe Ser Thr Ile Gln Tyr Asn Ala Phe Gln Asn Met
        35                  40                  45

Phe Ser Ser Leu Gln Gly Phe Thr Asn Tyr Asn Ala Met Phe Lys Thr
    50                  55                  60

Thr Val Gln Thr Gly Gly Arg Ile Ser Ile Pro Glu Ala Glu Arg Asn
65                  70                  75                  80

Ala Leu Gly Ile Glu Glu Gly Asp Leu Val Gln Val Ile Ile Ile Pro
                85                  90                  95

Leu Thr Arg Lys Lys Lys Asn Thr Ser
            100                 105


<210> SEQ ID NO 8
<211> LENGTH: 1086
<212> TYPE: DNA
<213> ORGANISM: Crenarchaeote

<400> SEQUENCE: 8

atgagaaaaa aaatgaataa ttccttaatt aattatttag tgaatgatta ttttacgttt      60

gtaagggatc ctgataacat ttcaaaatta aaagaaatca ggaaaaaatt gtcgaatata     120

gaaaacataa agactggatc aagcgaatat gaggtaataa gggaaacaac cctcttccgt     180

ttactacatt ataaacccct aaagcaacaa actttcaagt accctttgtt gattgtttat     240

gcattaataa acaaatcata tattttggat ctgcagaacg acaaaagttg gataaggaac     300

ctgctagagc agggcataaa tgtctatctg attgactgga aaccccgtc aaaactggat      360

aaatacatca ctgttgatga ttatgtcaat ttgtttattt atgagtgtgt agaatacata     420

aaaaacatag aaaacattga tcagatttca ttacaaggat attgcatggg ggtacaatg      480

tccttgatgt acacttcgct atatcaaaaa aacattaaaa atctagtcac cattgctcca     540

attgttgatg ccgagaaaga caaatccgta ataaaaaaca tggctgagca catggatatt     600

gacaaagtac tgtcctatca cgaaaacttt ccatatgaat tactgtatct ggtttatgca     660

tcactaaaac cattcaagca aggtgtaaac aaatactata atttatttaa aaactttgaa     720

gatgaaagtt ttgtacagaa ctttttaaga atagagaaat ggctgtatga cacacctcct     780

attgcggggg aaacctttag gcaatgggta aaggatatct atcagcaaaa cctttttgca     840

aaaaacaaga tgattgtggg tgaaaacaag ataaatttgt caaacattaa ggttcccgtt     900
```

-continued

```
cttaatgttg tagctgaatt tgaccacctt gtaacgtctg acagcagtag ctccctaaac    960

aacctaattt caagtcagga taaaagcctg atgaaatttc caacagggca tgtagggcta   1020

attgctagca acttttcaca gaaaaatgtt ttaccaaaaa ttggaaaatg gattcaaaca   1080

cattaa                                                              1086
```

<210> SEQ ID NO 9
<211> LENGTH: 361
<212> TYPE: PRT
<213> ORGANISM: Crenarchaeote

<400> SEQUENCE: 9

```
Met Arg Lys Lys Met Asn Asn Ser Leu Ile Asn Tyr Leu Val Asn Asp
1               5                   10                  15

Tyr Phe Thr Phe Val Arg Asp Pro Asp Asn Ile Ser Lys Leu Lys Glu
            20                  25                  30

Ile Arg Lys Lys Leu Ser Asn Ile Glu Asn Ile Lys Thr Gly Ser Ser
        35                  40                  45

Glu Tyr Glu Val Ile Arg Glu Thr Thr Leu Phe Arg Leu Leu His Tyr
    50                  55                  60

Lys Pro Leu Lys Gln Gln Thr Phe Lys Tyr Pro Leu Leu Ile Val Tyr
65                  70                  75                  80

Ala Leu Ile Asn Lys Ser Tyr Ile Leu Asp Leu Gln Asn Asp Lys Ser
                85                  90                  95

Trp Ile Arg Asn Leu Leu Glu Gln Gly Ile Asn Val Tyr Leu Ile Asp
            100                 105                 110

Trp Lys Pro Pro Ser Lys Leu Asp Lys Tyr Ile Thr Val Asp Asp Tyr
        115                 120                 125

Val Asn Leu Phe Ile Tyr Glu Cys Val Glu Tyr Ile Lys Asn Ile Glu
    130                 135                 140

Asn Ile Asp Gln Ile Ser Leu Gln Gly Tyr Cys Met Gly Gly Thr Met
145                 150                 155                 160

Ser Leu Met Tyr Thr Ser Leu Tyr Gln Lys Asn Ile Lys Asn Leu Val
                165                 170                 175

Thr Ile Ala Pro Ile Val Asp Ala Glu Lys Asp Lys Ser Val Ile Lys
            180                 185                 190

Asn Met Ala Glu His Met Asp Ile Asp Lys Val Leu Ser Tyr His Glu
        195                 200                 205

Asn Phe Pro Tyr Glu Leu Leu Tyr Leu Val Tyr Ala Ser Leu Lys Pro
    210                 215                 220

Phe Lys Gln Gly Val Asn Lys Tyr Tyr Asn Leu Phe Lys Asn Phe Glu
225                 230                 235                 240

Asp Glu Ser Phe Val Gln Asn Phe Leu Arg Ile Glu Lys Trp Leu Tyr
                245                 250                 255

Asp Thr Pro Pro Ile Ala Gly Glu Thr Phe Arg Gln Trp Val Lys Asp
            260                 265                 270

Ile Tyr Gln Gln Asn Leu Phe Ala Lys Asn Lys Met Ile Val Gly Glu
        275                 280                 285

Asn Lys Ile Asn Leu Ser Asn Ile Lys Val Pro Val Leu Asn Val Val
    290                 295                 300

Ala Glu Phe Asp His Leu Val Thr Ser Asp Ser Ser Ser Ser Leu Asn
305                 310                 315                 320

Asn Leu Ile Ser Ser Gln Asp Lys Ser Leu Met Lys Phe Pro Thr Gly
                325                 330                 335
```

-continued

```
His Val Gly Leu Ile Ala Ser Asn Phe Ser Gln Lys Asn Val Leu Pro
            340                 345                 350

Lys Ile Gly Lys Trp Ile Gln Thr His
        355                 360


<210> SEQ ID NO 10
<211> LENGTH: 582
<212> TYPE: DNA
<213> ORGANISM: Crenarchaeote

<400> SEQUENCE: 10

ttgcaattag aaaataacaa tattggagag gaaaaaaaca gtaaaaacac tctatctgaa      60

gaggcaggac ttcagtctgt atttgaaaac tttataaaac aattaacaga gttaaatagc     120

cttacaacct tggggccatt cacctcttta atgaatgatc caaaccttaa tttaaataca     180

ttaaaggaac acggtaattt gttactgaga tatcagtcat ttctcaacct atacttttcc     240

cgtatgataa atgcttattt gttggccgta aacaaggtat cgtctgctat agatgaaaaa     300

aaccccgacg atattaggaa aataatcata aatacttttg aggatgtgtt ctcgtcaatg     360

ttgcagtcaa cagacttttc aatcaattat aacaatttat tgaattccag cattgatgtc     420

atcaaaagtt atcaaaaaat ttacgattca aatgccgttt tgtttaggtc acaacaacaa     480

ctgtcaaaag aagaaaaaga cctgttattt tataatctct atgaaatcaa aaaaatatca     540

ttggaaatca aaaaaaaatt aaatgagaaa aaaaatgaat aa                        582


<210> SEQ ID NO 11
<211> LENGTH: 193
<212> TYPE: PRT
<213> ORGANISM: Crenarchaeote

<400> SEQUENCE: 11

Met Gln Leu Glu Asn Asn Asn Ile Gly Glu Glu Lys Asn Ser Lys Asn
1               5                   10                  15

Thr Leu Ser Glu Glu Ala Gly Leu Gln Ser Val Phe Glu Asn Phe Ile
            20                  25                  30

Lys Gln Leu Thr Glu Leu Asn Ser Leu Thr Thr Leu Gly Pro Phe Thr
        35                  40                  45

Ser Leu Met Asn Asp Pro Asn Leu Asn Leu Asn Thr Leu Lys Glu His
    50                  55                  60

Gly Asn Leu Leu Leu Arg Tyr Gln Ser Phe Leu Asn Leu Tyr Phe Ser
65                  70                  75                  80

Arg Met Ile Asn Ala Tyr Leu Leu Ala Val Asn Lys Val Ser Ser Ala
                85                  90                  95

Ile Asp Glu Lys Asn Pro Asp Asp Ile Arg Lys Ile Ile Ile Asn Thr
            100                 105                 110

Phe Glu Asp Val Phe Ser Ser Met Leu Gln Ser Thr Asp Phe Ser Ile
        115                 120                 125

Asn Tyr Asn Asn Leu Leu Asn Ser Ser Ile Asp Val Ile Lys Ser Tyr
    130                 135                 140

Gln Lys Ile Tyr Asp Ser Asn Ala Val Leu Phe Arg Ser Gln Gln Gln
145                 150                 155                 160

Leu Ser Lys Glu Glu Lys Asp Leu Leu Phe Tyr Asn Leu Tyr Glu Ile
                165                 170                 175

Lys Lys Ile Ser Leu Glu Ile Lys Lys Lys Leu Asn Glu Lys Lys Asn
            180                 185                 190

Glu
```

<210> SEQ ID NO 12
<211> LENGTH: 438
<212> TYPE: DNA
<213> ORGANISM: Crenarchaeote

<400> SEQUENCE: 12
atgcctacaa gttcagatgt tttatacatg tccaaaccag cggtggtatg tatacattct 60
tttgacatgg tgggcgggta tgcgcatacc caaaaactaa gatgctgtat cagcctcggg 120
aagagggtta tgtgggggac aatagaaaga atccatccac aaacgaatgg ttttggcaaa 180
tgtctgcctt ggctcattgt ttctatatat ggtttcgcca tagataatat ttgggtaatt 240
actcatgtgc ctgtatacaa aaatagacaa ccatctctac ctatatataa attttttgac 300
aagggtcagg ttcttttct cctttttttg caaattatgc cgggccaccc agaaacaaac 360
cccgcctttg ggcccgcaat gattactggg caacccaaat ctagcgcccc acgcccagga 420
gtgcaagtga caatgtga 438

<210> SEQ ID NO 13
<211> LENGTH: 145
<212> TYPE: PRT
<213> ORGANISM: Crenarchaeote

<400> SEQUENCE: 13

Met Pro Thr Ser Ser Asp Val Leu Tyr Met Ser Lys Pro Ala Val Val
1 5 10 15

Cys Ile His Ser Phe Asp Met Val Gly Gly Tyr Ala His Thr Gln Lys
20 25 30

Leu Arg Cys Cys Ile Ser Leu Gly Lys Arg Val Met Trp Gly Thr Ile
35 40 45

Glu Arg Ile His Pro Gln Thr Asn Gly Phe Gly Lys Cys Leu Pro Trp
50 55 60

Leu Ile Val Ser Ile Tyr Gly Phe Ala Ile Asp Asn Ile Trp Val Ile
65 70 75 80

Thr His Val Pro Val Tyr Lys Asn Arg Gln Pro Ser Leu Pro Ile Tyr
85 90 95

Lys Phe Phe Asp Lys Gly Gln Val Leu Phe Leu Leu Phe Leu Gln Ile
100 105 110

Met Pro Gly His Pro Glu Thr Asn Pro Ala Phe Gly Pro Ala Met Ile
115 120 125

Thr Gly Gln Pro Lys Ser Ser Ala Pro Arg Pro Gly Val Gln Val Thr
130 135 140

Met
145

<210> SEQ ID NO 14
<211> LENGTH: 915
<212> TYPE: DNA
<213> ORGANISM: Crenarchaeote

<400> SEQUENCE: 14
ttggattctt ggggcgaatc taatattgtc ctttggctgc tacttaggct attcaagcca 60
aaaaccaaga tctttgttgt gtttcatcac catgaaccgc ggatatctat ttgcaagaac 120
tattttgaat ttctgtacaa ttatctaata caaaaggcta ctgcggtgat gcttaaggat 180
tctgatatga ttttgaccgt gagtcaagcg tcaaagcatg aactcaacac agtctatgga 240

-continued

```
atagggggtta gcaaaatcaa taatttgaag gaaacagcaa ataaaaaaac cagggaatta    300

gcaaaaaatc tgaccaacag aattgccatt gtaggaactg gaatagataa aaatatcttt    360

ttaaaggatt ccaacagagg agtaatcaac aataaaaagg acattgattt tctttgtatc    420

ggaaggatag aaaaatttca tggactggag gaaatttgga ctgcaataaa aacactcaga    480

ccagaatcta attttgtaat ggttgggcgc ataccccctg ataaggctgc aaaactacgt    540

aatgcgggta tagatcacag aggctttgtc tccgaggaag aaaagattag cctttattct    600

aaatctaaag tctttatttt tccatcatcc agagagggtt ttggcattgc tgtggctgag    660

gccttagttt cgtgtgttcc cactgttgcc tggaaactcc ccgtttttga agaactatac    720

ttaaaaaatg gtaatacaaa cataaaacta atagaatatg gagaaaccac cctgtttgca    780

gaagagtgcg taaaaatgct aaataaatat ggcataatca aaaaggcgac tgaaggaaaa    840

aaggtcagtt tccaactccc aaactggcag acagtggcaa aaaatgtaat gacaacaata    900

gaatctgtaa cctaa                                                       915
```

<210> SEQ ID NO 15
<211> LENGTH: 304
<212> TYPE: PRT
<213> ORGANISM: Crenarchaeote

<400> SEQUENCE: 15

```
Met Asp Ser Trp Gly Glu Ser Asn Ile Val Leu Trp Leu Leu Leu Arg
1               5                   10                  15

Leu Phe Lys Pro Lys Thr Lys Ile Phe Val Val Phe His His His Glu
            20                  25                  30

Pro Arg Ile Ser Ile Cys Lys Asn Tyr Phe Glu Phe Leu Tyr Asn Tyr
        35                  40                  45

Leu Ile Gln Lys Ala Thr Ala Val Met Leu Lys Asp Ser Asp Met Ile
    50                  55                  60

Leu Thr Val Ser Gln Ala Ser Lys His Glu Leu Asn Thr Val Tyr Gly
65                  70                  75                  80

Ile Gly Val Ser Lys Ile Asn Asn Leu Lys Glu Thr Ala Asn Lys Lys
                85                  90                  95

Thr Arg Glu Leu Ala Lys Asn Leu Thr Asn Arg Ile Ala Ile Val Gly
            100                 105                 110

Thr Gly Ile Asp Lys Asn Ile Phe Leu Lys Asp Ser Asn Arg Gly Val
        115                 120                 125

Ile Asn Asn Lys Lys Asp Ile Asp Phe Leu Cys Ile Gly Arg Ile Glu
    130                 135                 140

Lys Phe His Gly Leu Glu Glu Ile Trp Thr Ala Ile Lys Thr Leu Arg
145                 150                 155                 160

Pro Glu Ser Asn Phe Val Met Val Gly Arg Ile Pro Pro Asp Lys Ala
                165                 170                 175

Ala Lys Leu Arg Asn Ala Gly Ile Asp His Arg Gly Phe Val Ser Glu
            180                 185                 190

Glu Glu Lys Ile Ser Leu Tyr Ser Lys Ser Lys Val Phe Ile Phe Pro
        195                 200                 205

Ser Ser Arg Glu Gly Phe Gly Ile Ala Val Ala Glu Ala Leu Val Ser
    210                 215                 220

Cys Val Pro Thr Val Ala Trp Lys Leu Pro Val Phe Glu Glu Leu Tyr
225                 230                 235                 240

Leu Lys Asn Gly Asn Thr Asn Ile Lys Leu Ile Glu Tyr Gly Glu Thr
                245                 250                 255
```

-continued

```
Thr Leu Phe Ala Glu Glu Cys Val Lys Met Leu Asn Lys Tyr Gly Ile
            260                 265                 270

Ile Lys Lys Ala Thr Glu Gly Lys Lys Val Ser Phe Gln Leu Pro Asn
        275                 280                 285

Trp Gln Thr Val Ala Lys Asn Val Met Thr Thr Ile Glu Ser Val Thr
    290                 295                 300


<210> SEQ ID NO 16
<211> LENGTH: 1692
<212> TYPE: DNA
<213> ORGANISM: Crenarchaeote

<400> SEQUENCE: 16

atgtgtggaa ttgttggaat tttaagtaaa aaagagagaa atgttgcccc cttgatagga     60

aaaatgctat cctgtatgaa aaaccggggt ccggatggca tgggtttgtc tacagagaat    120

caaatagttt attctgatac ctttgataat ccattgtttt cacaggtaga ggggcatgac    180

gttttaggtc acagtcgttt ggcaatagtt ggtggctcct gtggtcagca gccgtttgtg    240

agttgtgata aaaaactcat tctggagcat aatggtgaaa tatataacta taaagaaatc    300

agaaagaacc tttctgcaca tcacactttt actacctcga ctgatagtga agttattgtt    360

caccttcttg aagaccatta tcaaaacact aaaggcgatc taatcgaagc tataaggaga    420

accgttaccc agcttgatgg aatttatgtt ttggcgatta gagagcagtc cacaggagat    480

attgtgctgg tacgggatgg cattggagta agacaaattt actatggtga aagtagtgat    540

ttcattgcat ttgcatcaga aagaaaagcc ttatggaaaa ttgctatgtc cgaccaaatc    600

aaaagacttt tgccaggcta tgctcttgtc atttcgcgga aggaagggtc ctccaatttc    660

aagactacat tgtttccgat ttctgtaaat acaaaaaaat caatatgtga gaaatattca    720

atcctgtaca cagacatcga ttctgcggtt aacgcatatg gtgatacatt ggttgaatct    780

atgagaaaac gtgtgagtga ctttaaaaaa atcggtattg ttttctccgg tgggattgac    840

agtgtaattg tagcgtattt ggcaaaacaa atggcccccg aagttatttg ctatacgtct    900

gggattaaag gttcaagtga tatcctcaac tcacttgaga tagcagaaaa acttgacctc    960

aagttggaaa tagaacagat gactgaaagt gatgttgaaa gtaccattcc aaaaataatc   1020

agcataattg aagatgacaa catgggacag gttgaggttg ccattccaat atatggcgcg   1080

gttaaattgg ctcacgaaca gggaatacgg gtaatgctta caggtcaggg ggcagacgaa   1140

ctgtttggcg gatattcctg gtattccaaa attgttaaaa aacacggata cgaaaaaatt   1200

cagggatacc tgatagagga cattaagtta ctttacaaag aaacactgga aagagaggac   1260

aaaataacca tgtctcaaag catagagtta cgcgaaccct ttttagatac taatctgata   1320

gacacggtac tgagaataga tccgcgactc aatattcaaa acaatggcaa taactatgac   1380

aacctaggaa aaagggttca ccgcaaactt gcagaaaaac tagggattcc aaaagagata   1440

gcgtatagaa taaaggaagc agctcagcat ggttctggga tacacaacac cctcaatact   1500

ttggccatga aaaatggttt tacggaatcc aaggttaatt ctagttatct ggacaaattg   1560

aaaaaaaggg agcttatcgg cagctcacaa agatatgggc atctttttga aaaggaacaa   1620

atctggagtt tggagccgca tatacagatg tatttggaga atatttcaaa aaacatattg   1680

ccaaggaact ga                                                        1692


<210> SEQ ID NO 17
<211> LENGTH: 563
```

-continued

<212> TYPE: PRT
<213> ORGANISM: Crenarchaeote

<400> SEQUENCE: 17

```
Met Cys Gly Ile Val Gly Ile Leu Ser Lys Lys Glu Arg Asn Val Ala
1               5                   10                  15

Pro Leu Ile Gly Lys Met Leu Ser Cys Met Lys Asn Arg Gly Pro Asp
            20                  25                  30

Gly Met Gly Leu Ser Thr Glu Asn Gln Ile Val Tyr Ser Asp Thr Phe
        35                  40                  45

Asp Asn Pro Leu Phe Ser Gln Val Glu Gly His Asp Val Leu Gly His
    50                  55                  60

Ser Arg Leu Ala Ile Val Gly Gly Ser Cys Gly Gln Gln Pro Phe Val
65                  70                  75                  80

Ser Cys Asp Lys Lys Leu Ile Leu Glu His Asn Gly Glu Ile Tyr Asn
                85                  90                  95

Tyr Lys Glu Ile Arg Lys Asn Leu Ser Ala His His Thr Phe Thr Thr
            100                 105                 110

Ser Thr Asp Ser Glu Val Ile Val His Leu Leu Glu Asp His Tyr Gln
        115                 120                 125

Asn Thr Lys Gly Asp Leu Ile Glu Ala Ile Arg Arg Thr Val Thr Gln
    130                 135                 140

Leu Asp Gly Ile Tyr Val Leu Ala Ile Arg Glu Gln Ser Thr Gly Asp
145                 150                 155                 160

Ile Val Leu Val Arg Asp Gly Ile Gly Val Arg Gln Ile Tyr Tyr Gly
                165                 170                 175

Glu Ser Ser Asp Phe Ile Ala Phe Ala Ser Glu Arg Lys Ala Leu Trp
            180                 185                 190

Lys Ile Ala Met Ser Asp Gln Ile Lys Arg Leu Leu Pro Gly Tyr Ala
        195                 200                 205

Leu Val Ile Ser Arg Lys Glu Gly Ser Ser Asn Phe Lys Thr Thr Leu
    210                 215                 220

Phe Pro Ile Ser Val Asn Thr Lys Lys Ser Ile Cys Glu Lys Tyr Ser
225                 230                 235                 240

Ile Leu Tyr Thr Asp Ile Asp Ser Ala Val Asn Ala Tyr Gly Asp Thr
                245                 250                 255

Leu Val Glu Ser Met Arg Lys Arg Val Ser Asp Phe Lys Lys Ile Gly
            260                 265                 270

Ile Val Phe Ser Gly Gly Ile Asp Ser Val Ile Val Ala Tyr Leu Ala
        275                 280                 285

Lys Gln Met Ala Pro Glu Val Ile Cys Tyr Thr Ser Gly Ile Lys Gly
    290                 295                 300

Ser Ser Asp Ile Leu Asn Ser Leu Glu Ile Ala Glu Lys Leu Asp Leu
305                 310                 315                 320

Lys Leu Glu Ile Glu Gln Met Thr Glu Ser Asp Val Glu Ser Thr Ile
                325                 330                 335

Pro Lys Ile Ile Ser Ile Ile Glu Asp Asp Asn Met Gly Gln Val Glu
            340                 345                 350

Val Ala Ile Pro Ile Tyr Gly Ala Val Lys Leu Ala His Glu Gln Gly
        355                 360                 365

Ile Arg Val Met Leu Thr Gly Gln Gly Ala Asp Glu Leu Phe Gly Gly
    370                 375                 380

Tyr Ser Trp Tyr Ser Lys Ile Val Lys Lys His Gly Tyr Glu Lys Ile
385                 390                 395                 400
```

-continued

```
Gln Gly Tyr Leu Ile Glu Asp Ile Lys Leu Leu Tyr Lys Glu Thr Leu
                405                 410                 415

Glu Arg Glu Asp Lys Ile Thr Met Ser Gln Ser Ile Glu Leu Arg Glu
            420                 425                 430

Pro Phe Leu Asp Thr Asn Leu Ile Asp Thr Val Leu Arg Ile Asp Pro
        435                 440                 445

Arg Leu Asn Ile Gln Asn Asn Gly Asn Asn Tyr Asp Asn Leu Gly Lys
    450                 455                 460

Arg Val His Arg Lys Leu Ala Glu Lys Leu Gly Ile Pro Lys Glu Ile
465                 470                 475                 480

Ala Tyr Arg Ile Lys Glu Ala Ala Gln His Gly Ser Gly Ile His Asn
                485                 490                 495

Thr Leu Asn Thr Leu Ala Met Lys Asn Gly Phe Thr Glu Ser Lys Val
            500                 505                 510

Asn Ser Ser Tyr Leu Asp Lys Leu Lys Lys Arg Glu Leu Ile Gly Ser
        515                 520                 525

Ser Gln Arg Tyr Gly His Leu Phe Glu Lys Glu Gln Ile Trp Ser Leu
    530                 535                 540

Glu Pro His Ile Gln Met Tyr Leu Glu Asn Ile Ser Lys Asn Ile Leu
545                 550                 555                 560

Pro Arg Asn
```

<210> SEQ ID NO 18
<211> LENGTH: 666
<212> TYPE: DNA
<213> ORGANISM: Crenarchaeote

<400> SEQUENCE: 18

```
ttgttgtatc ctatggaatt taaatctaca ttggccgttt ttgatatgga tgggacgcta      60

attgatggaa ggctaattga ggtattgtca aaaaagtttg gcttgtatgc tcaggtcaga     120

cacatccagt ccgacaaatc cattccaggc tatgttaaga cacagaagat agccgctgtg     180

attaggggaa tagaagaaag ggaaatagaa attgctttgg actccatccc ccctgcaaag     240

aacagccagg aggtgatatc tttgctgaag aaaaaagggt tcagaatagg gataattaca     300

gatagttaca gtgttgctgc tcaggccttg gtgaacaaac ttgatttgga cttttttat      360

gcaaatgaat tgaaggtaga caatgggata gtcaccggag aaataaatat gccgttagga     420

tgggaaaaaa tagactgttt ttgcaagaat tctgtgtgta agagatatca catggaaatc     480

catgcaaaga aaatctgtgc agacataaaa aatacaattg ctattggcga tactaaaggt     540

gacctgtgca tgataaagca ggcaggaata ggtatcgcat atatgcctaa ggataaatat     600

ataaatgaaa caataaataa ggtaaacaca ccggatatga ttggtgtcct tgattttata     660

gagtag                                                                666
```

<210> SEQ ID NO 19
<211> LENGTH: 221
<212> TYPE: PRT
<213> ORGANISM: Crenarchaeote

<400> SEQUENCE: 19

```
Met Leu Tyr Pro Met Glu Phe Lys Ser Thr Leu Ala Val Phe Asp Met
1               5                   10                  15

Asp Gly Thr Leu Ile Asp Gly Arg Leu Ile Glu Val Leu Ser Lys Lys
            20                  25                  30
```

-continued

```
Phe Gly Leu Tyr Ala Gln Val Arg His Ile Gln Ser Asp Lys Ser Ile
        35                  40                  45

Pro Gly Tyr Val Lys Thr Gln Lys Ile Ala Ala Val Ile Arg Gly Ile
    50                  55                  60

Glu Glu Arg Glu Ile Glu Ile Ala Leu Asp Ser Ile Pro Pro Ala Lys
65                  70                  75                  80

Asn Ser Gln Glu Val Ile Ser Leu Leu Lys Lys Lys Gly Phe Arg Ile
                85                  90                  95

Gly Ile Ile Thr Asp Ser Tyr Ser Val Ala Ala Gln Ala Leu Val Asn
            100                 105                 110

Lys Leu Asp Leu Asp Phe Phe Tyr Ala Asn Glu Leu Lys Val Asp Asn
        115                 120                 125

Gly Ile Val Thr Gly Glu Ile Asn Met Pro Leu Gly Trp Glu Lys Ile
    130                 135                 140

Asp Cys Phe Cys Lys Asn Ser Val Cys Lys Arg Tyr His Met Glu Ile
145                 150                 155                 160

His Ala Lys Lys Ile Cys Ala Asp Ile Lys Asn Thr Ile Ala Ile Gly
                165                 170                 175

Asp Thr Lys Gly Asp Leu Cys Met Ile Lys Gln Ala Gly Ile Gly Ile
            180                 185                 190

Ala Tyr Met Pro Lys Asp Lys Tyr Ile Asn Glu Thr Ile Asn Lys Val
        195                 200                 205

Asn Thr Pro Asp Met Ile Gly Val Leu Asp Phe Ile Glu
    210                 215                 220


<210> SEQ ID NO 20
<211> LENGTH: 1212
<212> TYPE: DNA
<213> ORGANISM: Crenarchaeote

<400> SEQUENCE: 20

atgagattag attatccacc taactatacc gagaggatag gagcagttag tatccatgcg      60

cttcaaaaga tttatgagat cgattccgga aagatgccca agtttaatgg cctgcatcag     120

catcagtcta taaaggcctt tggttatgac gaactgtcaa gcatattcca agaacttgcc     180

atagtcattc cagtaaagaa cgaaaaaatc agccttcttg aaggagtatt gagcggtatt     240

ccaaatgaat gtctcatcat catagtttcc aatagccaaa ggactcctgt cgacagattt     300

gccatggagg ttgaaatggt aaggcagtac tctagttttg cagacaagaa aataatgatt     360

attcaccaaa atgatcctga gctggctaat acttttaaga aaataaagta tagatccatc     420

ctcaacacca aaagtcaggt tcgtagtgga aaggctgaag gaatgataat tggaatattg     480

ctggcaaaaa tgcacctaaa agagtacatt ggatttattg acagtgataa ttattttcca     540

ggagcagtaa atgaatatgt caagatcttt gcagcgggat ttggaatggc aaccacccca     600

tacagcaata tcagaatatc gtggcgttcc aaacccaaaa tcgtaaacaa ctcactacaa     660

ttcccaagat ggggtagaat ttcagaatcc agtaacaaat acctgaacgc tctaatatcc     720

cacatcacag ggtttgaaag ggagattatc acgactggaa atgcaggtga gcatgcatta     780

tccatgtccc ttgcagaaaa tctcaactat tcaagcggat attcggttga gccctatgag     840

tttatcaaca ttttagaaaa gtttggaggt ctactcccat caaacaatcc tgacatcata     900

gaaaagggta tcgaaatatt tcaaatagag accaggaatc cacactttca tgaggaaaaa     960

ggaaatgatc atttggcagg catgatgcaa gaatctcttc tcgcaataaa caacagcaaa    1020

atttgcaaca cagaactgac cagggaaata aatgaccatt tactcatgct tcaggtaaaa    1080
```

-continued

```
cacaataatg atatgaccaa actcaacttt aagaaaaaac accttataat ggatcccata   1140

aaaataatac ccatcgacaa attcgccgaa tttgtagtta agaattctaa aaccttcatt   1200

agaattggat aa                                                       1212


<210> SEQ ID NO 21
<211> LENGTH: 403
<212> TYPE: PRT
<213> ORGANISM: Crenarchaeote

<400> SEQUENCE: 21

Met Arg Leu Asp Tyr Pro Pro Asn Tyr Thr Glu Arg Ile Gly Ala Val
1               5                   10                  15

Ser Ile His Ala Leu Gln Lys Ile Tyr Glu Ile Asp Ser Gly Lys Met
            20                  25                  30

Pro Lys Phe Asn Gly Leu His Gln His Gln Ser Ile Lys Ala Phe Gly
        35                  40                  45

Tyr Asp Glu Leu Ser Ser Ile Phe Gln Glu Leu Ala Ile Val Ile Pro
    50                  55                  60

Val Lys Asn Glu Lys Ile Ser Leu Leu Glu Gly Val Leu Ser Gly Ile
65                  70                  75                  80

Pro Asn Glu Cys Leu Ile Ile Ile Val Ser Asn Ser Gln Arg Thr Pro
                85                  90                  95

Val Asp Arg Phe Ala Met Glu Val Glu Met Val Arg Gln Tyr Ser Ser
            100                 105                 110

Phe Ala Asp Lys Lys Ile Met Ile Ile His Gln Asn Asp Pro Glu Leu
        115                 120                 125

Ala Asn Thr Phe Lys Lys Ile Lys Tyr Arg Ser Ile Leu Asn Thr Lys
    130                 135                 140

Ser Gln Val Arg Ser Gly Lys Ala Glu Gly Met Ile Ile Gly Ile Leu
145                 150                 155                 160

Leu Ala Lys Met His Leu Lys Glu Tyr Ile Gly Phe Ile Asp Ser Asp
                165                 170                 175

Asn Tyr Phe Pro Gly Ala Val Asn Glu Tyr Val Lys Ile Phe Ala Ala
            180                 185                 190

Gly Phe Gly Met Ala Thr Thr Pro Tyr Ser Asn Ile Arg Ile Ser Trp
        195                 200                 205

Arg Ser Lys Pro Lys Ile Val Asn Asn Ser Leu Gln Phe Pro Arg Trp
    210                 215                 220

Gly Arg Ile Ser Glu Ser Ser Asn Lys Tyr Leu Asn Ala Leu Ile Ser
225                 230                 235                 240

His Ile Thr Gly Phe Glu Arg Glu Ile Ile Thr Thr Gly Asn Ala Gly
                245                 250                 255

Glu His Ala Leu Ser Met Ser Leu Ala Glu Asn Leu Asn Tyr Ser Ser
            260                 265                 270

Gly Tyr Ser Val Glu Pro Tyr Glu Phe Ile Asn Ile Leu Glu Lys Phe
        275                 280                 285

Gly Gly Leu Leu Pro Ser Asn Asn Pro Asp Ile Ile Glu Lys Gly Ile
    290                 295                 300

Glu Ile Phe Gln Ile Glu Thr Arg Asn Pro His Phe His Glu Glu Lys
305                 310                 315                 320

Gly Asn Asp His Leu Ala Gly Met Met Gln Glu Ser Leu Leu Ala Ile
                325                 330                 335

Asn Asn Ser Lys Ile Cys Asn Thr Glu Leu Thr Arg Glu Ile Asn Asp
```

-continued

```
            340                 345                 350

His Leu Leu Met Leu Gln Val Lys His Asn Asn Asp Met Thr Lys Leu
        355                 360                 365

Asn Phe Lys Lys Lys His Leu Ile Met Asp Pro Ile Lys Ile Ile Pro
    370                 375                 380

Ile Asp Lys Phe Ala Glu Phe Val Val Lys Asn Ser Lys Thr Phe Ile
385                 390                 395                 400

Arg Ile Gly


<210> SEQ ID NO 22
<211> LENGTH: 1164
<212> TYPE: DNA
<213> ORGANISM: Crenarchaeote

<400> SEQUENCE: 22

atgagtgatg ctatcgaaaa tgtcctgatc cttcagggag gaggatcttt gggtgcattt      60

ggttgcgggg tctacaaagc actagtaaac aataacataa aacttgatat cctgtctggc     120

acatcaattg gcggtttgaa tgccacagtt attgccggca gtaaagaaga tcgtccagaa     180

aaatcattgg agaatttttg gatggaaata gctgatacta ataatggtaa tattaataca     240

taccttaatt tccccttttt tgaaagtccc tttcctgggc aaattccttt ccccttggca     300

tcagaatcaa cactatcatt ctacagctct gccatttatg gaaatagaaa aatctttctg     360

ccaagatggg gacctgaaaa tatctttaaa gatccacagt atttcacacc tagcaaatgg     420

acatatttgt atgaccattc acctttggta aaaaccttgg aaaagtacat tgattatagc     480

aaattacagc caaacggtaa gcccaacgca aggctaataa taaccgcagt taacgtgatg     540

acggcggagc cccttatttt tgacagtgcc aagcaacaaa taaccccaaa acacatactt     600

gcaaccactg cctatccaac atattttttt caatgggtgg aattggaaaa agggcttttt     660

gcctgggatg gaagtttact aagcaatacc ccgctaagag aagtaataga cgcatcgccc     720

gcaaaggaca aaagaatctt tcttgtcgag aactatccta aaaatattga aaagcttccg     780

tcaaacctac aggaagtcaa gcatagggca agagacataa tgttcagcga caagaccgtc     840

cacagtatac acatgtccaa agcaattacc cttcaactta agcttattga tgatctgtat     900

aaaatgctag agtattactt taattcagaa aaaatcgagg aaaaggagaa gtttgaaaaa     960

attcgtgcga gatacaaaaa agtttcagaa gaacacggcg cagagattaa aggtgtctac    1020

tatataacac gggacgagcc atccccctcc ctttatgaga atgcagactt ttcaaaaaat    1080

gcaataaagg catcgattaa tgatggagaa caaaaggctg acaggataat aaaagaaatc    1140

caaacgaaag gaaaacgaaa ataa                                           1164


<210> SEQ ID NO 23
<211> LENGTH: 387
<212> TYPE: PRT
<213> ORGANISM: Crenarchaeote

<400> SEQUENCE: 23

Met Ser Asp Ala Ile Glu Asn Val Leu Ile Leu Gln Gly Gly Gly Ser
1               5                   10                  15

Leu Gly Ala Phe Gly Cys Gly Val Tyr Lys Ala Leu Val Asn Asn Asn
            20                  25                  30

Ile Lys Leu Asp Ile Leu Ser Gly Thr Ser Ile Gly Gly Leu Asn Ala
        35                  40                  45

Thr Val Ile Ala Gly Ser Lys Glu Asp Arg Pro Glu Lys Ser Leu Glu
```

-continued

```
    50                  55                  60

Asn Phe Trp Met Glu Ile Ala Asp Thr Asn Asn Gly Asn Ile Asn Thr
65                  70                  75                  80

Tyr Leu Asn Phe Pro Phe Phe Glu Ser Pro Phe Pro Gly Gln Ile Pro
                85                  90                  95

Phe Pro Leu Ala Ser Glu Ser Thr Leu Ser Phe Tyr Ser Ser Ala Ile
            100                 105                 110

Tyr Gly Asn Arg Lys Ile Phe Leu Pro Arg Trp Gly Pro Glu Asn Ile
        115                 120                 125

Phe Lys Asp Pro Gln Tyr Phe Thr Pro Ser Lys Trp Thr Tyr Leu Tyr
    130                 135                 140

Asp His Ser Pro Leu Val Lys Thr Leu Glu Lys Tyr Ile Asp Tyr Ser
145                 150                 155                 160

Lys Leu Gln Pro Asn Gly Lys Pro Asn Ala Arg Leu Ile Ile Thr Ala
                165                 170                 175

Val Asn Val Met Thr Ala Glu Pro Leu Ile Phe Asp Ser Ala Lys Gln
            180                 185                 190

Gln Ile Thr Pro Lys His Ile Leu Ala Thr Thr Ala Tyr Pro Thr Tyr
        195                 200                 205

Phe Phe Gln Trp Val Glu Leu Glu Lys Gly Leu Phe Ala Trp Asp Gly
    210                 215                 220

Ser Leu Leu Ser Asn Thr Pro Leu Arg Glu Val Ile Asp Ala Ser Pro
225                 230                 235                 240

Ala Lys Asp Lys Arg Ile Phe Leu Val Glu Asn Tyr Pro Lys Asn Ile
                245                 250                 255

Glu Lys Leu Pro Ser Asn Leu Gln Glu Val Lys His Arg Ala Arg Asp
            260                 265                 270

Ile Met Phe Ser Asp Lys Thr Val His Ser Ile His Met Ser Lys Ala
        275                 280                 285

Ile Thr Leu Gln Leu Lys Leu Ile Asp Asp Leu Tyr Lys Met Leu Glu
    290                 295                 300

Tyr Tyr Phe Asn Ser Glu Lys Ile Glu Glu Lys Glu Lys Phe Glu Lys
305                 310                 315                 320

Ile Arg Ala Arg Tyr Lys Lys Val Ser Glu Glu His Gly Ala Glu Ile
                325                 330                 335

Lys Gly Val Tyr Tyr Ile Thr Arg Asp Glu Pro Ser Pro Ser Leu Tyr
            340                 345                 350

Glu Asn Ala Asp Phe Ser Lys Asn Ala Ile Lys Ala Ser Ile Asn Asp
        355                 360                 365

Gly Glu Gln Lys Ala Asp Arg Ile Ile Lys Glu Ile Gln Thr Lys Gly
    370                 375                 380

Lys Arg Lys
385
```

<210> SEQ ID NO 24
<211> LENGTH: 882
<212> TYPE: DNA
<213> ORGANISM: Crenarchaeote

<400> SEQUENCE: 24

```
atggaactta acgcagcagt aattgtgaaa ctcgagccgg atttttctga agggaatgta      60

agctataatt cagacggaac acttaacaga gcagaaacaa aaaacatttt ggggccccat     120

agcgcagcag catccctagc agccctgtac tcaaaagtaa aacatggaac gcatgtttct     180
```

-continued

```
gtgggcacaa tgggtcctcc aatagcagaa tcggccttac agcaatctca actgatttgc    240

gacgctgatg aactgcatct ttatagtgat cgcatctttg caggagccga caccctggcc    300

acagctgaag ttttgatagc aggaataaaa aaaatggcaa atggtcaaga tgtggacatt    360

gttttctcag ggcacagggc atctgatggc gaaacagggc aaacaggacc ccagacagca    420

tggaaattag gttatccgtt ccttggaaat gttattgatt acgatattga cgttgtgaag    480

agaattgtaa gggtacaacg tctaatcaag atttacggtc atcctgatat tatagaggag    540

atggaggcgc ctctaccggt ttttatcaca ctggacccat cctacaatcc gtcttttaac    600

acggtatccc aaaggctcag actagcacga aacctacagg aagcccatga tagatcacaa    660

aggtataagg aatatctcaa aactttcaat gccatggaac tagaagtcaa tccaaagtct    720

gtcggactgc ctggctctcc caccatagtt tataaagttg aaaaaatacc aagggcaaag    780

gcaaatagaa aagcagatgt tgtggatggg tctaaccagg atagtctaag gcaggttgca    840

cgccgaatcc atgatgtttt agggggtgta gtcataaagt ga                        882
```

<210> SEQ ID NO 25
<211> LENGTH: 293
<212> TYPE: PRT
<213> ORGANISM: Crenarchaeote

<400> SEQUENCE: 25

```
Met Glu Leu Asn Ala Ala Val Ile Val Lys Leu Glu Pro Asp Phe Ser
1               5                   10                  15

Glu Gly Asn Val Ser Tyr Asn Ser Asp Gly Thr Leu Asn Arg Ala Glu
            20                  25                  30

Thr Lys Asn Ile Leu Gly Pro His Ser Ala Ala Ala Ser Leu Ala Ala
        35                  40                  45

Leu Tyr Ser Lys Val Lys His Gly Thr His Val Ser Val Gly Thr Met
    50                  55                  60

Gly Pro Pro Ile Ala Glu Ser Ala Leu Gln Gln Ser Gln Leu Ile Cys
65                  70                  75                  80

Asp Ala Asp Glu Leu His Leu Tyr Ser Asp Arg Ile Phe Ala Gly Ala
                85                  90                  95

Asp Thr Leu Ala Thr Ala Glu Val Leu Ile Ala Gly Ile Lys Lys Met
            100                 105                 110

Ala Asn Gly Gln Asp Val Asp Ile Val Phe Ser Gly His Arg Ala Ser
        115                 120                 125

Asp Gly Glu Thr Gly Gln Thr Gly Pro Gln Thr Ala Trp Lys Leu Gly
    130                 135                 140

Tyr Pro Phe Leu Gly Asn Val Ile Asp Tyr Asp Ile Asp Val Val Lys
145                 150                 155                 160

Arg Ile Val Arg Val Gln Arg Leu Ile Lys Ile Tyr Gly His Pro Asp
                165                 170                 175

Ile Ile Glu Glu Met Glu Ala Pro Leu Pro Val Phe Ile Thr Leu Asp
            180                 185                 190

Pro Ser Tyr Asn Pro Ser Phe Asn Thr Val Ser Gln Arg Leu Arg Leu
        195                 200                 205

Ala Arg Asn Leu Gln Glu Ala His Asp Arg Ser Gln Arg Tyr Lys Glu
    210                 215                 220

Tyr Leu Lys Thr Phe Asn Ala Met Glu Leu Glu Val Asn Pro Lys Ser
225                 230                 235                 240

Val Gly Leu Pro Gly Ser Pro Thr Ile Val Tyr Lys Val Glu Lys Ile
                245                 250                 255
```

-continued

```
Pro Arg Ala Lys Ala Asn Arg Lys Ala Asp Val Val Asp Gly Ser Asn
            260                 265                 270

Gln Asp Ser Leu Arg Gln Val Ala Arg Arg Ile His Asp Val Leu Gly
        275                 280                 285

Gly Val Val Ile Lys
    290


<210> SEQ ID NO 26
<211> LENGTH: 1284
<212> TYPE: DNA
<213> ORGANISM: Crenarchaeote

<400> SEQUENCE: 26

gtgacatcat cactatctgc catacctgac gctaaactag acgaaaggcc aaaccaaaat      60

gcccatgtta atgacaaccc agaaaaagaa aggggagaca acaacaggca tctgtatgtt     120

gtgatagaac aagaggaagg caccatatta cctgtgagtt ttgaaatgct tggtgaggca     180

agaaggctaa tggatgattt taatcacaaa tacaagccag aggaaaaagt ggttgcgatt     240

atactcggcc ataacatcaa gcacctgtgc caggaactaa tccaccatgg tgcagacgca     300

gtgatttatg ccgaccaccc ggagctccgc cacccaagaa atcttcttta tacaaaggtt     360

gtctgccaaa ttgctacgga caaagagagc gccgccagaa tttggccatc aaatccccgat     420

tttaacagac cccgttacat gtttttttcc gcagatgaca caggaaggca tttatcatca     480

accgttttgg cagaattgca atcagggctg gcatcagaca taaacaaact tgttatcaat     540

gatttagaaa taaggcatga acacaagaca aagggtaaac ccattgtcta tgaaaagaca     600

cttgaaatgt acagaccaga cttttcaggc tttctttgga ccaccatact ctgcttggat     660

aatataaatc ccgagaacag aaggaaattc catccacagg catgcagtat aatcccaggc     720

gtctttcccc aaatggaagg agatacggat agaaagggta ccataataga gttcagccca     780

accatagccc aggaagacct tagaataaaa ataatcaaca gaagagtaat caaaagcaaa     840

gtcgatttta gcaataaaaa aataatcgtt agttttggaa ggggaataaa ggagtctccc     900

gaacaaaaca taaaactgat agagaacctt gcaaaggaaa tagaagcaga aataggaata     960

tcactgccca tttcaaagaa accctatcca ataagcgaaa gtctgtcgtc aacctatatg    1020

attcctgaca gggttatcgg cacaagcgga agaaaggtaa atcctcaggt gtattttgca    1080

ataggaataa gcggggctgt ccaacacata gccgggatga aagaatcgga atttgtgatt    1140

tccatcaatc cagacagtga agctcccata atagatgaat ccgatgtttt aatcaaagga    1200

aaaatcgagc aggtgctgcc tctcctgata aatgaattaa aaaaatacaa agagagactg    1260

caaataccac aggagataga atga                                           1284


<210> SEQ ID NO 27
<211> LENGTH: 427
<212> TYPE: PRT
<213> ORGANISM: Crenarchaeote

<400> SEQUENCE: 27

Met Thr Ser Ser Leu Ser Ala Ile Pro Asp Ala Lys Leu Asp Glu Arg
1               5                   10                  15

Pro Asn Gln Asn Ala His Val Asn Asp Asn Pro Glu Lys Glu Arg Gly
            20                  25                  30

Asp Asn Asn Arg His Leu Tyr Val Val Ile Glu Gln Glu Glu Gly Thr
        35                  40                  45
```

-continued

```
Ile Leu Pro Val Ser Phe Glu Met Leu Gly Glu Ala Arg Arg Leu Met
    50                  55                  60

Asp Asp Phe Asn His Lys Tyr Lys Pro Glu Glu Lys Val Val Ala Ile
65                  70                  75                  80

Ile Leu Gly His Asn Ile Lys His Leu Cys Gln Glu Leu Ile His His
                85                  90                  95

Gly Ala Asp Ala Val Ile Tyr Ala Asp His Pro Glu Leu Arg His Pro
            100                 105                 110

Arg Asn Leu Leu Tyr Thr Lys Val Val Cys Gln Ile Ala Thr Asp Lys
        115                 120                 125

Glu Ser Ala Ala Arg Ile Trp Pro Ser Asn Pro Asp Phe Asn Arg Pro
    130                 135                 140

Arg Tyr Met Phe Phe Ser Ala Asp Asp Thr Gly Arg His Leu Ser Ser
145                 150                 155                 160

Thr Val Leu Ala Glu Leu Gln Ser Gly Leu Ala Ser Asp Ile Asn Lys
                165                 170                 175

Leu Val Ile Asn Asp Leu Glu Ile Arg His Glu His Lys Thr Lys Gly
            180                 185                 190

Lys Pro Ile Val Tyr Glu Lys Thr Leu Glu Met Tyr Arg Pro Asp Phe
        195                 200                 205

Ser Gly Phe Leu Trp Thr Thr Ile Leu Cys Leu Asp Asn Ile Asn Pro
    210                 215                 220

Glu Asn Arg Arg Lys Phe His Pro Gln Ala Cys Ser Ile Ile Pro Gly
225                 230                 235                 240

Val Phe Pro Gln Met Glu Gly Asp Thr Asp Arg Lys Gly Thr Ile Ile
                245                 250                 255

Glu Phe Ser Pro Thr Ile Ala Gln Glu Asp Leu Arg Ile Lys Ile Ile
            260                 265                 270

Asn Arg Arg Val Ile Lys Ser Lys Val Asp Phe Ser Asn Lys Lys Ile
        275                 280                 285

Ile Val Ser Phe Gly Arg Gly Ile Lys Glu Ser Pro Glu Gln Asn Ile
    290                 295                 300

Lys Leu Ile Glu Asn Leu Ala Lys Glu Ile Glu Ala Glu Ile Gly Ile
305                 310                 315                 320

Ser Leu Pro Ile Ser Lys Lys Pro Tyr Pro Ile Ser Glu Ser Leu Ser
                325                 330                 335

Ser Thr Tyr Met Ile Pro Asp Arg Val Ile Gly Thr Ser Gly Arg Lys
            340                 345                 350

Val Asn Pro Gln Val Tyr Phe Ala Ile Gly Ile Ser Gly Ala Val Gln
        355                 360                 365

His Ile Ala Gly Met Lys Glu Ser Glu Phe Val Ile Ser Ile Asn Pro
    370                 375                 380

Asp Ser Glu Ala Pro Ile Ile Asp Glu Ser Asp Val Leu Ile Lys Gly
385                 390                 395                 400

Lys Ile Glu Gln Val Leu Pro Leu Leu Ile Asn Glu Leu Lys Lys Tyr
                405                 410                 415

Lys Glu Arg Leu Gln Ile Pro Gln Glu Ile Glu
            420                 425
```

<210> SEQ ID NO 28
<211> LENGTH: 1878
<212> TYPE: DNA
<213> ORGANISM: Crenarchaeote

<400> SEQUENCE: 28

-continued

```
atgacaatgg aaagttttga tgtggcgata attggtggag ggtctgctgg acttgcggca     60
cttgagcacc tctccaattt gggaaaacag gcaatcctca tagaggcagg aaaaaaaata    120
ggaaccaaaa acgtgtctgg gggcatattg tattccaaaa aaacagcaac tggaaaggtc    180
cacaatgtag aagatgtgtt tgataatttt ctggcagacg ctccgctgga aaggaagata    240
ataaaataca tgcttcacgc cgtctcaagg gaaaaagcgt tctctctgga cctgactttg    300
gcacacgact atcaaacgaa ttttgggtac accgtcctgc tcaacaaact actttcatgg    360
tttgcaaggg aagcatctca aagtgcagaa aaactgggtg gagggataat aacaggtgtc    420
catttaaggt cgataatctg gaaagatgac agtaccataa ttatagagac agatgaactt    480
gagccgttcc aggtaaaggc agtcattgca gctgacgggg ttaactcaga ggttgcgcaa    540
ataacaggtg ccagaagcaa gttcacaccg tctgacctct accagggcgt aaaggtggtg    600
gcaaaattac cagaggggtt gcttgaagag agattcgggg tctcggaaaa cgagggagcg    660
gctcaccttt tttcaggcga cataacgcta aaccacattg gaggagggtt cctttacaca    720
aacagggaca ccatctcaat tggcgcagta taccattatg actctctaat tgaaaagcct    780
acagagccca atgcgctggt caatgcgtta ctgtcaaatc cgtttgtgat ggaattgata    840
aaggacgagg ttccaaggat caaggaggac tacagggatc tttcaaagga tgaagaacta    900
aggattaggt tcaaatccaa taaattgata aaaagctgga atgacctaca ccacacatat    960
tattcaccat ctgccgttgc agagcttgtg gcgcagggaa aatacaaatc aagggaggag   1020
atcaaggaca aaattgattc attgtacaat gagcttgtaa caaaatacaa cacagaattt   1080
gaaacaaatt acgtggagtt agagtacagc gccaaactgg ttccagatgg aaaaaggtgc   1140
agaatgaaaa aaccctactt taaaaacatc ttatttgtcg gtgatgctgc gggcaggggc   1200
attttccttg ggccacgcat agagggcctc aacgtaggca ttgatgacgc ggttagggcc   1260
gcagaagctg tctcaaagtc aatagatcaa aataactttc agtttgacaa cattggtgaa   1320
cgctacacta aatcagtgga tgaaagtcca tataccgcag acatgagcag gatcgacgca   1380
aactatctca aagccgttct tgattgcaca aaaaaggttc ccaaaaacac tcttgggttt   1440
aagtatgggt ctattgtcaa attgatgtca aatagcacct ttaggaatgt atccatagga   1500
attgcaaact ctatagggta caaaaggctt ttacctgtga ttgagtcaga caaaacctac   1560
aatcaaattc ccatcgagat tgcggagaga aatggcaaag atttgcggaa aagctattcc   1620
atagagattc ccaccattgc cgagcgtatt gctaatctga actataatga cgattcactg   1680
tcacacatca aggttttgaa ctcgcaaagt gactttatga aaaaaatggt ccaactgtgc   1740
cctaccaaat gctacagtat tgagaatgag cggataatgc tacagcacga aggatgcata   1800
gagtgtggga catgcgcaag agaaacagaa tggaggcatc ctcgtgggga aaaaggaata   1860
atctataatt acgggtaa                                                 1878
```

<210> SEQ ID NO 29
<211> LENGTH: 625
<212> TYPE: PRT
<213> ORGANISM: Crenarchaeote

<400> SEQUENCE: 29

```
Met Thr Met Glu Ser Phe Asp Val Ala Ile Ile Gly Gly Gly Ser Ala
1               5                   10                  15

Gly Leu Ala Ala Leu Glu His Leu Ser Asn Leu Gly Lys Gln Ala Ile
            20                  25                  30
```

-continued

```
Leu Ile Glu Ala Gly Lys Lys Ile Gly Thr Lys Asn Val Ser Gly Gly
        35                  40                  45

Ile Leu Tyr Ser Lys Lys Thr Ala Thr Gly Lys Val His Asn Val Glu
    50                  55                  60

Asp Val Phe Asp Asn Phe Leu Ala Asp Ala Pro Leu Glu Arg Lys Ile
65                  70                  75                  80

Ile Lys Tyr Met Leu His Ala Val Ser Arg Glu Lys Ala Phe Ser Leu
                85                  90                  95

Asp Leu Thr Leu Ala His Asp Tyr Gln Thr Asn Phe Gly Tyr Thr Val
            100                 105                 110

Leu Leu Asn Lys Leu Leu Ser Trp Phe Ala Arg Glu Ala Ser Gln Ser
        115                 120                 125

Ala Glu Lys Leu Gly Gly Gly Ile Ile Thr Gly Val His Leu Arg Ser
    130                 135                 140

Ile Ile Trp Lys Asp Asp Ser Thr Ile Ile Ile Glu Thr Asp Glu Leu
145                 150                 155                 160

Glu Pro Phe Gln Val Lys Ala Val Ile Ala Ala Asp Gly Val Asn Ser
                165                 170                 175

Glu Val Ala Gln Ile Thr Gly Ala Arg Ser Lys Phe Thr Pro Ser Asp
            180                 185                 190

Leu Tyr Gln Gly Val Lys Val Val Ala Lys Leu Pro Glu Gly Leu Leu
        195                 200                 205

Glu Glu Arg Phe Gly Val Ser Glu Asn Glu Gly Ala Ala His Leu Phe
    210                 215                 220

Ser Gly Asp Ile Thr Leu Asn His Ile Gly Gly Gly Phe Leu Tyr Thr
225                 230                 235                 240

Asn Arg Asp Thr Ile Ser Ile Gly Ala Val Tyr His Tyr Asp Ser Leu
                245                 250                 255

Ile Glu Lys Pro Thr Glu Pro Asn Ala Leu Val Asn Ala Leu Leu Ser
            260                 265                 270

Asn Pro Phe Val Met Glu Leu Ile Lys Asp Glu Val Pro Arg Ile Lys
        275                 280                 285

Glu Asp Tyr Arg Asp Leu Ser Lys Asp Glu Glu Leu Arg Ile Arg Phe
    290                 295                 300

Lys Ser Asn Lys Leu Ile Lys Ser Trp Asn Asp Leu His His Thr Tyr
305                 310                 315                 320

Tyr Ser Pro Ser Ala Val Ala Glu Leu Val Ala Gln Gly Lys Tyr Lys
                325                 330                 335

Ser Arg Glu Glu Ile Lys Asp Lys Ile Asp Ser Leu Tyr Asn Glu Leu
            340                 345                 350

Val Thr Lys Tyr Asn Thr Glu Phe Glu Thr Asn Tyr Val Glu Leu Glu
        355                 360                 365

Tyr Ser Ala Lys Leu Val Pro Asp Gly Lys Arg Cys Arg Met Lys Lys
    370                 375                 380

Pro Tyr Phe Lys Asn Ile Leu Phe Val Gly Asp Ala Ala Gly Arg Gly
385                 390                 395                 400

Ile Phe Leu Gly Pro Arg Ile Glu Gly Leu Asn Val Gly Ile Asp Asp
                405                 410                 415

Ala Val Arg Ala Ala Glu Ala Val Ser Lys Ser Ile Asp Gln Asn Asn
            420                 425                 430

Phe Gln Phe Asp Asn Ile Gly Glu Arg Tyr Thr Lys Ser Val Asp Glu
        435                 440                 445

Ser Pro Tyr Thr Ala Asp Met Ser Arg Ile Asp Ala Asn Tyr Leu Lys
```

-continued

```
    450                 455                 460

Ala Val Leu Asp Cys Thr Lys Lys Val Pro Lys Asn Thr Leu Gly Phe
465                 470                 475                 480

Lys Tyr Gly Ser Ile Val Lys Leu Met Ser Asn Ser Thr Phe Arg Asn
                485                 490                 495

Val Ser Ile Gly Ile Ala Asn Ser Ile Gly Tyr Lys Arg Leu Leu Pro
            500                 505                 510

Val Ile Glu Ser Asp Lys Thr Tyr Asn Gln Ile Pro Ile Glu Ile Ala
        515                 520                 525

Glu Arg Asn Gly Lys Asp Leu Arg Lys Ser Tyr Ser Ile Glu Ile Pro
    530                 535                 540

Thr Ile Ala Glu Arg Ile Ala Asn Leu Asn Tyr Asn Asp Asp Ser Leu
545                 550                 555                 560

Ser His Ile Lys Val Leu Asn Ser Gln Ser Asp Phe Met Lys Lys Met
                565                 570                 575

Val Gln Leu Cys Pro Thr Lys Cys Tyr Ser Ile Glu Asn Glu Arg Ile
            580                 585                 590

Met Leu Gln His Glu Gly Cys Ile Glu Cys Gly Thr Cys Ala Arg Glu
        595                 600                 605

Thr Glu Trp Arg His Pro Arg Gly Glu Lys Gly Ile Ile Tyr Asn Tyr
    610                 615                 620

Gly
625


<210> SEQ ID NO 30
<211> LENGTH: 2238
<212> TYPE: DNA
<213> ORGANISM: Crenarchaeote

<400> SEQUENCE: 30

ttggaaggtt cttctctaat acataataat aatctccatg acattggcac aaataatgat     60

aatgtatgtg aaaataaata cattgacgca aaccccggtt tgtcgcacaa acgcggtttt    120

ggtgacgtca acaataacga gaacgataat gatggtggtg ttgacgccgg tgcacccacc    180

acaaaggtgt actatggccc tgaaaacgca aacaacgcca ttttgaggtt catagacagg    240

gccaatgtga agatagactc ttgcataaac tccgtggccc cgtccgtgat gataggggtt    300

gacgccataa gggagaaaag ggttgacgcg gtcaaaaaca ggggccttaa actgcggtat    360

gtaaccgaaa taacaaagga caacgtcggc tatgtcaagg agatgctctc gttttcggag    420

attaggcacc tggatgggct gaagggaaac tttgaggtgg ccgaccagag ggagtatgtg    480

gctgtcgcca cccttcatgc ggcacagtca ataccccagc ttttgttcag caacctccct    540

gagattgcag agcagcagca gtttgtgttt gacagctttt ggggcagggc gttgcccgca    600

gagcacagga taaaggagct ggaggatggg gttgtcatgc ccgtctcact ggtcttctcc    660

aactacaagg acgcggtcca aagggagttt gaaatgataa gcagggccaa aagggagata    720

ctgataatgt actccacggt taacgcgttc cacctgcagg aaaaaggcgg cacactgcaa    780

ctcttgaagg agatggtgga gcaaaacgac agcctgagga tcaacatcct cacgccgatg    840

gatgcctcag tgcgagagtc cttgtccttg aggctcctca caaaatacag gcccaacatc    900

caagtccagg acattgcgcc aagcattggc atcaagataa agacactggt tgtggacaga    960

aaggagtcgc tggtgatgga gctgatacac gcaagggagg aggtggcaac cgccgcaatc   1020

ggcttttcaa tctactccaa cagcgagcca acggtattgt cttactcgtc catatttgag   1080
```

-continued

```
gtcctctatg accagagtgt cctgttccag cagcttgacc aaaacgacaa agtcaaaagc   1140

gagttcataa acgtggctgc gcatgagttg cgaacgccaa tcatgcccat cctaaacggt   1200

gtggagatac tggaggagaa gcttggcgaa agaaaaacag agtttcagcg ggagcttgac   1260

atgataacaa gaaacgcgtc ccggctgcag aaccttgccg aaagcattct gcaggtgagc   1320

agaatcgaaa gcggaagctt tagcctggac atccaaaaaa atgtggatat ccacaacctg   1380

atttcccagg tgatagagga cattgagaaa aaatacgcct acaaggagaa ggcaaacaag   1440

gtggcgatag tgtttttgcc atctgacggc aacagaaatg gcgggtactc cagaggtggc   1500

ggcggcgcaa aggcagaagg ggtaaaggca gcggcaggag caaaacaggc gcaaaaagag   1560

acgcagcaaa aagagcagtg ggtagaaccc gtaaatggcc ccaaccacct tttgtatgta   1620

gactgtgatc cgcaaaagat aagccaggtt gttttcaacc tgctggacaa cgcaatgaag   1680

ttcaccaatg acggcaagat tgttgtttcc acggcagtga tgggtgagtc ttctcccttc   1740

acttccacct ctcaggaaag tgatacctca aacactgcta cagctggtaa aggcaatggg   1800

ggcagagtgg atagcagcag cgacagcgac aacggtggtg gtgacaatgg tggtgaccac   1860

atcgggaggc agaaagaagg cgcggtgcta gtcacagtgc aggacaccgg ggttgggctc   1920

aactccaaaa taagggatca gctgtttcag aaatttgtca caaagtcaaa ccagggaacc   1980

ggccttggcc tatacctgtc aaggaaaatt gttgaggagc atggtggaaa aatatggttt   2040

gaggagacaa acagcaaggg cggcaacagc agcagcagga acaacactaa agataaagac   2100

gaaggcattg atgaaatact gcaccacctt ggcagtgaag gaaaaatagg cgccacattc   2160

aaatttgtca tacctgtctc cctgccttcc catatgccga caaaagacat gccagaaaaa   2220

aacgatgaag gaaaatga                                                 2238
```

```
<210> SEQ ID NO 31
<211> LENGTH: 745
<212> TYPE: PRT
<213> ORGANISM: Crenarchaeote

<400> SEQUENCE: 31

Met Glu Gly Ser Ser Leu Ile His Asn Asn Asn Leu His Asp Ile Gly
1               5                   10                  15

Thr Asn Asn Asp Asn Val Cys Glu Asn Lys Tyr Ile Asp Ala Asn Pro
            20                  25                  30

Gly Leu Ser His Lys Arg Gly Phe Gly Asp Val Asn Asn Asn Glu Asn
        35                  40                  45

Asp Asn Asp Gly Gly Val Asp Ala Gly Ala Pro Thr Thr Lys Val Tyr
    50                  55                  60

Tyr Gly Pro Glu Asn Ala Asn Asn Ala Ile Leu Arg Phe Ile Asp Arg
65                  70                  75                  80

Ala Asn Val Lys Ile Asp Ser Cys Ile Asn Ser Val Ala Pro Ser Val
                85                  90                  95

Met Ile Gly Val Asp Ala Ile Arg Glu Lys Arg Val Asp Ala Val Lys
            100                 105                 110

Asn Arg Gly Leu Lys Leu Arg Tyr Val Thr Glu Ile Thr Lys Asp Asn
        115                 120                 125

Val Gly Tyr Val Lys Glu Met Leu Ser Phe Ser Glu Ile Arg His Leu
    130                 135                 140

Asp Gly Leu Lys Gly Asn Phe Glu Val Ala Asp Gln Arg Glu Tyr Val
145                 150                 155                 160

Ala Val Ala Thr Leu His Ala Ala Gln Ser Ile Pro Gln Leu Leu Phe
```

-continued

```
                165                 170                 175

Ser Asn Leu Pro Glu Ile Ala Glu Gln Gln Gln Phe Val Phe Asp Ser
            180                 185                 190

Phe Trp Gly Arg Ala Leu Pro Ala Glu His Arg Ile Lys Glu Leu Glu
        195                 200                 205

Asp Gly Val Val Met Pro Val Ser Leu Val Phe Ser Asn Tyr Lys Asp
    210                 215                 220

Ala Val Gln Arg Glu Phe Glu Met Ile Ser Arg Ala Lys Arg Glu Ile
225                 230                 235                 240

Leu Ile Met Tyr Ser Thr Val Asn Ala Phe His Leu Gln Glu Lys Gly
                245                 250                 255

Gly Thr Leu Gln Leu Leu Lys Glu Met Val Glu Gln Asn Asp Ser Leu
            260                 265                 270

Arg Ile Asn Ile Leu Thr Pro Met Asp Ala Ser Val Arg Glu Ser Leu
        275                 280                 285

Ser Leu Arg Leu Leu Thr Lys Tyr Arg Pro Asn Ile Gln Val Gln Asp
    290                 295                 300

Ile Ala Pro Ser Ile Gly Ile Lys Ile Lys Thr Leu Val Val Asp Arg
305                 310                 315                 320

Lys Glu Ser Leu Val Met Glu Leu Ile His Ala Arg Glu Glu Val Ala
                325                 330                 335

Thr Ala Ala Ile Gly Phe Ser Ile Tyr Ser Asn Ser Glu Pro Thr Val
            340                 345                 350

Leu Ser Tyr Ser Ser Ile Phe Glu Val Leu Tyr Asp Gln Ser Val Leu
        355                 360                 365

Phe Gln Gln Leu Asp Gln Asn Asp Lys Val Lys Ser Glu Phe Ile Asn
    370                 375                 380

Val Ala Ala His Glu Leu Arg Thr Pro Ile Met Pro Ile Leu Asn Gly
385                 390                 395                 400

Val Glu Ile Leu Glu Glu Lys Leu Gly Glu Arg Lys Thr Glu Phe Gln
                405                 410                 415

Arg Glu Leu Asp Met Ile Thr Arg Asn Ala Ser Arg Leu Gln Asn Leu
            420                 425                 430

Ala Glu Ser Ile Leu Gln Val Ser Arg Ile Glu Ser Gly Ser Phe Ser
        435                 440                 445

Leu Asp Ile Gln Lys Asn Val Asp Ile His Asn Leu Ile Ser Gln Val
    450                 455                 460

Ile Glu Asp Ile Glu Lys Lys Tyr Ala Tyr Lys Glu Lys Ala Asn Lys
465                 470                 475                 480

Val Ala Ile Val Phe Leu Pro Ser Asp Gly Asn Arg Asn Gly Gly Tyr
                485                 490                 495

Ser Arg Gly Gly Gly Gly Ala Lys Ala Glu Gly Val Lys Ala Ala Ala
            500                 505                 510

Gly Ala Lys Gln Ala Gln Lys Glu Thr Gln Gln Lys Glu Gln Trp Val
        515                 520                 525

Glu Pro Val Asn Gly Pro Asn His Leu Leu Tyr Val Asp Cys Asp Pro
    530                 535                 540

Gln Lys Ile Ser Gln Val Val Phe Asn Leu Leu Asp Asn Ala Met Lys
545                 550                 555                 560

Phe Thr Asn Asp Gly Lys Ile Val Val Ser Thr Ala Val Met Gly Glu
                565                 570                 575

Ser Ser Pro Phe Thr Ser Thr Ser Gln Glu Ser Asp Thr Ser Asn Thr
            580                 585                 590
```

-continued

```
Ala Thr Ala Gly Lys Gly Asn Gly Gly Arg Val Asp Ser Ser Ser Asp
        595                 600                 605

Ser Asp Asn Gly Gly Gly Asp Asn Gly Gly Asp His Ile Gly Arg Gln
    610                 615                 620

Lys Glu Gly Ala Val Leu Val Thr Val Gln Asp Thr Gly Val Gly Leu
625                 630                 635                 640

Asn Ser Lys Ile Arg Asp Gln Leu Phe Gln Lys Phe Val Thr Lys Ser
                645                 650                 655

Asn Gln Gly Thr Gly Leu Gly Leu Tyr Leu Ser Arg Lys Ile Val Glu
            660                 665                 670

Glu His Gly Gly Lys Ile Trp Phe Glu Glu Thr Asn Ser Lys Gly Gly
        675                 680                 685

Asn Ser Ser Ser Arg Asn Asn Thr Lys Asp Lys Asp Glu Gly Ile Asp
    690                 695                 700

Glu Ile Leu His His Leu Gly Ser Glu Gly Lys Ile Gly Ala Thr Phe
705                 710                 715                 720

Lys Phe Val Ile Pro Val Ser Leu Pro Ser His Met Pro Thr Lys Asp
                725                 730                 735

Met Pro Glu Lys Asn Asp Glu Gly Lys
            740                 745
```

<210> SEQ ID NO 32
<211> LENGTH: 519
<212> TYPE: DNA
<213> ORGANISM: Crenarchaeote

<400> SEQUENCE: 32

```
ttgcaaagca gtcatctttc taaaataatc acaatttgca gaatgccgtc acttcatctt     60

gttgcatatg gtttaatttt ggatattttc gaaagcccaa tcacaaggtt aaacggtaga    120

acaagtcact tgattattaa aatatatcca catatggata acaatacaag gatgagttct    180

ttagcaatcg agtttttttt atccctttttt tcaataacgt tactttctaa aagaatatac    240

caaccagtga aatcaaagtc atatacctac catgacaagc atccatttca gtacaagatg    300

gaggattatg caaaccacaa caaaattgta gactataaaa actgcttact ttttttcaa    360

gtatcgatgt tacaaaaaaa taaaataatt aggattcggg ttccaggttt gttttataca    420

ggtggctgga tttccctcac actaaagttt ttgatatcca catcatttgc accatcccac    480

ctgaaagtag caatggggcc tccccaggat ataatctga                          519
```

<210> SEQ ID NO 33
<211> LENGTH: 172
<212> TYPE: PRT
<213> ORGANISM: Crenarchaeote

<400> SEQUENCE: 33

```
Met Gln Ser Ser His Leu Ser Lys Ile Ile Thr Ile Cys Arg Met Pro
1               5                   10                  15

Ser Leu His Leu Val Ala Tyr Gly Leu Ile Leu Asp Ile Phe Glu Ser
            20                  25                  30

Pro Ile Thr Arg Leu Asn Gly Arg Thr Ser His Leu Ile Ile Lys Ile
        35                  40                  45

Tyr Pro His Met Asp Asn Asn Thr Arg Met Ser Ser Leu Ala Ile Glu
    50                  55                  60

Phe Phe Leu Ser Leu Phe Ser Ile Thr Leu Leu Ser Lys Arg Ile Tyr
65                  70                  75                  80
```

-continued

```
Gln Pro Val Lys Ser Lys Ser Tyr Thr Tyr His Asp Lys His Pro Phe
                85                  90                  95

Gln Tyr Lys Met Glu Asp Tyr Ala Asn His Asn Lys Ile Val Asp Tyr
            100                 105                 110

Lys Asn Cys Leu Leu Phe Phe Gln Val Ser Met Leu Gln Lys Asn Lys
        115                 120                 125

Ile Ile Arg Ile Arg Val Pro Gly Leu Phe Tyr Thr Gly Gly Trp Ile
    130                 135                 140

Ser Leu Thr Leu Lys Phe Leu Ile Ser Thr Ser Phe Ala Pro Ser His
145                 150                 155                 160

Leu Lys Val Ala Met Gly Pro Pro Gln Asp Ile Ile
                165                 170
```

<210> SEQ ID NO 34
<211> LENGTH: 1008
<212> TYPE: DNA
<213> ORGANISM: Crenarchaeote

<400> SEQUENCE: 34

```
acactgctaa caagcggagg cgcacctgtg cccgcaaccg taagcatgaa ttcaccaacc      60

aacacagttg cgaccctaaa cccctctgca gatttaacac ctggtgccac atacactgcc     120

agaataacaa ccggtgctac ggatgcgact ggtgtcccat tggctgccga caaggtatgg     180

acgttctctg ttgccccttc tggaggcgga gggacattag accagtttgg gataacccag     240

atttaccccg ataaggcggg tggtggagaa aaatggttta tgaatatgca aaacccgaac     300

aatgatccac gaacaaaccc acctgacatg gacctaaacc cagatggcag ttggaacgtt     360

aatgacgatc aggtcagata taacgtgttt acatcatcag ggtaccatcc agaggatatt     420

gagacttacg atcactcggt actcgcaaca caaggataca tgcagtatcc aaatgattgg     480

aagaatgtgg aaatgacggg tattgtaagg gttaatagtg gagatgattc tgaaaatttc     540

gcttggtatg acaggggtgg taggcactat gatggcgaag gatgcgaggg ctcagcatat     600

aaagcagatc tattctatga tggaagggtt aggcttgcaa aagagcagtg gcatgtctcc     660

tatgtgtttt caagcactac cacaccctca ccttcggcgt ctagttttga tagattcatt     720

ggatttaaag ccatgatcta taaccaccaa ttggctggtg gtgagaccgt agtcaccact     780

gaaatatggg tagacagaaa cccggatagc ccgactctga agaacaattg gcaaaaggta     840

tacacattca ctgactcagg tgggtttgga aatgatggtg aagagtgtgg tggtgagccg     900

gatcagatta tatcctgggg aggccccatt gctactttca ggtgggatgg tgcaaatgat     960

gtggatatca aaaactttag tgtgagggaa atccagccac ctgtataa                  1008
```

<210> SEQ ID NO 35
<211> LENGTH: 335
<212> TYPE: PRT
<213> ORGANISM: Crenarchaeote

<400> SEQUENCE: 35

```
Thr Leu Leu Thr Ser Gly Gly Ala Pro Val Pro Ala Thr Val Ser Met
1               5                   10                  15

Asn Ser Pro Thr Asn Thr Val Ala Thr Leu Asn Pro Ser Ala Asp Leu
            20                  25                  30

Thr Pro Gly Ala Thr Tyr Thr Ala Arg Ile Thr Thr Gly Ala Thr Asp
        35                  40                  45

Ala Thr Gly Val Pro Leu Ala Ala Asp Lys Val Trp Thr Phe Ser Val
```

-continued

```
    50                  55                  60

Ala Pro Ser Gly Gly Gly Gly Thr Leu Asp Gln Phe Gly Ile Thr Gln
65                  70                  75                  80

Ile Tyr Pro Asp Lys Ala Gly Gly Gly Glu Lys Trp Phe Met Asn Met
                85                  90                  95

Gln Asn Pro Asn Asn Asp Pro Arg Thr Asn Pro Pro Asp Met Asp Leu
            100                 105                 110

Asn Pro Asp Gly Ser Trp Asn Val Asn Asp Asp Gln Val Arg Tyr Asn
        115                 120                 125

Val Phe Thr Ser Ser Gly Tyr His Pro Glu Asp Ile Glu Thr Tyr Asp
    130                 135                 140

His Ser Val Leu Ala Thr Gln Gly Tyr Met Gln Tyr Pro Asn Asp Trp
145                 150                 155                 160

Lys Asn Val Glu Met Thr Gly Ile Val Arg Val Asn Ser Gly Asp Asp
                165                 170                 175

Ser Glu Asn Phe Ala Trp Tyr Asp Arg Gly Gly Arg His Tyr Asp Gly
            180                 185                 190

Glu Gly Cys Glu Gly Ser Ala Tyr Lys Ala Asp Leu Phe Tyr Asp Gly
        195                 200                 205

Arg Val Arg Leu Ala Lys Glu Gln Trp His Val Ser Tyr Val Phe Ser
    210                 215                 220

Ser Thr Thr Thr Pro Ser Pro Ser Ala Ser Ser Phe Asp Arg Phe Ile
225                 230                 235                 240

Gly Phe Lys Ala Met Ile Tyr Asn His Gln Leu Ala Gly Gly Glu Thr
                245                 250                 255

Val Val Thr Thr Glu Ile Trp Val Asp Arg Asn Pro Asp Ser Pro Thr
            260                 265                 270

Leu Lys Asn Asn Trp Gln Lys Val Tyr Thr Phe Thr Asp Ser Gly Gly
        275                 280                 285

Phe Gly Asn Asp Gly Glu Glu Cys Gly Gly Glu Pro Asp Gln Ile Ile
    290                 295                 300

Ser Trp Gly Gly Pro Ile Ala Thr Phe Arg Trp Asp Gly Ala Asn Asp
305                 310                 315                 320

Val Asp Ile Lys Asn Phe Ser Val Arg Glu Ile Gln Pro Pro Val
                325                 330                 335
```

ISOLATION AND CLONING OF DNA FROM UNCULTIVATED ORGANISMS

This application is the National Phase of International Application PCT/EP2003/009223 filed Aug. 20, 2003 which designated the U.S. and that International Application was published under PCT Article 21(2) in English, and claims priority to EP 02018210.1, filed Aug. 20, 2002.

The present invention relates to a device for the isolation and/or purification of nucleic acid molecules suitable to bind and/or inactivate inhibitors of the activity of reagents or enzymes used for DNA manipulation and to separate a plurality of nucleic acid molecules with respect to their size. Moreover, the invention relates to a method for the isolation of a nucleic acid molecule comprising applying a sample to the device of the invention wherein said nucleic acid molecule preferably is part of a sample which represents a fraction of the metagenome of a given habitat. Furthermore, the invention relates to a method for the generation of at least one gene library comprising nucleic acid molecules isolated by the method of the invention and to a nucleic acid molecule isolated by the method of the invention and with the device of the present invention.

Several documents are cited throughout the text of this specification. The disclosure content of the documents cited herein (including any manufacture's specifications, instructions, etc.) is herewith incorporated by reference.

Enzymes are highly efficient biological catalysts. As such they are key players in environmentally friendly technical conversion processes of modern sustainable biotechnology.

Enzymes particularly from microbial sources are active ingredients in many processes of the textile, detergent, pulp- and paper, food and feed industries. In addition widespread stereoselective substrate recognition and conversion make enzymes particularly attractive for synthetic organic chemists in need of chiral specificity. A bottleneck in the development of innovative technical processes based on enzymes is the supply with suitable new biocatalysts. Owing to their phylogeny and physiological diversity microorganisms constitute the largest resource of natural genetic and enzymatic diversity. However the largest proportion of microorganisms evades cultivation under laboratory conditions (Amann et. al. (1995). Microbiol Rev 59, 143-69). Classic microbiology relying on cultivation of pure strains to provide homogenous and defined systems for homologous enzyme production and to supply genomic DNA for recombinant expression strategies therefore inevitably fails to access the entire biosynthetic potential harboured in this enormous natural resource. The recent development of strategies to directly isolate and clone genomic DNA from non-cultivated microbial consortia opens up new dimensions of accessible enzymatic diversity (Rondon et. al. (2000). Appl Environ Microbiol 66, 2541-7). Fundamental work on the handling of DNA from non-cultivated microorganisms—the so-called metagenome—(Handelsman et. al. (1998) Chem Biol 5, R245-9) by Torsvik (Torsvik and Goksoyr (1978) Soil Biology and Biochemistry 10, 7-12), (Torsvik (1980) Soil Biology and Biochemistry 12, 15-21), Somerville (Somerville et. al. (1989) Appl Environ Microbiol 55(3), 548-554) and Schmidt (Schmidt et. al. (1991) Journal of Bacteriology 173, 4371-4378) showed that genomic DNA can be directly isolated from complex microbial assortments as present, inter alia, in plancton or soil. This DNA may be digested and cloned into suitable vectors for recombinant maintenance in heterologous hosts to generate screenable gene libraries. Such metagenome libraries were shown to be useful in the identification of novel genes from uncultivated organisms. The discovery of novel enzymes by screening of non-normalised metagenome libraries from planctonic and soil sources has been reported in the literature (Cottrell et. al. (1999) Appl Environ Microbiol 65, 2553-7), (Henne et. al. (1999) Appl Environ Microbiol 65, 3901-7; Henne et. al. (2000) Appl Environ Microbiol 66, 3113-3116); (U.S. Pat. No. 5,849,491); (Rondon et. al. (2000) Appl Environ Microbiol 66, 2541-7). The list of enzyme activities discovered in this way (lipase, esterase, amylase, nuclease, chitinase, xylanase) is still rather small. Importantly also more complex activities like the production of bioactive secondary metabolites requiring entire gene clusters for expression have been identified in metagenomic libraries (MacNeil et. al. (2001) J Mol Microbiol Biotechnol 3, 301-8) (Wang et. al. (2000) Org Lett 2, 2401-4) (Brady et. al. (2001) Org Lett 3, 1981-4). Secondary metabolites, like polyketides, are often produced by enzyme complexes encoded by assortments of genes covering in excess of 100 kbp of contiguous DNA (Schwecke et. al. (1995) Proc Natl Acad Sci USA 92, 7839-43). The cloning of such large fragments of environmental DNA is much more challenging than cloning smaller DNA fragments and is substantially facilitated by the current invention. Proprietary technology for the cloning particularly of normalised environmental DNA and the screening of libraries generated thereby is described in U.S. Pat. No. 6,280,926; U.S. Pat. No. 6,054,267; U.S. Pat. No. 6,057,103; U.S. Pat. No. 6,001,574 and PCT applications WO99/45154; WO98/58085; WO99/10539.

DNA directly extracted from microbial consortia in the context of their natural substratum usually is contaminated with substances inhibiting standard enzymatic manipulations that are essentially required for cloning, analysis or amplification of nucleic acids carrying genetic information. In particular the efficiencies of DNA digestion with restriction enzymes (Tsai and Olson (1992) Appl Environ Microbiol 58, 2292-5), (Tebbe and Vahjen (1993) Appl Environ Microbiol 59, 2657-65), the polymerase chain reaction (PCR) (Zhou et. al. (1996) Appl Environ Microbiol 62, 316-22), DNA-DNA hybridisation and bacterial transformation with environmental DNA (Tebbe and Vahjen (1993) loc. cit.) are inversely correlated with natural substrate derived inhibitor concentrations. Besides inorganic inhibitors like heavy metal ions, there are polysaccharides and in particular humic and fulvic acids that act as the single most important sources of above mentioned inhibitions. Humic and fulvic acids are high molecular weight heterocyclic polyphenols mainly of plant origin with an affinity to polynucleotides and strongly protein denaturing properties ((Young et. al. (1993) Appl Environ Microbiol 59, 1972-1974); see appended FIG. 1).

Yet, the efficient removal of such inhibitors is a prerequisite for all enzymatic manipulations required, e.g., for cloning DNA, in particular environmental DNA, into suitable vectors. Several strategies have been pursued. Simple dilution of contaminated DNA to bring inhibitor concentrations below a critical threshold may be sufficient if the subsequent enzymatic manipulation is of suitable power to compensate for the concomitant reduction in target/substrate concentration. Surely such dilution will significantly curtail the efficiency of most subsequent molecular manipulations necessary for cloning following simple mass-action laws. The polymerase chain reaction (PCR), owing to its exponential amplification strategy is powerful enough to generate strong signals even from very low target numbers and often reducing the amount of input environmental DNA (and inhibitors) in a reaction will substantially increase the amount of product achieved (Tsai and Olson (1992) loc. cit.). Gelfiltration of contaminated DNA raw extracts has been used to physically separate DNA from inhibitors based on size differences (Tsai and Olson (1992) loc. cit.), (Jackson et. al. (1997) Applied and Environmental Microbiology 63, 4993-4995), (Miller (2001) J Microbiol Methods 44, 49-58). Charge differences between DNA and inhibitors were exploited in strategies using ion-exchange chromatography purification (Tebbe and Vahjen, (1993) loc. cit.); (Straub et. al. (1995) Water Science and Technology 31, 311-315); (Smalla et. al. (1993) J Appl Bacteriol, 74, 78-85). In a different approach substances showing selective affinity towards polyphenols like soluble polyvinylpyrrolidone (PVP, FIG. 2, relative molecular weight 10'000-360'000 Da), insoluble polyvinylpolypyrrolidone (PVPP, a crosslinked derivative of PVP) or CTAB (hexadecyltrimethylammonium bromide) have been used to absorb (Holben et. al. (1988) Appl. Environ. Microbiol. 54, 703-711) or precipitate inhibitors from solutions (Zhou et. al. (1996) loc. cit.). Berthelet and co-workers used a PVPP affinity-matrix to chromatograph contaminated DNA solutions on spin columns (Berthelet et. al. (1996) FEMS Microbiol Lett 138, 17-22). Using ultracentrifugally generated CsCl density gradients Holben and co-workers (Holben et. al. (1988) loc. cit.) purified DNA from inhibitors based on equilibrium densities. For the construction of high quality libraries of uniform and particularly large DNA insert sizes (in vectors like Cosmid, Fosmid, BAC) a high resolution size selection step is essential to provide the reaction with uniformly sized insert DNA, especially if like in the case for BACs the cloning process does not feature any inherent size selective steps. This makes gel electrophoresis particularly attractive for the purification of environmental DNA. Hereby charge-mass ratios and size differences can be exploited simultaneously to achieve kinetic resolution of DNA from inhibitors and simultaneously the DNA itself is spread out according to size. Although simple gel electrophoresis may suffice to produce clonable DNA from soils containing only small amounts of humic and fulvic acids (Rondon et. al. (2000) loc. cit.), the humic content of soils varies greatly and can reach up to 60-80% of the total organic matter (Tsai and Rochelle (2001) Environmental Molecular Microbiology, Horizon Scientific Press, page 15-30 (Extraction of nucleic acids from environmental samples)). Mostly therefore additional purification steps are necessary and still failures to produce clonable soil DNA are common (Entcheva et. al. (2001) Appl Environ Microbiol 67, 89-99).

A particular modification of this method was devised by Young and co-workers (Young et. al. (1993) loc. cit.). Here, PVP was added to the gel to selectively lower the charge-mass ratio of humic acids so to improve resolution from DNA. This technique combines an affinity-based selective purification step retarding inhibitors in an electric field with a DNA size resolution step that is indispensible in the preparation of insert DNA for efficient large fragment cloning in vectors like BAC. Yet, prior to subsequent enzymatic modifications of environmental DNA as required for cloning (like PCR using e.g. Taq or Pfu DNA polymerases or fill-up reactions using e.g. Klenow- or T4-DNA-polymerase or ligations using e.g. T4-DNA-ligase or multi-step reactions like phage-packaging) absorbants like PVP must be removed as they themselves are inhibitory for further enzymatic processes.

The separation of agarose gel-purified DNA from the PVP absorbant is achieved in the prior art by employing affinity chromatography after melting the DNA containing agarose slice (GeneClean® in (Young et. al. (1993) loc. cit.)). Such a procedure, however, is not suitable to purify very large DNA molecules because shearing forces generated during the elution process will cause fragmentation. Additionally elution efficiency is inversely correlated with molecule size, so large molecules will be selectively lost.

Alternatively, large DNA molecules can be electroeluted from an agarose slice cut from a gel after electrophoresis. The DNA will be recovered in diluted form in a buffer like TAE and has to be concentrated before further manipulation. This routinely involves precipitation in 70% ethanol (Ausubel et. al. (Eds.) (1998) Current Protocols in Molecular Biology, John Wiley & Sons, 2.11-2.1.10). Yet, such an alcohol precipitation involves at least one further centrifugation step and, accordingly, adverse shearing forces. Consequently, in order to purify large DNA fragments form agarose gels for enzymatic manipulation and cloning, prior art procedures involve melting a gel slice containing DNA, performing in-gel enzymatic manipulations in a re-solidified gel (like end polishing, ligation), solubilizing the gel using a degrading enzyme (Gelase® Epicentre, USA) and transforming the DNA into hosts (*E. coli*).

These procedures are complex and may lead to fragmentation or even loss of nucleic acid molecules. Furthermore, these manipulations of the prior art can not be carried out in the presence of enzyme inhibiting substances like PVP.

Many of the above strategies in different combinations have been used as part of multi-step purification protocols to produce clonable "metagenome DNA". Yet, environmental DNA purification is not trivial and whereas purification of DNA for PCR purposes may be accomplished using commercial kits (FastPrep® Bio101, USA), the preparation of sufficient amounts of concentrated and inhibitor-free high-molecular weight DNA (20-300 kbp) for cloning into Cosmids or BACs is much more challenging and may be doomed with failure (Entcheva et. al. (2001) loc. cit).

Thus, the technical problem underlying the present invention was to provide means and method for cloning of genetic material isolated from primary samples. The solution to this technical problem is achieved by providing the embodiments characterized in the claims.

The current invention provides means to overcome the technical difficulties associated with the isolation and cloning of large fragment DNA from uncultivated environmental sources.

Accordingly, the present invention relates to a device for the isolation and/or purification of nucleic acid molecules comprising at least two layers, a first layer being adapted to bind and/or inactivate inhibitors of the activity of reagents or enzymes used in nucleic acid manipulation and a second layer being adapted to separate a plurality of nucleic acid molecules with respect to their size.

The term "device" as employed herein is an arrangement/construction comprising, inter alia, gels, or gel chambers or columns as defined herein. Preferably, the gels, gel chambers or columns form the device of the present invention. The nucleic acid molecules to be isolated and/or purified are isolated and/or purified by passing them through the at least two layers of the device as defined herein.

The term "inhibitors of the activity of reagents or enzymes used in nucleic acid manipulation" describes substances comprised in samples of soil, aquatic samples or samples of symbiotic/parasitic consortia which inhibit the activity of reagents or enzymes used in nucleic acid manipulation. Examples of said substances are described herein above and comprise inorganic inhibitors, like, e.g. heavy metal ions, organic inhibitors, like polysaccharides and in particular humic and fulvic acids. Humic and fulvic acids are high molecular weight heterocyclic polyphenols mainly of plant origin with an affinity to polynucleotides and strongly protein denaturing properties. The chemical structure of humic and fulvic acids is shown in appended FIGS. 1A and 1B. Moreover, the chemical properties of said groups of molecules is described in detail by Stevenson (Humus chemistry: genesis, composition, reactions (1994) Wiley New York) and Buffle (Les substances humiques et leurs interactions avec les ions mineraux (1977) Conference Proceedings de la Commission d'Hydrologie Appliquee de A.G.H.T.M. l'Université d'Orsay, 3-10).

The term "reagents used in nucleic acid manipulation" as used in this context comprises substances like metal ions (e.g. $Mg^{2+}$, $Mn^{2+}$, $Ca^{2+}$), (charged) inorganic and organic molecules required for enzymatic activity or for enzymatic co-factors, said co-factors themselves, or stabilizers. The term "enzymes used in nucleic acid manipulations" relates to enzymes like RNAse(s), DNAse(s), DNA-polymerase(s), ligase(s) or kinase(s) which are used for nucleic acid manipulation.

The term "nucleic acid manipulation" as used herein comprises standard methods known by the person skilled in the art. Said methods comprise DNA-engineering, such as cloning methods of nucleic acid molecules, the mutation of nucleotide sequences of nucleic acid molecules or amplification methods, like, e.g. PCR. Examples for said methods are described in the appended examples and in laboratory manuals, e.g. Sambrook et. al. (1989) *Molecular Cloning: A Laboratory Manual*, Second Edition, Cold Spring Harbor Laboratory Press, Cold Spring Harbor, N.Y.; Ausubel et. al. (1998), loc. cit. In particular, the term "nucleic acid manipulation" relates to the manipulation of DNA or RNA and corresponding cloning techniques.

The term "layer" defines in accordance with the present invention a physical matrix which is characterized by its ability to separate samples containing nucleic acid molecules and also characterized by its ability to separate, if desired, different nucleic acid molecules by their physiological properties, like size or overall charge. The recited first layer is adapted to characterized by its ability to bind and/or inactivate inhibitors described herein above. The ability of the first layer to bind and/or inactivate inhibitors may be achieved by the addition of compounds with sufficiently high binding affinity to the above described inhibitors so to retard their mobility in aqueous solutions and reduce their effective free concentration so to relieve nucleic acids migrating through the device of the invention from comigrating inhibitors.

The recited second layer is characterized by its ability to separate a plurality of nucleic acid molecules with respect to their size. Accordingly, said physical matrix may be a form of a physical matrix, suited to separate nucleic acid molecules based on molecular sieving, e.g. comprising gels or polymers.

According to a preferred embodiment of the device of invention said first layer is arranged above the second layer.

The term "above" defines the position of the first layer relative to the second layer and relative to the direction in which the samples migrate through the layers of the device. Accordingly, the nucleic acid molecule to be isolated and/or purified with the device of the invention is first contacted with the physical matrix of the first layer and afterwards contacted with the matrix of the second layer. Thus, the present invention comprises devices in which the first layer is horizontally above the second layer as well as devices in which the first layer is vertically above the second layer. Such a device is illustratively exemplified in the appended examples as a gel comprising two phases/layers. Accordingly, as illustrated in the appended figures and examples and described herein, this device may be arranged in form of a gel. Therefore, the device of the invention may be a device, wherein said first layer is a first phase of a gel and said second layer is a second phase of said gel. In its broadest sense, the term "phase" of a gel indicates that this phase has a different overall chemical constitution than a further (second) phase of said gel. For example, the difference in the overall chemical construction may be due to the presence of chemicals/compounds that bind or inactivate the above mentioned inhibitors of the activity of reagents or enzymes used in nucleic acid manipulations.

Preferably, the device of the present invention comprises a gel, wherein said gel is an agarose-gel or a polyacrylamid-gel.

Methods for the preparation of said gels are known by the person skilled in the art and are described in the appended examples and in standard laboratory manuals, e.g. Sambrook et. al. (1989), loc. cit., Cold Spring Harbor, N.Y.; Ausubel et. al. (1998), loc. cit.

Preferably, the device of the invention comprises in said first layer polyvinylpyrrolidone (PVP), or polyvinylpolypyrrolidone (PVPP) or combinations thereof. As demonstrated in the appended examples PVP and PVPP are immobile components of said first layer or are characterized at least by a lower mobility compared to the nucleic acid molecules and to bind or interact with the above characterized "inhibitors of the activity of reagents or enzymes used in nucleic acid manipulation".

Further examples of corresponding components of said first layer (i.e. inactivators of the inhibitors defined herein above) are functional molecules like CTAB, EDTA, EGTA, cyclodextrins, proteins, (poly)peptides, nucleic acids immobilized or tethered on appropriate matrices acting as catcher molecules or ion-exchanger. These functional molecules may act by complexing ions (like EDTA, EGTA,), precipitating polysaccarides (like CTAB), binding small hydrophobic molecules or uncharged small molecules, like cyclodextrins, binding specific surface structures (like proteins, (poly)peptides and aptamers). Said proteins may comprise, e.g., antibodies and (poly)peptides directed against inhibitors. Furthermore, lectins are envisaged as inactivators of the inhibitors defined herein. An example for a nucleic acids acting as catcher molecules in accordance with the invention are RNA-aptamers.

The term "(poly)peptide" as used herein summarizes a group of molecules which comprise the group of peptides, consisting of up to 30 amino acids, as well as the group of polypeptides, consisting of more than 30 amino acids.

Above described low molecular weight compounds comprise electrically charged compounds (e.g. CTAB, EDTA) and uncharged small molecules (e.g. cyclodextrin). Said compounds are soluble in aqueous solutions and, thus, mobile due to rapid diffusion and in particular mobile in an electrical field. In order to achieve a lower mobility of said compounds compared to the nucleic acid molecules, said compounds may be coupled to the physical matrices (e.g. chemically coupled). Compounds which are soluble in aqueous solutions but not electrically charged (e.g. PVP) and compounds which are non-soluble in aqueous solutions (e.g. PVPP) show a lower mobility compared to the nucleic acid molecules and thus do not essentially require to be coupled to the physical matrices.

More preferably, the device the invention is a device, wherein said second layer is substantially free of PVP, PVPP, CTAB, EDTA, EGTA, cyclodextrins, proteins, (poly)peptides, nucleic acids or ion-exchanger.

The term "substantially free" is understood in accordance with the invention to define a layer which does not contain the recited compounds in an effective amount which is detectable by standard methods. Said standard methods are known in the art and comprise MS (mass spectrometry), FT-IR (fourier transform infrared spectrometry), NMR (nuclear magnetic resonance) or HPLC (high performance liquid chromatography). Accordingly, the second layer does, most preferably, not contain any of the recited compounds as an essential/effective element.

According to a more preferred embodiment the device of the invention is electrically biased to enhance flow of (a) sample(s) through the layers.

As known by the person skilled in the art nucleic acid molecules are negatively charged due to the ribose-phosphate framework. Accordingly, nucleic acid molecules migrate in an electrical field from the cathode (−) to the anode (+).

Examples for devices which are electrically biased to enhance flow of (a) sample(s) are devices for gel electrophoresis. Devices with continuous as well as devices with discontinuous electrical fields are particularly comprised by the present invention. Accordingly, the electrical field can be discontinuous due to a gradient of a salt (buffer salt), a pulsed field comprising e.g. different angles. Again, an electrically biased device in accordance with the present invention is shown in the appended figures and illustrated in the appended examples.

The invention relates to a device, wherein said first layer preferably comprises sample loading means.

The term "sample loading means" defines in accordance with the invention means for placing the sample comprising nucleic acid molecules in the device of the invention. Examples for said means are sample slots in a gel, the surface of the matrix of a column or a valve for injecting a sample onto a column.

The isolation of nucleic acid molecules by using a device of the invention in the format of a horizontal agarose-gel is described in the appended example 1 and in the format of a single column is described in the appended example 4. Examples for the corresponding devices are shown in the appended FIGS. 3 and 4.

In a more preferred embodiment of the invention said loading means are provided in an array in an upper portion of the first layer, defining an array of columns, each being capable of isolating nucleic acid molecules.

Hence, a device according to the preferred embodiment of the invention comprises more than one means for placing the sample. Thus, it is possible to isolate nucleic acid molecules from different samples in parallel. An example for loading means provided in an array is a gel comprising different loading slots and, therefore, different lanes (lines in which the samples are separated). An alternative example for said array are columns which are arranged in groups, e.g. in a frame. Said frame may comprise low numbers of columns (two to twelve) for the isolation of nucleic acid molecules from low numbers of samples. Also in accordance with the invention are frames comprising medium numbers of columns (twelve to 96) as well as frames with high numbers of columns (more than 96) which are suitable for high throughput screens (HTS).

According to an alternative embodiment of the invention said first layer of the device is arranged below the second layer.

The term "below" defines the position of the second layer relative to the first layer and relative to the direction in which the samples migrate through the layers of the device. The present invention comprises devices for the isolation and/or purification of nucleic acid molecules in which the nucleic acid molecules are first contacted with the physical matrix of the second layer to separate the molecules with respect to their size and subsequently contacted with the physical matrix of the first layer to bind and/or inactivate the above defined inhibitors.

Accordingly, the present invention comprises devices in which the second layer is horizontally above the first layer as well as devices in which the second layer is vertically above the first layer. Most preferred is in this context a device in form of a column, wherein said column comprises said first and said second layer.

An alternatively preferred embodiment of the invention relates to a device, wherein said second layer is a first phase of a column and said first layer is a second phase of said column. As pointed out herein above, the first layer comprises functional molecules capable of inactivating or binding inhibitors of the activity of reagents or enzymes used in nucleic acid manipulation.

It is also envisaged, in accordance with the invention, that an enhancement of the flow of (a) sample(s) through the layers of the device is, for example, achieved by gravity or by the pressure of the flow of a diluent. Examples for appropriate diluents are buffer solutions. The appended Examples show a device in form of a column as described herein.

Preferably, the device of the invention comprises in said first layer (in a column preferably the second phase) a matrix comprising PVP or PVPP or combinations thereof. As described herein above PVP and PVPP are characterized at least by a lower mobility compared to the nucleic acid molecules and to bind or interact with the above characterized "inhibitors of the activity of reagents or enzymes used in nucleic acid manipulation".

Further examples of corresponding components of said first layer (i.e. compounds capable of inactivating the inhibitors of nucleic acid manipulations) are EDTA, EGTA, CTAB, cyclodextrins, proteins, (poly)peptides, nucleic acids acting as catcher molecules or ion-exchangers. Said proteins may comprise, e.g., antibodies directed against inhibitors. Also lectins are envisaged as inactivators. An example for said nucleic acids acting as catcher molecules in accordance with the invention are RNA-aptamers.

More preferably the device the invention is a device, wherein said second layer (in a column preferably the first phase) is a matrix which is substantially free of PVP, PVPP, CTAB, EDTA, EGTA, cyclodextrins, proteins, (poly)peptides, nucleic acids or ion-exchangers.

The term "substantially free" is defined herein above.

According to a further preferred embodiment of the invention, said matrix of said first and/or second layer is agarose, SEPHAROSE™, SEPHADEX™ SEPHACRYL™, BIO-GEL™, SUPEROSE™ or acrylamide.

Variations of the samples comprising the nucleic acid molecules to be isolated and/or purified with the device of the invention may require specific materials of the matrix of the first and/or the second layer. Said variations may concern the quality of the comprised nucleic acid molecules as well as the quality of the sample itself with respect to characteristic substances which may be contained. Accordingly, the matrix of the first and/or the second layer may be a specific matrix for gel-filtration which allows a molecular sieving of the nucleic acid molecules. Suitable media for matrices are characterized by a specific size of the pores which is known by the person skilled in the art and described in the instructions provided by the manufacturer of commercially available media. Said matrices comprise media for gel-filtration.

Said matrices comprise media for gel-filtration. Examples of said media comprise SEPHAROSE™ (e.g. SEPHAROSE™ 2B, SEPHAROSE™ 4B, SEPHAROSE™ 6B), SEPHADEX™ (e.g., sephadex SEPHADEX™ G200, sephadex SEPHADEX™ G150) SEPHACRYL™ and SUPEROSE™ as well as BIO-GEL™ P100 and BIO-GEL™ P200. Moreover, said media comprise agarose, polymers as e.g. dextrans and acylamid based-resins. In particular, media are preferred which are suitable for two-phases-columns. Further suitable materials are known to the person skilled in the art.

In a further preferred embodiment of the device of the invention said nucleic acid molecule is DNA or RNA. Most preferably, said DNA is genomic DNA (gDNA).

A particularly preferred embodiment of the invention is a device, wherein said nucleic acid molecule is derived from (micro)organisms of soil, sediments, water, for example sea water, or symbiotic/parasitic consortia.

The term "soil" defines in accordance with the invention the complex product of geological and biological processes acting on inorganic minerals and biomass deposited on the earth surface. It contains the majority of microbial biodiversity on earth (Whitman et. al. (1998) Proc Natl Acad Sci USA, 95(12, 6578-83) acting to recycle and biomineralize organic matter and serves as a substratum to anchor and nourish higher plants.

In the appended examples the preparation of nucleic acid molecules isolated from soil is exemplarily described.

Examples for symbiotic/parasitic consortia in accordance with the present invention are consortia isolated e.g. from animal tissues or organs, e.g. from gut, stomach, intestines, like appendix or insect-, bird- and mammalian-intestinal tracts or -guts, comprising ruminant-gut. Also envisaged are animal tissues or organs from annelid(s), mollusc(s), sponge(s), cnidaria, arthropod(s), amphibian(s), fish or reptile(s). However, it is also envisaged that nucleic acids from parasitic consortia from human tissue, organs, sputum, faeces, sperm, blood, urine or other body fluids are isolated.

More preferably said (micro)organisms from which said nucleic acid molecules are derived from are (micro)organisms of aquatic plancton, animal tissues and organs as described herein above, microbial mats, clusters, sludge flocs, or biofilms.

(Micro)organisms of the "aquatic plancton" comprises bacterial plancton, archaeal plancton, viruses, phytoplancton as well as zooplancton. Said (micro)organisms are known as small organisms.

Biofilms are microbial assemblages on a surface in "aqueous environments" in which microbes are embedded in a hydrated polymeric matrix. This matrix acts like a kind of glue, holding the microbes together, attaching them to the surface and protecting them from detrimental external influences. They may contain several taxonomically distinct species (e.g. bacteria, fungi, algae, and protozoa) and may form on surfaces of diverse composition like e.g. metals, glass, plastics, tissue, mineral and soil particles.

Microbial mats and clusters are microbial assemblages/aggregates similar to biofilms in composition however not necessarily as firmly attached to solid surfaces.

According to a further preferred embodiment of the invention said (micro)organisms are isolated and/or purified as consortia of coexisting species. Preferably it is envisaged that said (micro)organisms are isolated and/or purified as consortia of coexisting species without previous separation/purification of single microorganismic species.

Preferably said consortia of coexisting species comprise at least one organism that cannot proliferate indefinitely in an artificial setting (e.g. a synthetic or semisynthetic culture medium) in the absence of other species and/or in the absence of the substratum it is isolated from, and wherein said substratum contains the above defined inhibitors of the activity of reagents or enzymes used in nucleic acid manipulation.

To obtain the DNA of said microorganisms they may either be bulk-separated mechano-chemically from most of the surrounding matrix they are attached to or embedded or suspended in (like water, soil, sediments, organic debris of plant or animal origin) before lysis (indirect lysis) or they may be lysed and extracted directly i.e. still in the context of/attached to their surrounding physical matrix (soil, biofilm, floc, cluster) that contains a plurality of potential inhibitors of molecular, in particular enzymatic manipulation. Bulk-separation of microorganisms may be accomplished e.g. through mechanical agitation, ion-exchange resin mediated desorption (optionally facilitated through substances added to the extraction buffers used like detergents, salts) followed by an optional concentration step like filtration (for suspended plankton) or suspending and differential gravitational sedimention in a liquid. In both instances total nucleic acids of mixed origin are isolated irrespective of taxonomic status, abundance and cultivability of the respective taxonomically mixed species.

Classic isolation of nucleic acid molecules from single microbial species or groups of microbial species comprise cultivation of said organisms by massive dilution in selectively growth supporting media. Thereby above mentioned inhibitors of molecular manipulation of nucleic acids are diluted to facilitate subsequent isolation and cloning. Yet at the cost of a massive reduction in species representation as very few species can be supported by standard cultivation techniques (see herein above). In contrast the present invention provides means for the isolation of nucleic acid molecules derived from taxonomically mixed (micro)organisms without cultivation in synthetic media. Since such steps of cultivation under laboratory conditions results in depletion or at least in significant dilution of organisms which do not grow under said conditions the present invention surprisingly provides means for the isolation and/or purification of nucleic acid molecules derived from said organisms.

In a preferred embodiment of the invention said nucleic acid molecules represent a fraction of the metagenome of a given habitat.

As known in the art the term "metagenome" defines the totality of all genomes of organisms of a given habitat and is furthermore defined in the art; see inter alia Handelsman et. al. (1998) loc. cit. In particular, the term "metagenome" relates to genomic nucleic acids, preferably DNA, derived from unknown or uncultivable microorganisms, i.e. organisms that cannot be isolated by standard methods and made actively replicating in standard artificial media for indefinite periods of time. Accordingly the term "a fraction of the metagenome of a given habitat" defines in accordance with the invention nucleic acid molecules and in particular large nucleic acid molecules (>200 bp) derived from the total pool of heterogenous microbial genomes present in a given habitat. This is irrespective of phylogenetic affiliation or molecular or physiological traits. Particularly the representation of any particular microbial genome in the extracted portion of the metagenome is not influenced by or dependent on the cultivatability of this organism. Therefore nucleic acids of uncultivated and in a preferred form particularly of uncultivatable (micro)organisms are substantially represented in the extracted fraction of the metagenome.

An alternative embodiment of the invention relates to a method for the isolation of a nucleic acid molecule comprising applying a sample to the device as defined herein above. Said sample (for example derived from soil, sediments, water or symbiotic/parasitic consortia) is loaded onto a device comprising the above-identified at least two layers (for example a gel or a column comprising said two layers) and the nucleic acid molecule is purified and/or isolated by passing them through said two layers. In accordance with the invention, the first layer as defined herein, i.e. the layer comprising the inactivators of the inhibitors of reagents and enzymes of nucleic acid manipulations, 4 retains said inhibitors, wherein said second layer provides for, e.g., an isolation and separation step for isolating/separating the nucleic acid molecules in accordance with their physical properties, like size or overall charge. It is envisaged and documented in the appended examples, that the nucleic acid molecules to be isolated pass completely through the two layers of the device of the invention (e.g. a column comprising the two layers) or that the nucleic acid molecules pass only partially through the second layer. For example, it is envisaged that said nucleic acid molecules pass completely through said first layer comprising the inactivators of inhibitors and only partially through said second layer which is substantially free of said inactivators. This method is, inter alia, employed in the device of the invention which is in form of a gel. The nucleic acid molecules to be isolated and/or purified may be isolated or purified from the second layer by conventional means, for example by electroelution.

The method of the invention is also exemplified in the appended examples 1, 4 and 5.

Said method may optionally comprise one or more additional steps of subsequent purification of the obtained nucleic acid molecule(s).

According to a preferred embodiment of the method of the invention a fractions of the metagenome is isolated from a given habitat.

The invention relates in an alternative embodiment to a method for the generation of at least one gene library, comprising the steps of (a) isolating and/or purifying nucleic acid molecules from a sample using a device as defined herein above and optionally amplifying said nucleic acid molecules;
(b) cloning the isolated and/or purified and optionally amplified nucleic acid molecules into appropriate vectors; and
(c) transforming suitable hosts with said suitable vectors.

Methods for the amplification of an isolated and/or purified nucleic acid molecule are known in the art and comprise e.g. polymerase chain reaction (PCR).

Methods for the cloning of nucleic acid molecules into appropriate vectors and transforming suitable hosts with said suitable vectors represent standard methods of molecular biology and are described in the appended examples (in particular, example 2) and in laboratory manuals, e.g. Sambrook et. al. (1989) loc. cit.; Ausubel et. al. (1998), loc. cit.; Mülhardt (2002) Der Experimentator: Molekularbiologie/Genomiocs; Gustav Fischer. Suitable vectors are described herein below.

The above described method may, optionally, additionally comprise one or more of the following steps prior to the cloning of nucleic acid molecules into appropriate vectors according to step (b):

(i) modification of DNA ends of the isolated and/or purified nucleic acid molecules, e.g. to remove or fill-up random 3'- or 5'-overhangs (polishing/fill-up/blunting), by DNA polymerase treatment (e.g. with Klenow enzyme, T4-polymerase) or treatment with exonucleases (like mung bean nuclease) or introducing defined 3' overhangs (like single nucleotide overhangs, in particular adenosin overhangs) using, e.g. DNA polymerase (like Taq), for subsequent cloning into appropriate vectors (e.g. T-overhang vectors like pGEM T-easy from Promega, USA) or introducing 3'- or 5'-overhangs using restriction endo-nucleases;
(ii) phosphorylation of the isolated and/or purified nucleic acid molecules (e.g. by PNK); and/or
(iii) ligation of the isolated and/or purified nucleic acid molecules to other nucleic acid molecules by treatment with an enzymatic ligase (e.g. by T4-ligase) or topoisomerase.

Also envisaged is a “sizing” step, as also illustrated briefly in (i) herein above, wherein said step comprises sizing the obtained nucleic acid molecules by treatment of the isolated and/or purified nucleic acid molecules with an enzymatic endonuclease (e.g. by restriction endonucleases or DNAse I) and/or mechanical shearing (e.g. by ultrasonication or passing nucleic acids with high pressure through narrow tubes or valves similar to the “nebulizer” from Invitrogen, USA).

Suitable vectors comprise plasmid vectors (e.g. pUC18 and derivates thereof, pBluescript etc.), cosmid vectors (e.g. Expand, SuperCos), fosmid vectors (e.g. EpiFos 5), phage vectors (e.g. lambda ZAP), BAC vectors (e.g. pBeloBAC) and YAC vectors.

Preferably, said suitable hosts are selected from the group consisting of *E. coli*, *Pseudomonas* sp., *Bacillus* sp, *Streptomyces* sp, other actinomycetes, myxobacteria yeasts and filamentous fungi.

Transformation of said suitable host may be assayed by standard methods of molecular biology; see Sambrook et. al. (1989) loc. cit.; Ausubel et. al. (1998), loc. cit.; Mülhardt (2002) loc. cit. Corresponding assays for a successful transformation may be based on sequence similarity and performed on plated colonies (filter hybridization) by probe hybridization or by PCR analysis of colonies or extracted DNA of single or multiple colonies. Methods for the preparation of suitable oligonucleotides are known in the art. Alternatively the inserts may be sequenced and targets identified via homology search in appropriated sets of deposited sequence data (e.g. GenBank).

Activity based assays may be performed by screening for substrate conversion/degradation inside or outside the host (scoreable by substrate clearing zones around colonies; color development; molecular product profiling by high performance liquid chromatography (HPLC), mass spectrography (MS) or gas chromatography (GC); complementation of growth-deficient mutants), by screening for growth inhibition/stimulation of indicator organisms (in overlays).

Accordingly, and in a further embodiment, the present invention relates to a gene library obtained by the method disclosed herein and by employing the device described in this invention.

An alternative embodiment of the invention relates to a gene library generated from metagenome nucleic acid molecules, preferably from DNA, from non-planctonic (micro) organisms comprising average insert sizes of at least 50 kB, at least 55 kB, at least 60 kB, at least 70 kB, at least 80 kB, at least 90 kB or at least 100 kB.

As defined herein above planctonic (micro)organisms of the “aquatic plancton” comprises bacterial- and archaeal plancton, viruses, phytoplancton as well as zooplancton. Said (micro)organisms are known as small organisms living in aquatic habitats. Accordingly the term “non-planctonic (micro)organisms” defines (micro)organisms in accordance with the invention which are not comprised by the term “planctonic (micro)organisms”. This group of (micro)organisms comprise (micro)organisms of soil, microbial mats, clusters sludge flocs, biofilms and symbiotic/parasitic consortia.

Similarly, the invention relates to a gene library generated from metagenome nucleic acid molecules, preferably DNA, from planctonic (micro)organisms comprising average insert sizes of at least 85 kB, at least 90 kB, at least 95 kB, at least 100 kB, at least 120 kB, at least 140 kB, at least 160 kB or at least 200 kB.

In contrast to the group of "non-planctonic (micro)organisms" defined herein above the term "planctonic (micro)organisms" defines (micro)organisms of the "aquatic plancton" comprises bacterial- and archaeal plancton, viruses, phytoplancton and zooplancton as described herein above.

The average insert size of a (gene) library is, inter alia, determined by (a) isolating the cloned recombinant DNA of at least 0.1% of the clones of the respective library (however no less than a minimum of 20 clones) by methods known in the art, (b) digesting the isolated cloned recombinant DNA molecules with restriction enzymes (6-base or 8-base cutters, e.g., BamHI or EcoRI or Not I used singular or in combination) so to preferentially digest the vector backbone away from insert DNA (e.g. Not I used for pEpiFos5), (c) separating the resulting DNA fragments obtained from each clone individually by agarose gel electrophoresis (continuous or plused-field) as known in the art and (d) adding together the sizes of all non-vector fragments of all analyzed clones of a library and dividing the resulting number by the number of clones analyzed in order to obtain a figure for the average insert size.

The present invention relates further to a nucleic acid molecule comprising a DNA as depicted in SEQ ID NO: 1 or comprising a DNA as deposited under EMBL accession number AJ496176.

Said nucleic acid molecule of the invention has been isolated and obtained by employing the device of the invention. It represents a part of the genome of the newly identified Crenarchaeote as isolated with methods described herein and by techniques implied in the device of the present invention. Taxonomically the crenachaeota represent a prokaryotic phylum as part of the archeal kingdom. The majority of its representatives are known to be hyperthermophiles yet increasingly they are found in mesophilic habitats as well; see Burggraf et al. (1997) Int J Syst Bacteriol., 47, 657-660; Preston et al. (1996) Proc Natl Acad Sci USA., 93, 6241-46. In the context of the present invention, the term "genome" defines not only sequences which are open reading frames (ORFs) encoding proteins, polypeptides or peptides, but also refers to non-coding sequences. Accordingly, the term "nucleic acid molecule" comprises coding and, wherever applicable, non-coding sequences. The nucleic acid molecule of the invention furthermore comprises nucleic acid sequences which are degenerative to the above nucleic acid sequences. In accordance with the present invention, the term "nucleic acid molecule" comprises also any feasible derivative of a nucleic acid to which a nucleic acid probe may hybridize. Said nucleic acid probe itself may be a derivative of a nucleic acid molecule capable of hybridizing to said nucleic acid molecule or said derivative thereof. The term "nucleic acid molecule" further comprises peptide nucleic acids (PNAs) containing DNA analogs with amide backbone linkages (Nielsen, P., Science 254 (1991), 1497-1500). The term "ORF" ("open reading frame") which encodes a polypeptide, in connection with the present invention, is defined either by (a) the specific nucleotide sequences encoding the polypeptides specified above in (aa) or in (ab) or (b) by nucleic acid sequences hybridizing under stringent conditions to the complementary strand of the nucleotide sequences of (a) and encoding a polypeptide deviating from the polypeptide of (a) by one or more amino acid substitutions, deletions, duplications, insertions, recombinations, additions or inversions.

Furthermore the present invention relates in one embodiment to a nucleic acid molecule representing part of the genome of a non-thermophilic crenarchaeote, whereby said nucleic acid molecule has at least one of the following features:

(a) it contains at least one ORF which encodes a polypeptide having the amino acid sequence SEQ ID NO: 3, SEQ ID NO: 5, SEQ ID NO: 7, SEQ ID NO: 9, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31, SEQ ID NO: 33, SEQ ID NO: 35;

(b) comprises the DNA sequence of SEQ ID NO: 1, SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34;

(c) it comprises portion of at least 20 nucleotides, preferably 100 nucleotides, more preferably at least 500 nucleotides which hybridize under stringent conditions to the complementary strand of SEQ ID NO: 2, SEQ ID NO: 4, SEQ ID NO: 6, SEQ ID NO: 8, SEQ ID NO: 10, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32, SEQ ID NO: 34;

(d) it is degenerate as a result of the genetic code with respect to the nucleic acid molecule of (c); or (e) it is at least 50% identical with the nucleic acid molecule of SEQ ID NO: 2, SEQ ID NO: 20 or SEQ ID NO: 30, 45% identical with the nucleic acid molecule of SEQ ID NO: 8 or SEQ ID NO: 26, 35% identical with the nucleic acid molecule of SEQ ID NO: 16, SEQ ID NO: 22 or SEQ ID NO: 24 or 30% identical with the nucleic acid molecule of SEQ ID NO: 4, SEQ ID NO: 14, SEQ ID NO: 18 or SEQ ID NO: 28;

The following list relates to the SEQ ID NOS as defined herein and shows (partial) identification of ORFs as defined herein:

| Name | Identity |
|---|---|
| SEQ ID NO: 1 | complete DNA sequence 29i4, 33925 nt, of a newly identified Crenarchaeote |
| SEQ ID NO: 2 | ORF001 DNA sequence, 2367 nt, Fam. B DNA Polymerase (truncated ORF) |
| SEQ ID NO: 3 | ORF001 Protein sequence, 789 aa, Fam. B DNA Polymerase (truncated protein) |
| SEQ ID NO: 4 | ORF002 DNA sequence, 882 nt, $\alpha/\beta$ hydrolase |
| SEQ ID NO: 5 | ORF002 Protein sequence, 293 aa, $\alpha/\beta$ hydrolase |
| SEQ ID NO: 6 | ORF003 DNA sequence, 318 nt |
| SEQ ID NO: 7 | ORF003 Protein sequence, 105 aa |
| SEQ ID NO: 8 | ORF004 DNA sequence, 1086 nt, Polyhydroxyalkanoate Synthase |
| SEQ ID NO: 9 | ORF004 Protein sequence, 361 aa, Polyhydroxyalkanoate Synthase |
| SEQ ID NO: 10 | ORF005 DNA sequence, 582 nt |
| SEQ ID NO: 11 | ORF005 Protein sequence, 193 aa |
| SEQ ID NO: 12 | ORF006 DNA sequence, 438 nt |
| SEQ ID NO: 13 | ORF006 Protein sequence, 145 aa |
| SEQ ID NO: 14 | ORF007 DNA sequence, 915 nt, Glycosyl Transferase group 1 |
| SEQ ID NO: 15 | ORF007 Protein sequence, 304 aa, Glycosyl Transferase group 1 |
| SEQ ID NO: 16 | ORF008 DNA sequence, 1692 nt, Asparagine Synthase |
| SEQ ID NO: 17 | ORF008 Protein sequence, 563 aa, Asparagine Synthase |

-continued

| Name | Identity |
|---|---|
| SEQ ID NO: 18 | ORF009 DNA sequence, 666 nt, Phosphoserin Phosphatase |
| SEQ ID NO: 19 | ORF009 Protein sequence, 221 aa, Phosphoserin Phosphatase |
| SEQ ID NO: 20 | ORF010 DNA sequence, 1212 nt |
| SEQ ID NO: 21 | ORF010 Protein sequence, 403 aa |
| SEQ ID NO: 22 | ORF011 DNA sequence, 1164 nt, Transmembrane protein |
| SEQ ID NO: 23 | ORF011 Protein sequence, 387 aa, Transmembrane protein |
| SEQ ID NO: 24 | ORF012 DNA sequence, 882 nt, Fix A Electron Transfer Flavoprotein |
| SEQ ID NO: 25 | ORF012 Protein sequence, 293 aa, Fix A Electron Transfer Flavoprotein |
| SEQ ID NO: 26 | ORF013 DNA sequence, 1284 nt, Fix B Electron Transfer Flavoprotein |
| SEQ ID NO: 27 | ORF013 Protein sequence, 427 aa, Fix B Electron Transfer Flavoprotein |
| SEQ ID NO: 28 | ORF014 DNA sequence, 1878 nt, Fix CX Fusion Electron Transfer Flavoprotein |
| SEQ ID NO: 29 | ORF014 Protein sequence, 625 aa, Fix CX Fusion Electron Transfer Flavoprotein |
| SEQ ID NO: 30 | ORF015 DNA sequence, 2238 nt, Sensory Transduction Histidin Kinase |
| SEQ ID NO: 31 | ORF015 Protein sequence, 745 aa, Sensory Transduction Histidin Kinase |
| SEQ ID NO: 32 | ORF016 DNA sequence, 519 nt |
| SEQ ID NO: 33 | ORF016 Protein sequence, 172 aa |
| SEQ ID NO: 34 | ORF017 DNA sequence, 1008 nt, (truncated ORF) |
| SEQ ID NO: 35 | ORF017 Protein sequence, 335 aa, (truncated protein) |

A potential field of application of "ORF004" as defined herein comprise the generation or modification of biogenic polymers/polyesters (polyhydroxyalkanoate synthase, Zinn, (2001) Adv Drug Deliv Rev 53(1):5-21 and Fidler, (1992), FEMS Microbiol Rev 9(2-4):231-5; Snell, (2002) Metab. Eng. 4(1):29-40)

Furthermore, the ORF008, a potential asparagine synthetase may be used in the context of amino acid synthesis (EC 6.3.5.4) and/or for the generation of transgenic organisms, like bacteria, plants with altered capacities to generate amino acids.

In addition, ORFs 12, 13 or 14 may play a role in redox processes involved in nitrogen fixation and may be useful in generating transgenic organisms like bacteria, plants with altered capacities to assimilate nitrogen.

The term "hybridizing" as used herein refers to a pairing of polynucleotides to a complementary strand of polynucleotide which thereby form a hybrid. Said complementary strand polynucleotides are, e.g. the polynucleotides of the invention or parts thereof. Therefore, said polynucleotides may be useful as probes in Northern or Southern Blot analysis of RNA or DNA preparations, respectively, or can be used as oligonucleotide primers in PCR analysis dependent on their respective size. Preferably, said hybridizing polynucleotides comprise at least 10, more preferably at least 15 nucleotides in length while a hybridizing polynucleotide of the present invention to be used as a probe preferably comprises at least 100, more preferably at least 200, or most preferably at least 500 nucleotides in length.

It is well known in the art how to perform hybridization experiments with nucleic acid molecules, i.e. the person skilled in the art knows what hybridization conditions s/he has to use in accordance with the present invention. Such hybridization conditions are referred to in standard text books such as Sambrook et. al. (1989) loc. cit. or Higgins, S. J., Hames, D. "RNA Processing: A practical approach", Oxford University Press (1994), Vol. 1 and 2.

"Stringent hybridization conditions" (also referred to highly stringent conditions as contrasted to conditions of low stringency) refers to conditions which comprise, e.g. an overnight incubation at 42° C. in a solution comprising 50% formamide, 5×SSC (750 mM NaCl, 75 mM sodium citrate), 50 mM sodium phosphate (pH 7.6), 5×Denhardt's solution, 10% dextran sulfate, and 20 μg/ml denatured, sheared salmon sperm DNA, followed by washing the filters in 0.1×SSC at about 65° C. Said conditions for hybridization are also known by a person skilled in the art as "high stringent conditions for hybridization". Also contemplated are nucleic acid molecules that hybridize to the polynucleotides of the invention at lower stringency hybridization conditions ("low stringent conditions for hybridization"). Changes in the stringency of hybridization and signal detection are primarily accomplished through the manipulation of formamide concentration (lower percentages of formamide result in lowered stringency); salt conditions, or temperature. For example, lower stringency conditions include an overnight incubation at 37° C. in a solution comprising 6×SSPE (20×SSPE=3M NaCl; 0.2M $NaH_2PO4$; 0.02M EDTA, pH 7.4), 0.5% SDS, 30% formamide, 100 μg/ml salmon sperm blocking DNA; followed by washes at 50° C. with 1×SSPE, 0.1% SDS. In addition, to achieve even lower stringency, washes performed following stringent hybridization can be done at higher salt concentrations (e.g. 5×SSC). Note that variations in the above conditions may be accomplished through the inclusion and/or substitution of alternate blocking reagents used to suppress background in hybridization experiments. Typical blocking reagents include Denhardt's reagent, BLOTTO, heparin, denatured salmon sperm DNA, and commercially available proprietary formulations. The inclusion of specific blocking reagents may require modification of the hybridization conditions described above, due to problems with compatibility.

Preferred in accordance with the present inventions are polynucleotides which are capable of hybridizing to the polynucleotides of the invention or parts thereof, under stringent hybridization conditions, i.e. which do not cross hybridize to unrelated polynucleotides.

The nucleic acid molecules that are homologous to the above-described molecules and that represent derivatives of these molecules usually are variations of these molecules that represent modifications having the same biological function. They can be naturally occurring variations, for example sequences from other organisms, or mutations that can either occur naturally or that have been introduced by specific mutagenesis. Furthermore, the variations can be synthetically produced sequences. The allelic variants can be either naturally occurring variants or synthetically produced variants or variants produced by recombinant DNA processes.

Generally, by means of conventional molecular biological processes it is possible (see, e.g., Sambrook et. al. (1989) loc. cit.) to introduce different mutations into the nucleic acid molecules of the invention. One possibility is the production of deletion mutants in which nucleic acid molecules are produced by continuous deletions from the 5'- or 3'-terminus of the coding DNA sequence and that lead to the synthesis of proteins that are shortened accordingly. Another possibility is the introduction of single-point mutation at positions where a modification of the amino acid sequence influences, e.g., the enzyme activity or the regulation of the enzyme. By this method muteins can be produced, for example, that possess a modified $K_m$-value or that are no longer subject to the regulation mechanisms that normally exist in the cell, e.g. with regard to allosteric regulation or covalent modification. Such muteins may be identified, e.g. by methods of the present invention, to be valuable as therapeutically useful modulators (inhibitors/antagonists or enhancer/agonists) of the activity of the proteins of the present invention.

Nucleic acid molecules that hybridize to polynucleotides of the invention can be isolated, e.g., from genomic or cDNA libraries. In order to identify and isolate such nucleic acid molecules the polynucleotides of the invention or parts of these polynucleotides or the reverse complements of these polynucleotides can be used, for example by means of hybridization according to conventional methods (see, e.g., Sambrook (1989), loc. cit.). As a hybridization probe nucleic acid molecules can be used, for example, that have exactly or basically the nucleotide sequence of a part of the sequence shown in SEQ ID No: 1 or sequences complementary thereto. The fragments used as hybridization probe can be synthetic fragments that were produced by means of conventional synthesis methods and the sequence of which basically corresponds to the sequence of a nucleic acid molecule of the invention. Preferably, the nucleic acid molecule of the invention is DNA or RNA.

An alternative embodiment of the invention relates to a vector comprising an above defined nucleotide acid molecule.

The vector of the present invention may be, e.g., a plasmid, phagemid, cosmid, fosmid, BAC, virus, bacteriophage or another vector used e.g. conventionally in genetic engineering, and may comprise further genes such as marker genes which allow for the selection of said vector in a suitable hosts and under suitable conditions.

Furthermore, the vector of the present invention may, in addition to the nucleic acid molecule of the invention, comprise expression control elements, allowing proper expression of the coding regions in suitable hosts. Such control elements are known to the artisan and may include a promoter, a splice cassette, translation initiation codon, translation and insertion site for introducing an insert into the vector. Preferably, the nucleic acid molecule of the invention is operably linked to said expression control sequences allowing expression in eukaryotic or prokaryotic cells. Many suitable vectors are known to those skilled in molecular biology, the choice of which would depend on the function desired and include plasmids, phagemid, cosmids, fosmid, BAC, virus, bacteriophages and other vectors used conventionally in genetic engineering. Methods which are well known to those skilled in the art can be used to construct various plasmids and vectors; see, for example, the techniques described in Sambrook (1989) loc. cit. and Ausubel (1998) loc. cit. Alternatively, the nucleic acid molecule and vectors of the invention can be reconstituted into liposomes for delivery to target cells. Thus, according to the invention relevant sequences can be transferred into expression vectors where expression of a particular (poly)peptide/protein is required. Typical cloning vectors include pBscpt sk, pGEM, pUC9, pBR322 and pGBT9. Typical expression vectors include pTRE, pCAL-n-EK, pESP-1, pOP13CAT. Typical prokaryotic cloning and expression vectors include: plasmid vectors like the pUC series (e.g. pUC18, pUC19), pGEM series (e.g. pGEM 7zf+, Promega, USA), pET series (e.g. pET22B, Novagen, USA), pBBC 1MCS series, pNOF (GL Biotech Germany), pCR-TOPO series and pCR Blunt (Invitrogen, USA), pBluescript series, pCAL series and pBCk series (Stratagene, USA); Fosmid vectors like pEpifos5 and pCC1 (Epicentre, USA); Cosmid vectors like the Expand series (Expand I, II, III) (Roche, Germany), SuperCos (Stratagene, USA), pOJ436; BAC vectors like pBeloBAC, pCC1BAC (Epicentre, USA). However, the present invention also envisages the expression of nucleic acid molecules as disclosed herein in eukaryotic vectors. Preferably, said nucleic acid molecules are linked to "control sequences". Said linking may be direct or indirect and refers, preferably to an operable linkage.

The term "control sequence" refers to regulatory DNA sequences which are necessary to effect the expression of coding sequences to which they are ligated. The nature of such control sequences differs depending upon the host organism. In prokaryotes, control sequences generally include promoter, ribosomal binding site, and terminators. In eukaryotes generally control sequences include promoters, terminators and, in some instances, enhancers, transactivators or transcription factors. The term "control sequence" is intended to include, at a minimum, all components the presence of which are necessary for expression, and may also include additional advantageous components.

The term "operably linked" refers to a juxtaposition wherein the components so described are in a relationship permitting them to function in their intended manner. A control sequence "operably linked" to a coding sequence is ligated in such a way that expression of the coding sequence is achieved under conditions compatible with the control sequences. In case the control sequence is a promoter, it is obvious for a skilled person that double-stranded nucleic acid is preferably used.

Thus, the vector of the invention is preferably an expression vector. An "expression vector" is a construct that can be used to transform a selected host cell and provides for expression of a coding sequence in the selected host. Expression vectors can for instance be cloning vectors, binary vectors or integrating vectors. Expression comprises transcription of the nucleic acid molecule preferably into a translatable mRNA. Regulatory elements ensuring expression in prokaryotes and/or eukaryotic cells are well known to those skilled in the art. In the case of eukaryotic cells they comprise normally promoters ensuring initiation of transcription and optionally poly-A signals ensuring termination of transcription and stabilization of the transcript. Possible regulatory elements permitting expression in prokaryotic hosts comprise, e.g., the PL, lac, trp or tac promoter in *E. coli*, and examples of regulatory elements permitting expression in eukaryotic host cells are the AOX1 or GAL1 promoter in yeast or the CMV-, SV40-, RSV-promoter (Rous sarcoma virus), CMV-enhancer, SV40-enhancer or a globin intron in mammalian and other animal cells. In this context, suitable expression vectors are known in the art such as Okayama-Berg cDNA expression vector pcDV1 (Pharmacia), pCDM8, pRc/CMV, pcDNA1, pcDNA3 (In-vitrogene), pSPORT1 (GIBCO BRL). Typical prokaryotic cloning and expression vectors include: plasmid vectors like the pUC series (e.g. pUC18, pUC19), pGEM series (e.g. pGEM 7zf+, Promega, USA), pET series (e.g. pET22B, Novagen, USA), pBBC 1MCS series, pNOF (GL Biotech Germany), pCR-TOPO series and pCR Blunt (Invitrogen, USA), pBluescript series, pCAL series and pBC series (Stratagene, USA); Fosmid vectors like pEpifos5 and pCC1 (Epicentre, USA); Cosmid vectors like the Expand series (Expand I, II, III) (Roche, Germany), SuperCos (Stratagene, USA), pOJ436; BAC vectors like pBeloBAC, pCC1BAC (Epicentre, USA).

An alternative expression system which could be used to express a cell cycle interacting protein is an insect system. In one such system, *Autographa californica* nuclear polyhedrosis virus (AcNPV) is used as a vector to express foreign genes in *Spodoptera frugiperda* cells or in *Trichoplusia larvae*. The coding sequence of a nucleic acid molecule of the invention may be cloned into a nonessential region of the virus, such as the polyhedrin gene, and placed under control of the polyhedrin promoter. Successful insertion of said coding sequence will render the polyhedrin gene inactive and produce recombinant virus lacking coat protein coat. The recombinant viruses are then used to infect *S. frugiperda* cells or *Trichoplusia larvae* in which the protein of the invention is expressed (Smith, J. Virol. 46 (1983), 584; Engelhard, Proc. Nat. Acad. Sci. USA 91 (1994), 3224-3227.

In plants, promoters commonly used are the polyubiquitin promoter, and the actin promoter for ubiquitous expression. The termination signals usually employed are from the Nopaline Synthase promoter or from the CAMV 35S promoter. A plant translational enhancer often used is the TMV omega sequences, the inclusion of an intron (Intron-1 from the Shrunken gene of maize, for example) has been shown to increase expression levels by up to 100-fold. (Mait, Transgenic Research 6 (1997), 143-156; Ni, Plant Journal 7 (1995), 661-676). Additional regulatory elements may include transcriptional as well as translational enhancers. Advantageously, the above-described vectors of the invention comprises a selectable and/or scorable marker. Selectable marker genes useful for the selection of transformed cells and, e.g., plant tissue and plants are well known to those skilled in the art and comprise, for example, antimetabolite resistance as the basis of selection for dhfr, which confers resistance to methotrexate (Reiss, Plant Physiol. (Life Sci. Adv.) 13 (1994), 143-149); npt, which confers resistance to the aminoglycosides neomycin, kanamycin and paromycin (Herrera-Estrella, EMBO J. 2 (1983), 987-995) and hygro, which confers resistance to hygromycin (Marsh, Gene 32 (1984), 481-485). Additional selectable genes have been described, namely trpB, which allows cells to utilize indole in place of tryptophan; hisD, which allows cells to utilize histinol in place of histidine (Hartman, Proc. Natl. Acad. Sci. USA 85 (1988), 8047); mannose-6-phosphate isomerase which allows cells to utilize mannose (WO 94/20627) and ODC (ornithine decarboxylase) which confers resistance to the ornithine decarboxylase inhibitor, 2-(difluoromethyl)-DL-ornithine, DFMO (McConlogue, 1987, In: Current Communications in Molecular Biology, Cold Spring Harbor Laboratory ed.) or deaminase from *Aspergillus terreus* which confers resistance to Blasticidin S (Tamura, Biosci. Biotechnol. Biochem. 59 (1995), 2336-2338).

Useful scorable marker are also known to those skilled in the art and are commercially available. Advantageously, said marker is a gene encoding luciferase (Giacomin, Pl. Sci. 116 (1996), 59-72; Scikantha, J. Bact. 178 (1996), 121), green fluorescent protein (Gerdes, FEBS Lett. 389 (1996), 44-47), β-glucuronidase (Jefferson, EMBO J. 6 (1987), 3901-3907) or secreted alkaline phosphatase (SEAP) (Schlatter et al. (2001) Biotechnol Bioeng. 5, 75(5), 597-606). This embodiment is particularly useful for simple and rapid screening of cells, tissues and organisms containing a vector of the invention.

The present invention furthermore relates to host containing an aforementioned vector or an aforementioned nucleic acid molecule. Said host may be produced by introducing said vector or nucleotide sequence into the host by transfection or transformation wherein the nucleotide sequence and/or the encoded (poly)peptide/protein is foreign to the host. Upon the presence of said vector or nucleotide sequence in the host the expression of a protein encoded by the nucleotide sequence of the invention or comprising a nucleotide sequence or a vector according to the invention is mediated.

By "foreign" it is meant that the nucleotide sequence and/or the encoded (poly)peptide/protein is either heterologous with respect to the host, this means derived from a cell or organism with a different genomic background, or is homologous with respect to the host but located in a different genomic environment than the naturally occurring counterpart of said nucleotide sequence. This means that, if the nucleotide sequence is homologous with respect to the host, it is not located in its natural location in the genome of said host, in particular it is surrounded by different genes. In this case the nucleotide sequence may be either under the control of its own promoter or under the control of a heterologous promoter. The vector or nucleotide sequence according to the invention which is present in the host may either be integrated into the genome of the host or it may be maintained in some form extrachromosomally. In this respect, it is also to be understood that the nucleotide sequence of the invention can be used to restore or create a mutant gene via homologous recombination.

Moreover, the present invention related to a method for producing a (poly)peptide as encoded by a nucleic acid molecule of the invention, comprising culturing the host of the invention under suitable conditions and isolating said (poly)peptide from the culture.

Isolation and purification of the recombinantly produced proteins and (poly)peptides may be carried out by conventional means including preparative chromatography and affinity and immunological separations involving affinity chromatography with monoclonal or polyclonal antibodies specifically interacting with said proteins/(poly)peptides. Preferably, said antibodies are antibodies of the invention as described herein below.

As used herein, the term "isolated protein" includes proteins substantially free of other proteins, nucleic acids, lipids, carbohydrates or other materials with which it is naturally associated. Such proteins however not only comprise recombinantly produced proteins but include isolated naturally occurring proteins, synthetically produced proteins, or proteins produced by a combination of these methods. Means for preparing such proteins are well understood in the art. The proteins of the invention are preferably in a substantially purified form. A recombinantly produced version of said proteins, including secreted proteins, can be substantially purified by the one-step method described in Smith and Johnson, 1988.

An alternative embodiment of the invention relates to a (poly)peptide encoded by a nucleic acid molecule of the invention or as obtained by the method of the invention.

Preferably said (poly)peptide or fragment thereof is glycosylated, phosphorylated, amidated and/or myristylated.

Furthermore, the present invention relates to an antibody or an aptamer specifically recognizing the aforementioned (poly)peptide or a fragment or epitope thereof. Said antibody may be a monoclonal or a polyclonal antibody.

The term "fragment thereof" as used herein refers to fragments of said (poly)peptide/protein which are characterized by their capability to induce an immunological response in an immunized organism. Said response may be induced by the protein or fragment thereof either alone or in combination with a hapten, an adjuvant or other compounds known in the art to induce or elicit immunoresponses to a protein or fragment thereof.

The term "epitope" defines a single antigenic determinant. Said determinant is at least a portion of an antigen to which e.g. an antibody specifically binds to by its paratope; see Roitt et. al. (1993) Immunology 3rd edition, Mosby.

A preferred embodiment of the invention relates to an antibody which is a monoclonal antibody.

Said antibody, which is monoclonal antibody, polyclonal antibody, single chain antibody, or fragment thereof that specifically binds said peptide or polypeptide also including bispecific antibody, synthetic antibody, antibody fragment, such as Fab, a $F(ab_2)'$, Fv or scFv fragments etc., or a chemically modified derivative of any of these (all comprised by the term "antibody"). Monoclonal antibodies can be prepared, for example, by the techniques as originally described in Köhler and Milstein, Nature 256 (1975), 495, and Galfré, Meth. Enzymol. 73 (1981), 3, which comprise the fusion of mouse myeloma cells to spleen cells derived from immunized mammals with modifications developed by the art. Furthermore, antibodies or fragments thereof to the aforementioned peptides can be obtained by using methods which are described, e.g., in Harlow and Lane "Antibodies, A Laboratory Manual", CSH Press, Cold Spring Harbor, 1988. When derivatives of said antibodies are obtained by the phage display technique, surface plasmon resonance as employed in the BIAcore system can be used to increase the efficiency of phage antibodies which bind to an epitope of the peptide or polypeptide of the invention (Schier, Human Antibodies Hybridomas 7 (1996), 97-105; Malmborg, J. Immunol. Methods 183 (1995), 7-13). The production of chimeric antibodies is described, for example, in WO89/09622. A further source of antibodies to be utilized in accordance with the present invention are so-called xenogenic antibodies. The general principle for the production of xenogenic antibodies such as human antibodies in mice is described in, e.g., WO 91/10741, WO 94/02602, WO 96/34096 and WO 96/33735. Antibodies to be employed in accordance with the invention or their corresponding immunoglobulin chain(s) can be further modified using conventional techniques known in the art, for example, by using amino acid deletion(s), insertion(s), substitution(s), addition(s), and/or recombination(s) and/or any other modification(s) known in the art either alone or in combination. Methods for introducing such modifications in the DNA sequence underlying the amino acid sequence of an immunoglobulin chain are well known to the person skilled in the art; see, e.g., Sambrook (1989), loc. cit.

The term "monoclonal" or "polyclonal antibody" (see Harlow and Lane, (1988), loc. cit.) also relates to derivatives of said antibodies which retain or essentially retain their binding specificity. Whereas particularly preferred embodiments of said derivatives are specified further herein below, other preferred derivatives of such antibodies are chimeric antibodies comprising, for example, a mouse or rat variable region and a human constant region.

The term "scFv fragment" (single-chain Fv fragment) is well understood in the art and preferred due to its small size and the possibility to recombinantly produce such fragments.

The term "specifically binds" in connection with the antibody used in accordance with the present invention means that the antibody etc. does not or essentially does not cross-react with (poly)peptides of similar structures. Cross-reactivity of a panel of antibodies etc. under investigation may be tested, for example, by assessing binding of said panel of antibodies etc. under conventional conditions (see, e.g., Harlow and Lane, (1988), loc. cit.) to the (poly)peptide of interest as well as to a number of more or less (structurally and/or functionally) closely related (poly)peptides. Only those antibodies that bind to the (poly)peptide/protein of interest but do not or do not essentially bind to any of the other (poly) peptides which are preferably expressed by the same organism/tissue as the (poly)peptide of interest, e.g. by a crenarchaeote, are considered specific for the (poly)peptide/protein of interest and selected for further studies in accordance with the method of the invention.

In a further alternative embodiment the present invention relates to a transgenic non-human mammal whose somatic and germ cells comprise at least one gene encoding a functional polypeptide selected from the group consisting of:

(a) the polypeptide of the invention;

(b) a polypeptide having an amino acid sequence that is at least 60%, preferably at least 80%, especially at least 90%, advantageously at least 99% identical to the amino acid sequence of (a); and (c) a polypeptide having the amino acid sequence of (a) with at least one conservative amino acid substitution.

A method for the production of a transgenic non-human animal, for example transgenic mouse, comprises introduction of the aforementioned polynucleotide or targeting vector into a germ cell, an embryonic cell, stem cell or an egg or a cell derived therefrom. The non-human animal can be used in accordance with the invention in a method for identification of compounds, described herein below. Production of transgenic embryos and screening of those can be performed, e.g., as described by A. L. Joyner Ed., Gene Targeting, A Practical Approach (1993), Oxford University Press. The DNA of the embryonal membranes of embryos can be analyzed using, e.g., Southern blots with an appropriate probe; see supra. A general method for making transgenic non-human animals is described in the art, see for example WO 94/24274. For making transgenic non-human organisms (which include homologously targeted non-human animals), embryonal stem cells (ES cells) are preferred. Murine ES cells, such as AB-1 line grown on mitotically inactive SNL76/7 cell feeder layers (McMahon and Bradley, Cell 62:1073-1085 (1990)) essentially as described (Robertson, E. J. (1987) in Teratocarcinomas and Embryonic Stem Cells: A Practical Approach. E. J. Robertson, ed. (Oxford: IRL Press), p. 71-112) may be used for homologous gene targeting. Other suitable ES lines include, but are not limited to, the E14 line (Hooper et al., Nature 326:292-295 (1987)), the D3 line (Doetschman et al., J. Embryol. Exp. Morph. 87:27-45 (1985)), the CCE line (Robertson et al., Nature 323:445-448 (1986)), the AK-7 line (Zhuang et al., Cell 77:875-884 (1994)). The success of generating a mouse line from ES cells bearing a specific targeted mutation depends on the pluripotence of the ES cells (i.e., their ability, once injected into a host developing embryo, such as a blastocyst or morula, to participate in embryogenesis and contribute to the germ cells of the resulting animal). The blastocysts containing the injected ES cells are allowed to develop in the uteri of pseudopregnant non-human females and are born, e.g. as chimeric mice. The resultant transgenic mice are chimeric for cells having either the recombinase or reporter loci and are backcrossed and screened for the presence of the correctly targeted transgene (s) by PCR or Southern blot analysis on tail biopsy DNA of offspring so as to identify transgenic mice heterozygous for either the recombinase or reporter locus/loci.

The transgenic non-human animals may, for example, be transgenic mice, rats, hamsters, dogs, monkeys, rabbits, pigs, or cows. Preferably, said transgenic non-human animal is a mouse.

The figures show:

Figure 1A:
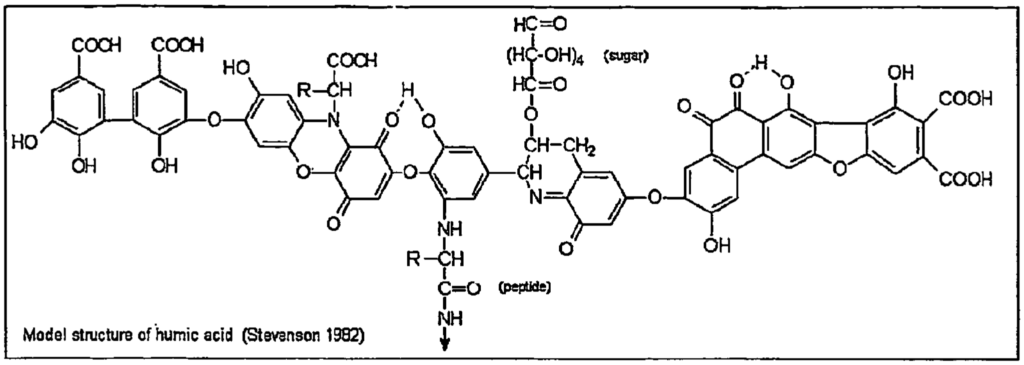
FIG. 1A shows the Structure of humic acids (after Stevenson 1982).
Figure 1B:
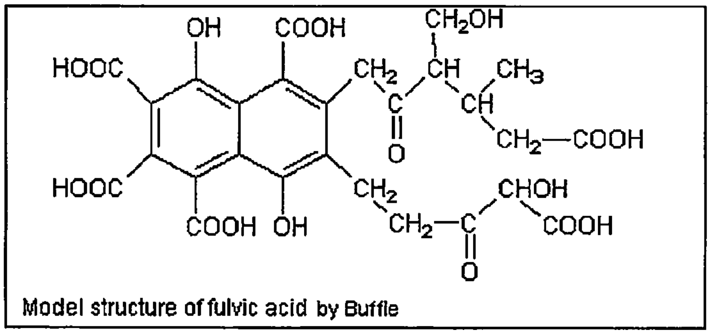
FIG. 1B shows the Structure of fulvic acids (after Buffle 1977).
Figure 2:
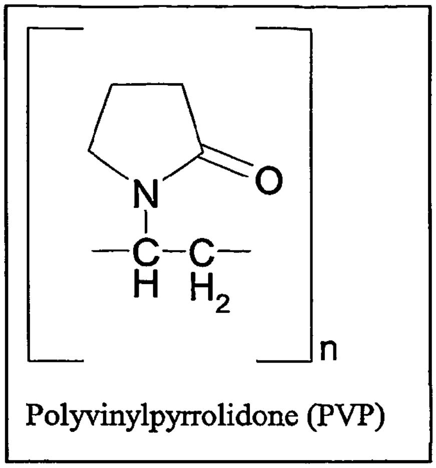
FIG. 2 shows the Structure of polyvinylpyrrolidone (Monomer)
Figure 3:
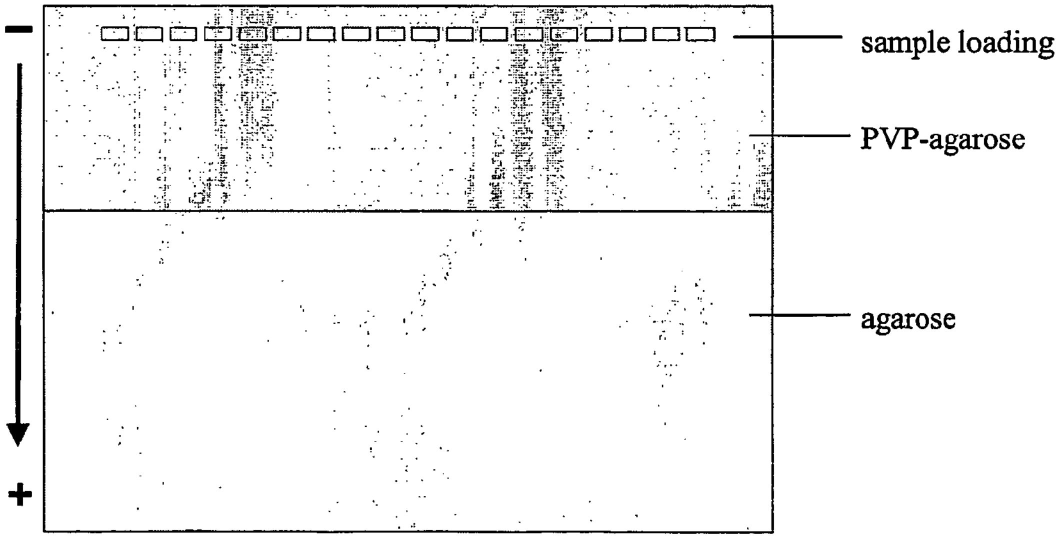

FIG. 3 shows an example of an 2-phase PVP-low-melting agarosegel for simultaneous DNA purification and size resolution (Discontinuous Affinity-Gelelectrophoresis, DAG). The PVP-agarose-phase (the first phase) typically takes up approximately ¼ to ⅓ of the gel but may take up maximally 80-95% of the gel. After migrating through the PVP-phase into the agarose-only phase gel segments containing DNA fragments of interesting size may be excised and appropriately treated. The DNA migrates from minus (−) to plus (+).

Figure 4:
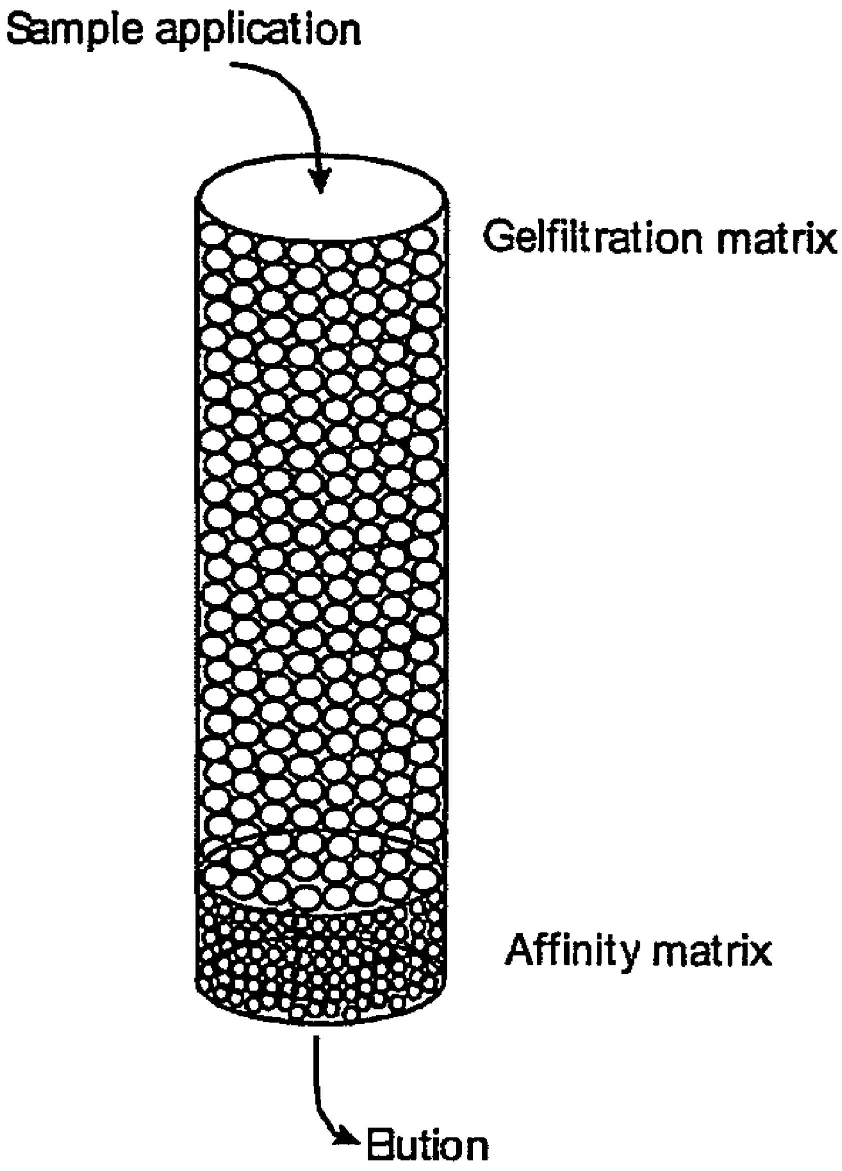

FIG. 4 shows an example of an 2-Phase Column chromatography for size resolution and affinity purification of DNA. In the first phase DNA in solution is resolved from inhibitors by size-exclusion chromatography. After passing this part of the composite column, the DNA passes a phase containing an affinity matrix (e.g. PVPP) to selectively bind and retard inhibitors. The DNA elutes from the column largest molecules first. The liquid flow is driven by hydrostatic or peristaltic pressure.

Figure 5:
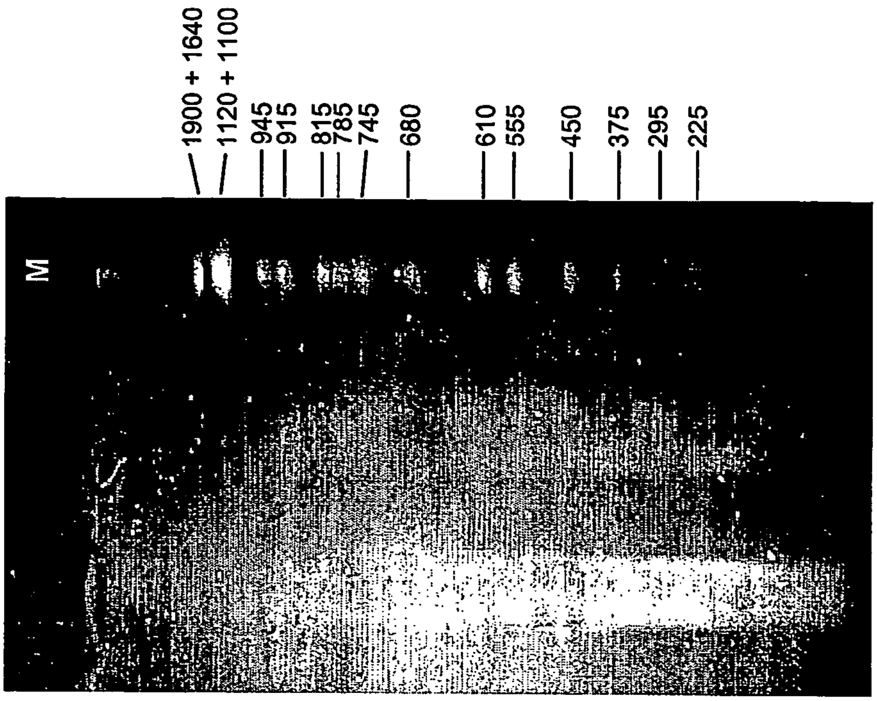
Figure 5:
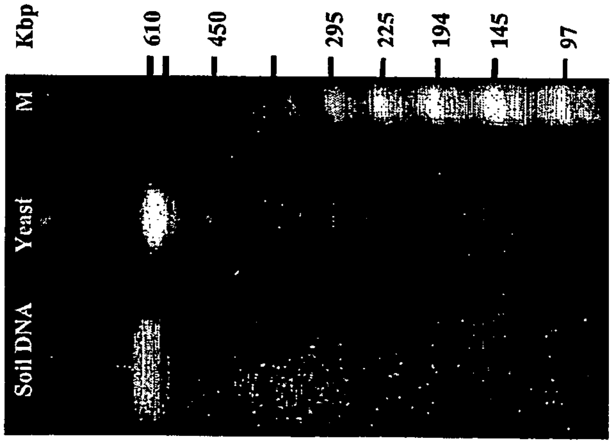

FIG. 5 shows pulsed-field gelelectrophoretic (PFGE-) separations of metagenomic DNA isolated from soil (method A). In FIG. 5 A the high molecular weight DNA is concentrated in a compression zone above 600 kbp. Yeast genomic DNA and a commercial size marker are added for reference. In FIG. 5B most DNA is sized to around 500 kbp but fragments up to 1.9 Mbp are visible.

M: Size marker (in kbp)

Figure 6:
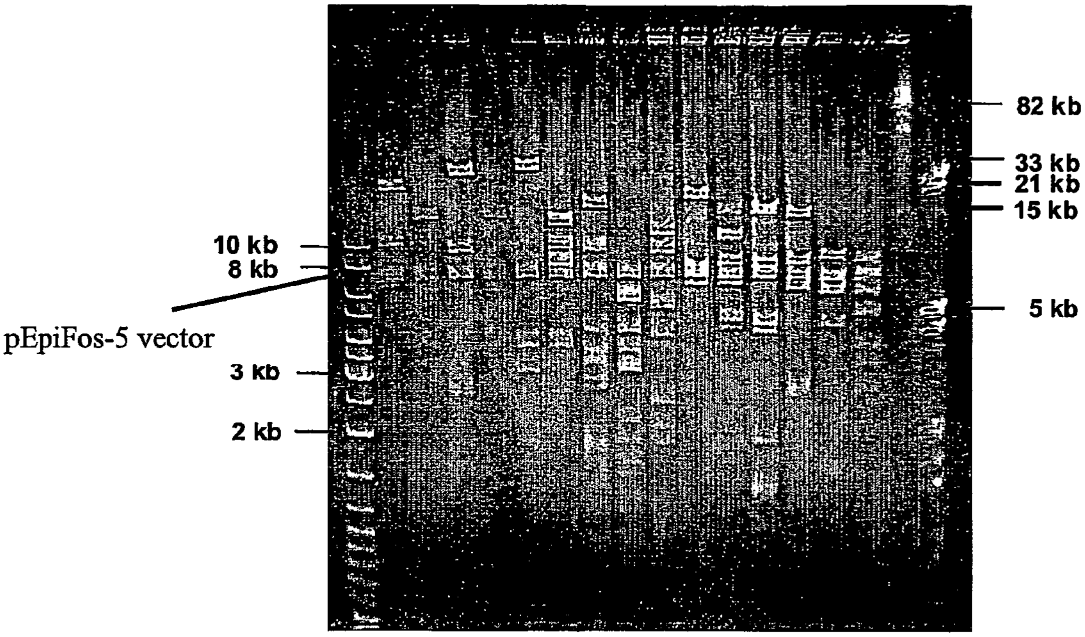

FIG. 6 shows an insert analysis of metagenomic clones containing soil-derived DNA. Clones were digested with Not I.

Figure 7:
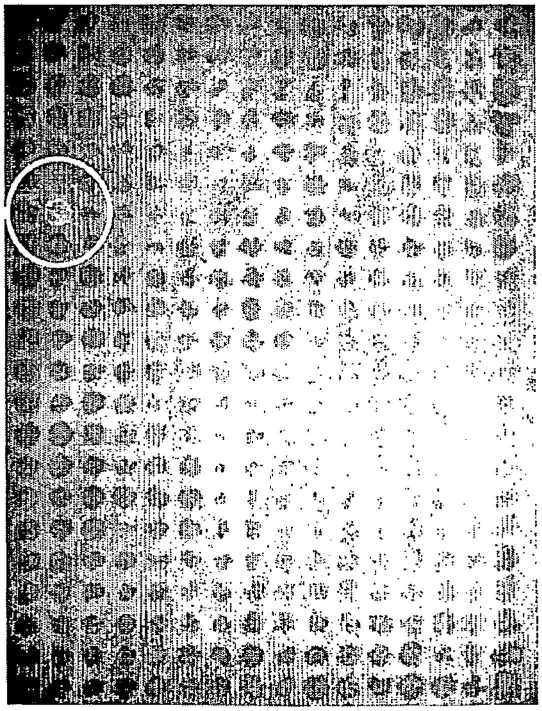

FIG. 7 shows an expression screening of arrayed fosmid clones containing metagenomic, soil-derived DNA. The encircled clone shows a halo of substrate degradation indicating hydrolase enzyme activity.

Figure 8:
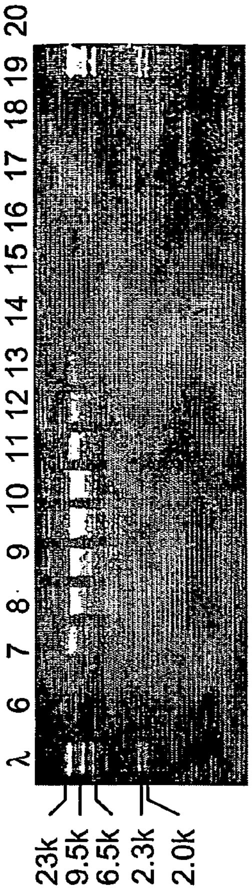
Figure 8B:
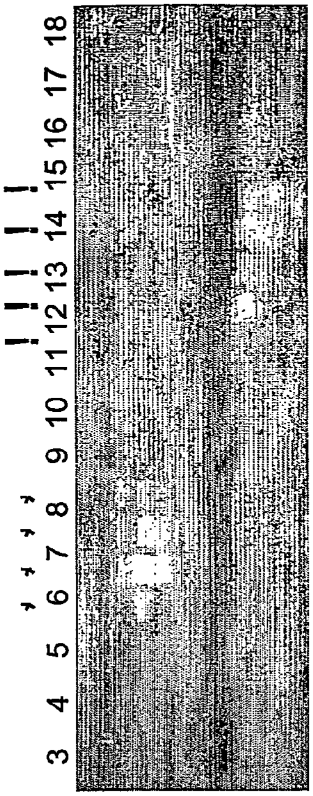

FIG. 8 shows the quantification of metagenomic soil DNA in fractions eluting from columns after PVPP/sepharose 2B chromatography.

FIG. 8 A: The DNA bands of fractions 6-22 were quantified by fluorescence intensity comparison after gel electrophoresis in a 1% agarose gel containing ethidium bromide. Gel documentation and analysis was done using GeneTools software from SynGene (UK). A 1% agarose gel was chosen to concentrate heterogenous DNA fragments in a single band for the sake of simplifying quantification. This was achieved yet at the price of size-resolution. The apparent comigration of eluting DNA with the 23 kbp marker band therefore is an underestimation of true maximum DNA fragment sizes. Lane 1: λ Hind III Marker DNA FIG. 8 B: Analysis of DNA in PVPP/sepharose 2B chromatography fractions by agarose gel electrophoresis

* indicates fractions containing pure DNA

! indicates fractions containing large amounts of humic acids

Figure 9:
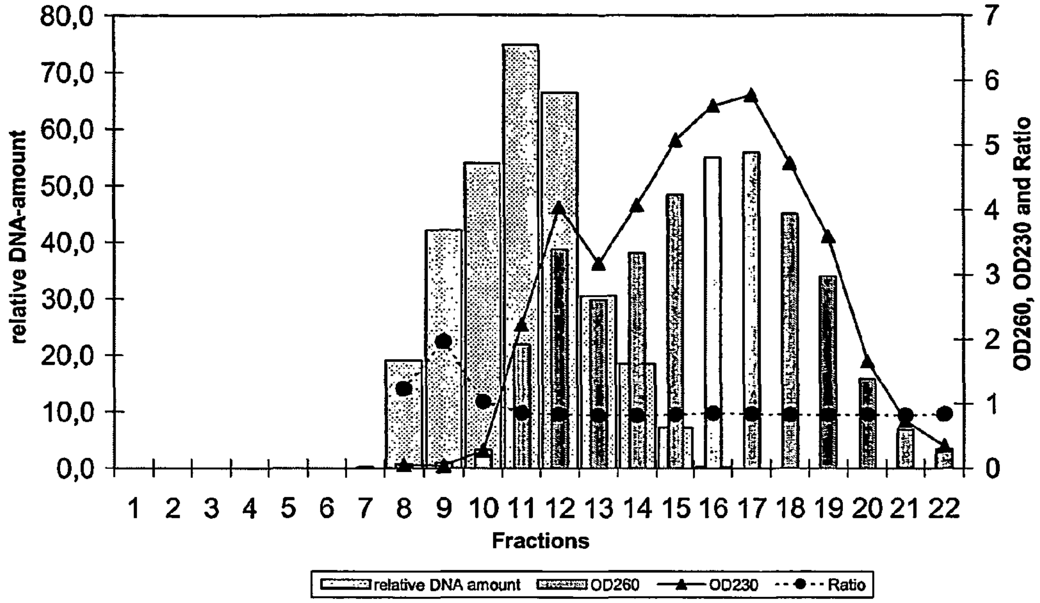
Figure 9:
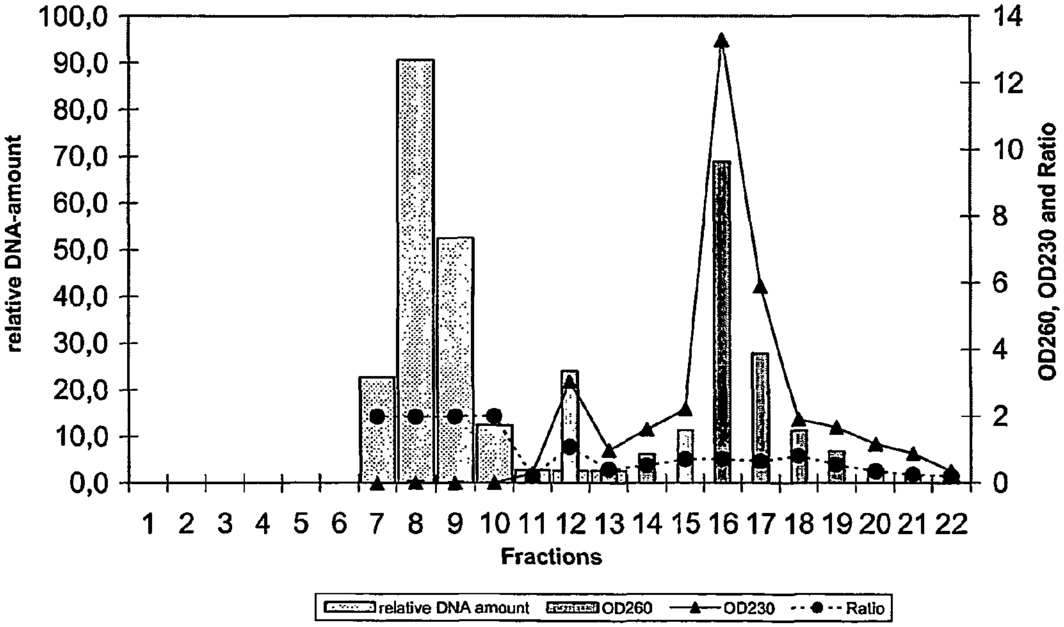

FIG. 9 shows the separation of soil metagenome DNA from humic substances by chromatography on PVPP/sepharose 2 B column.

FIG. 9 A: Spectral absorption of eluting fractions 1-22 at 260 (DNA and humic acids) and 230 nm (humic acids) are plotted along their ratio and the relative DNA amounts as determined by agarose gel electrophoresis (see FIG. 8). A high A260/A230 ratio indicates pure DNA with low humic/fulvic acid contamination as can be seen in fractions 8 and 9. Absorption at 260 nm and 230 nm rises in two peaks in later fractions (12 and 17) possibly due to two size-populations of humic acids.

FIG. 9 B: The result of a corresponding experiment is shown in FIG. 9 B. Microbial DNA from humic substances in crude extract from soil is separated by PVPP/sepharose 2B chromatography. The gel electrophoratic analysis of fractions derived from this separation as described for FIG. 9 A FIG. 10: Restriction digest (NotI) of randomly selected environmental fosmid clones separated by pulse field gel electrophoresis. Lanes 1,2: DNA size standards. A band of 7.5 kb visible in all lanes corresponds to the fosmid vector.

Figure 11:
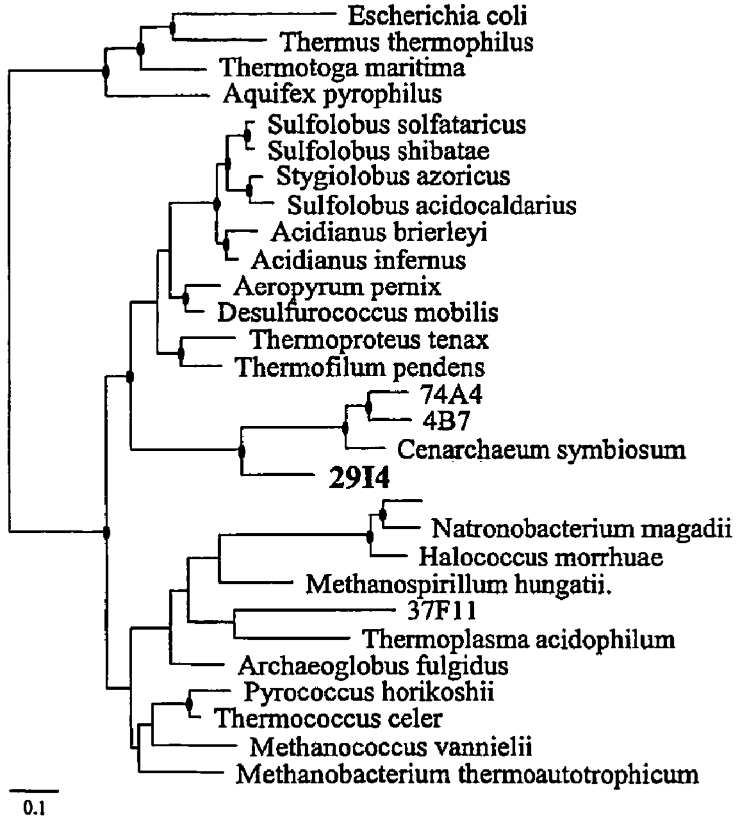

FIG. 11: Phylogenetic tree based on full-length 23S rDNA sequences of Bacteria, Archaea and of sequences obtained from marine environmental genomic clones. Different alignment filters were used to evaluate the phylogenetic reconstruction. The tree topology shown here is based on a maximum parsimony analysis (using 1048 conserved positions selected by a positional variability filter). Closed circles indicate branching points supported by different phylogenetic methods and filters in reconstructions with the 23S and the corresponding 16S rDNA tree (see Experimental Procedures in appended example 5).

Figure 12:
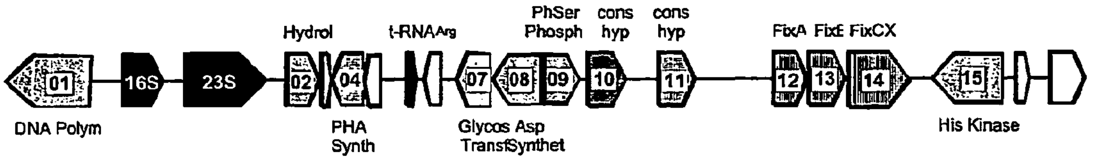

FIG. 12: Schematic representation of the archaeal fosmid clone 29i4/SEQ ID NO: 1. Different shadings indicate the phylogenetic affinity of the putative protein-coding genes to archaea (diag. stripes), bacteria (dots), bacteria and archaea (vertical stripes), or archaea, bacteria and eukarya (grey). Hypothetical genes with no homologs are shown without fillings. ORF numbers match those in Table 1.

Figure 13:
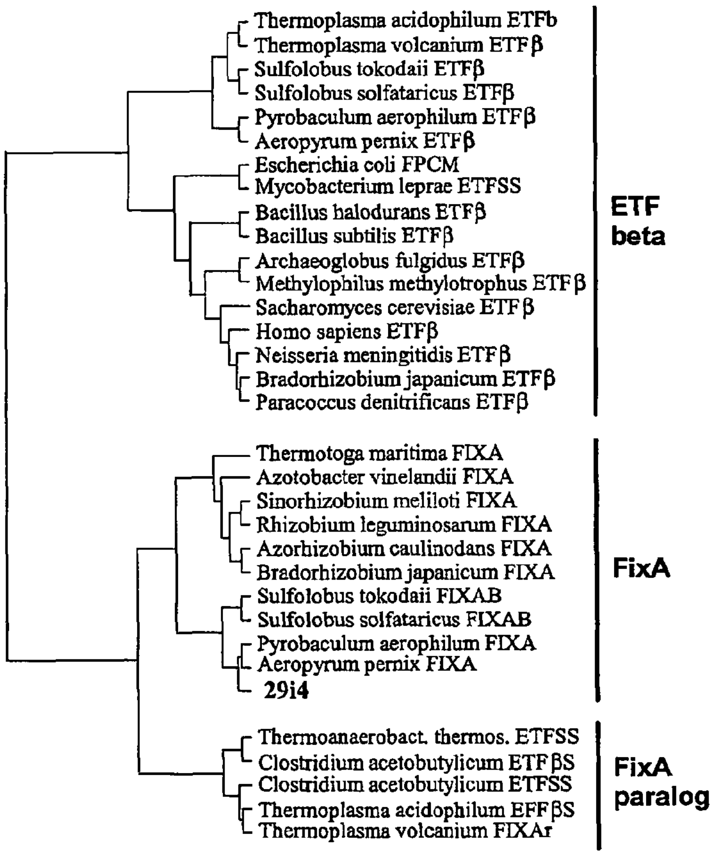

FIG. 13: Phylogenetic analysis with selected sequences of the ETF-like protein family. Homologs of FixA proteins from archaea form a monophyletic group with the FixA proteins of nitrogen fixing bacteria and of *Thermotoga maritima*, clearly distinguished from "housekeeping" ETF proteins (Etfβ homologs) of bacteria, archaea and eukaryotes. A third distinct subgroup (termed FixA paralog) is formed by a few as yet uncharacterized sequences from bacteria and archaea. For details of the phylogenetic reconstruction see Experimental Procedures in appended example 5.

Figure 14:
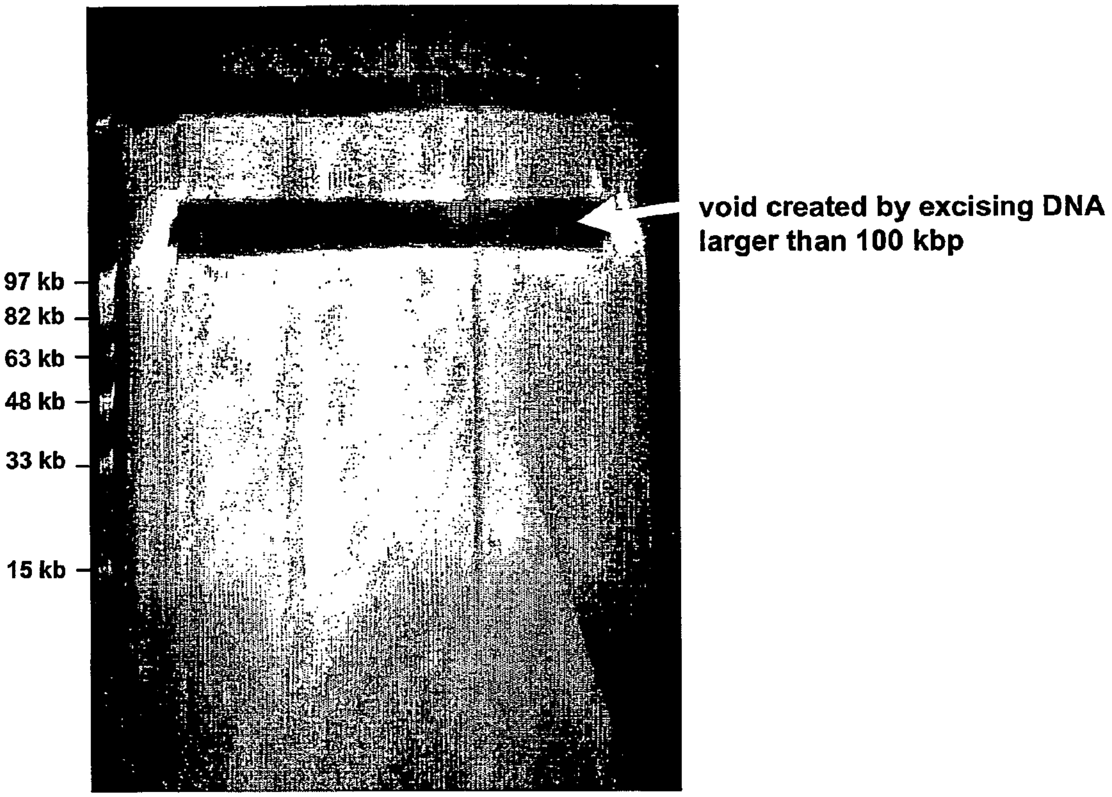
Figure 14:
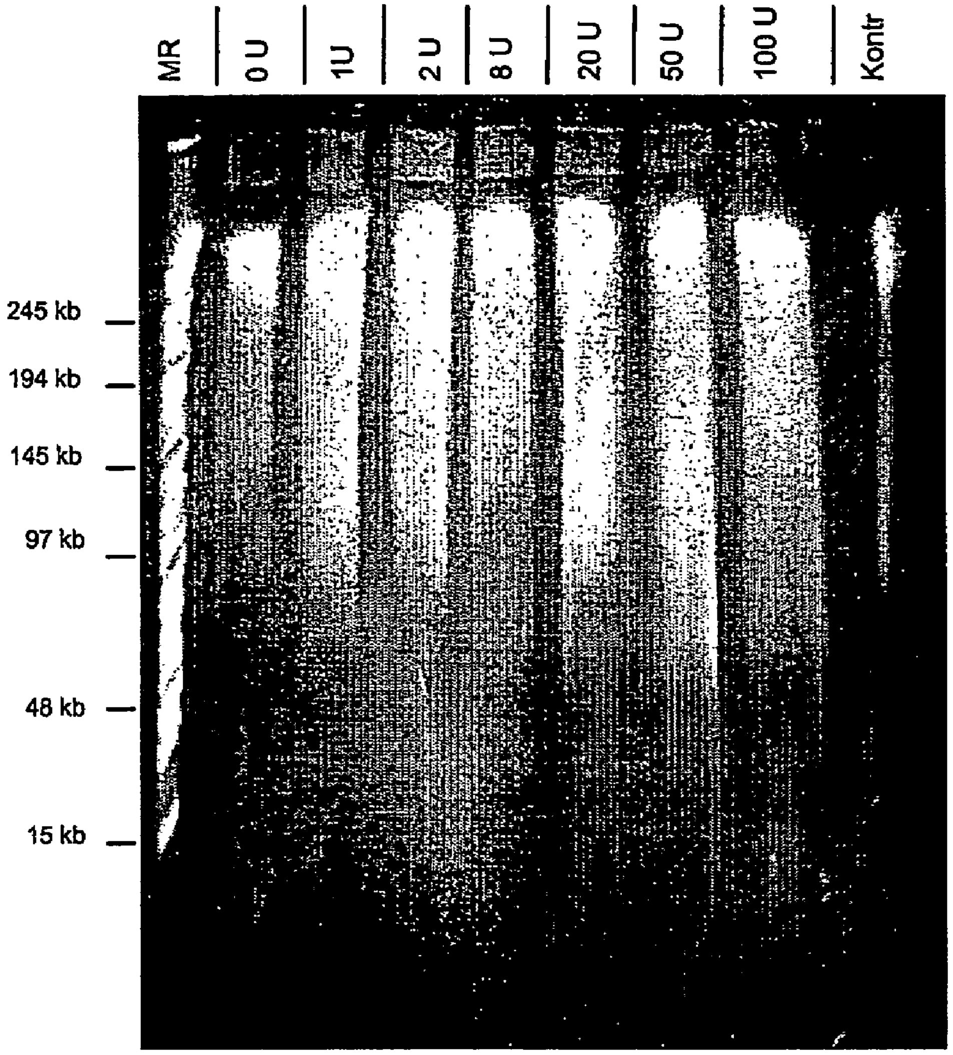
Figure 14:
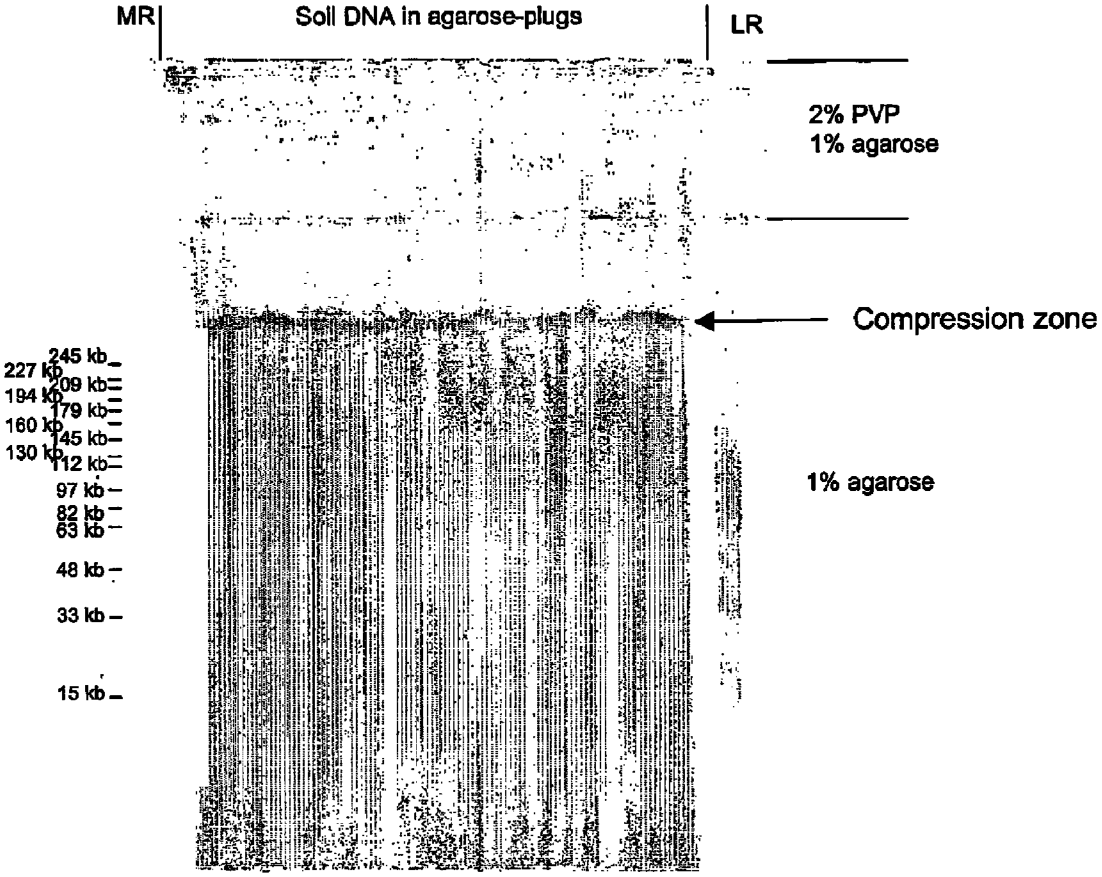
Figure 14:
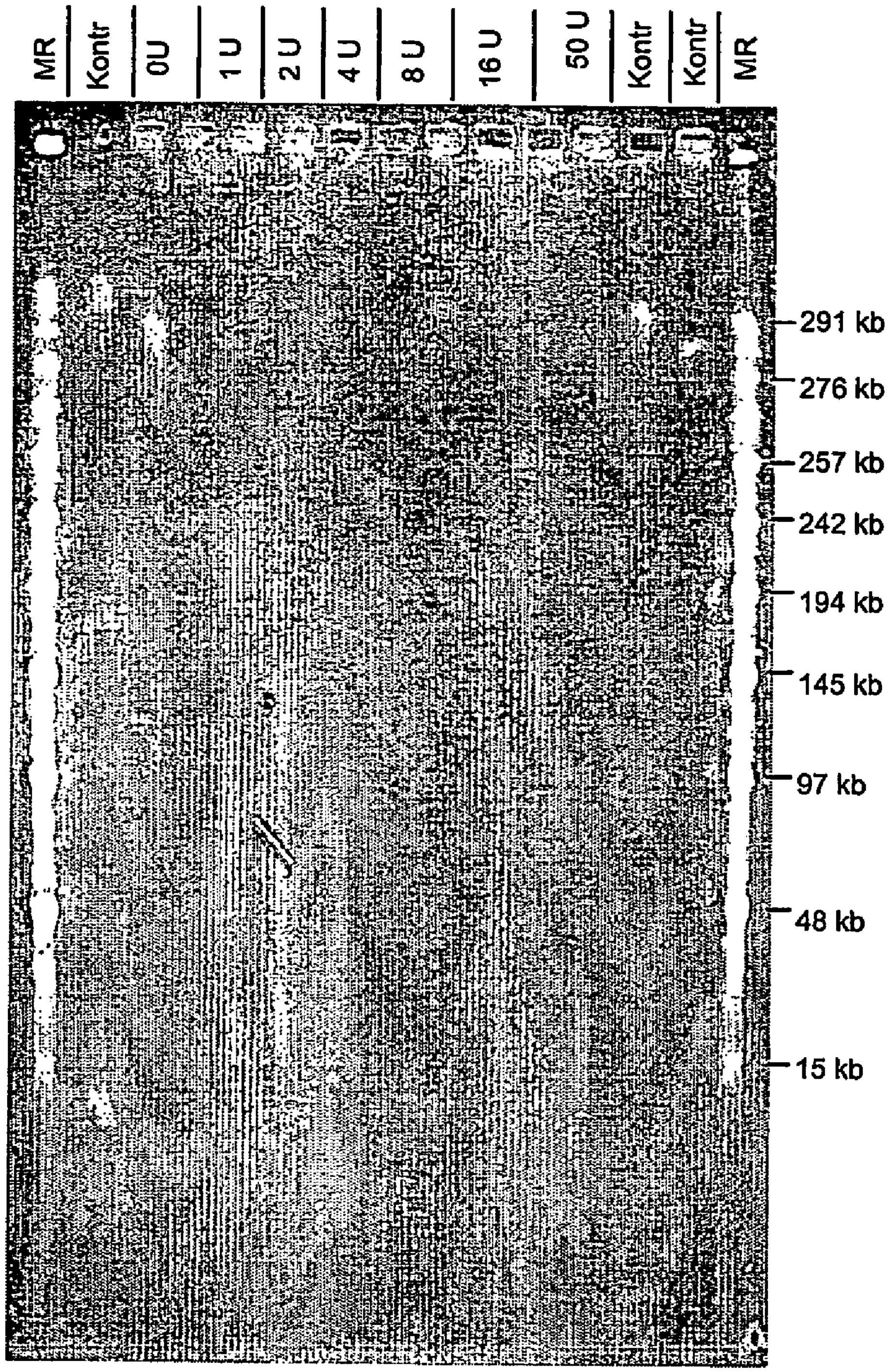

FIG. 14:

FIG. 14 A: Size selection of soil DNA in a standard agarose gel

Preparative standard PFGE gel (EtBr stained) separation of soil DNA. The compression zone above 100 kbp was excised and resulting agarose plugs subsequently subjected to enzymatic digestion to test purity and clonability (FIG. 14 B).

FIG. 14 B: Failed hydrolyses of soil DNA (HindIII) purified in a standard agarose gel Analytical PFGE showing DNA from an enzyme titration experiment (EtBr stained). DNA containing cubic plugs cut out from a standard PFGE agarose gel (FIG. 14 A) and containing fragments sized over 100 kb were added to a reaction mix containing increasing units of HindIII restriction enzyme. After terminating the reaction the DNA was re-run on a second PFGE. It is evident from the similarly undigested DNA at 0 U and at 100 U enzyme concentration that this DNA is highly resistant to digestion with Hind III indicating inhibiting impurities that prevent molecular manipulation and cloning.

FIG. 14 C: Size selection and purification of soil DNA in a 2-phase gel

Preparative 2-phase PFGE gel (SYBR green stained, inverted image) purification of soil DNA. The compression zone of DNA above 250 kbp was excised and subsequently subjected to enzymatic digestion as a proof of purity and clonability (FIG. 14 D).

FIG. 14 D: Successful partial hydrolyses of soil DNA (HindIII) purified in a 2-phase gel Analytical PFGE showing soil DNA from an enzyme titration experiment (EtBr stained). 2-phase gel purified soil DNA cut out from a preparative 2-Phase Gel (FIG. 14 C) and sized over 280 kb was Hind III digested and re-run on a second PFGE. It is evident that after purification in the 2-phase gel the DNA is readily digested to smaller sizes even with as little as 1 U Hind III indicating a high degree of purity and access by enzymes necessary for subsequent molecular cloning.

EXAMPLES

The following examples illustrate the invention. These examples should not be construed as limiting: the examples are included for purposes of illustration and the present invention is limited only by the claims.

Example 1

Generation of a Fosmid Library from Soil Metagenomic DNA 1.1 Preparation of High Molecular Weight DNA from Soil (A)

Soil was collected from the upper layer of a partially ruderalized sandy ecosystem in Weiterstadt (Germany). About 50 g were suspended in 300 ml of buffer (pH 8, 20 mM Tris-HCl, 10 mM ϵ-aminocaproic acid, 10 mM EDTA) and incubated at 4° C. for 15 h with gentle shaking. The suspension was sieved to remove larger particles and after centrifugation of the filtrate (5000×g 30 min.) the resulting microbial fraction was embedded in agarose plugs (0.5% low-melting SEAPlaque, FMC Bioproducts). The plugs were incubated at 37° C. for 1 hour in lysozyme buffer (100 mM EDTA pH 8.0, 10 mM Tris-HCl pH 8.0, 50 mM NaCl, 0.2% Na-deoxycholate, 1% laurylsarcosin, 2 mg/ml lysozyme), then transferred into ESP solution containing 2 mg/ml proteinase K, 1% lauroyl Sarcosin and 0.5 M EDTA and incubated at 50° C. for 24 h under gentle rotation and with 1 exchange of ESP buffer. 3 agarose plugs were placed in a 1% agarose gel (Sigma A-2929) that contained 2% PVP (Sigma PVP-360) in the upper part and no PVP in the lower part. Pulsed-field electrophoresis was performed in a CHEF-DR II PFGE machine (BioRad) at 10° C., 6 V cm-1 for 20 h with 1 to 4 s pulses (FIG. 5). A slice of agarose containing DNA in the size range of >30 kbp was cut out of the gel inserted into appropriately sized slots in a second gel and re-electrophoresed for a second size selection. After electroelution the resulting DNA was dialyzed and concentrated in a microconcentrator (Vivascience).

1.2 Preparation of High Molecular Weight DNA from Soil (B)

Alternatively total soil DNA was extracted using a protocol modified from Zhou and coworkers (Zhou et al., (1996) loc. cit.). Soil (5 g) was resuspended in 13.5 ml extractionbuffer (100 mM Tris/HCl pH8.0, 100 mM Na-EDTA, 100 mM Na-phosphate pH 8.0, 1.5 M NaCl, 1% CTAB) followed by an optional 3 cycles of freezing in liquid nitrogen and boiling in a microwave oven. After adding 1.5 ml of lysozyme solution (50 mg/ml) and 30 min. incubation at 37° C., 200 µl proteinase K solution (10 mg/ml) were added followed by another 30 min. incubation at 37° C. Then 3 ml 10% SDS was added followed bei 2 hours incubation at 65° C. After centrifugation (10 min., 6000×g, room temperature) the supernatant was collected and the pellet reextracted twice for 10 min. at 65° C. with 4.5 ml of extraction buffer and 1 ml of 10% SDS. All supernatants were united and extracted with an equal volume of chloroform/isoamylalcohol (24:1 vol/vol). DNA was precipitated from the aqueous phase with 0.6 vol isopropanol, pelleted by centrifugation (16000×g, 20 min., room temperature), washed in 70% ethanol and dissolved in 200 µl TE buffer (10 mM Tris-HCl pH 8.0, 1 mM EDTA). Depending on the soil sample this solution was yellowish to dark brown. This DNA routinely defied any enzymatic manipulation by restriction enzymes and could be successfully used for PCR only at dilutions below 1/1000. It was therefore electrophoresed either in a constant voltage electrophoresis using a 0.5% agarose 2-phase gel with 2% PVP in the first phase (4 hours at 60 V) or in a 2-phase PFGE gel as described in (A).

Example 2

Library Construction and Analysis

About 0.5 µg of purified DNA was enzymatically treated to prepare 5' phosphorylated blunt ends and was ligated to the linearized and dephosphorylated fosmid vector pEpiFOS-5 (pEpiFOS Fosmid Library Production Kit, Epicentre). After in vitro packaging into lambda phages (Epicentre) and infection of *E. coli* strain EPI100 (Epicentre), cells were plated on LB medium containing 12.5 µg/ml chloramphenicol. The colonies were transferred to individual wells of 384-well microtitre plates containing 50 µl of LB with 12.5 µg/ml chloramphenicol and 7% glycerol (v/v) and were incubated at 37° C. for 24 hours. The library was stored at −80° C.

After blunt-end cloning into the fosmid vector pEpiFOS-5 about 50000 colonies were obtained per µg of soil DNA. Our final library was constructed from a single ligation mixture and contained 25278 clones arrayed in 66 384-well microtitre plates. Restriction analysis of 30 randomly chosen clones with NotI showed insert sizes between 32.5 and 43.5 kbp, with an average of 36.5 kbp which corresponds well with the insert size range acceptable for this type of vector (FIG. 6). The total library therefore contained an estimated 0.9 Gbp of environmental genomic soil DNA, which represents 225 genome equivalents assuming a 4 Mbp average genome size. Most inserts analyzed exhibited complex patterns after NotI digestion, suggesting that these clones contained DNA with high GC content.

Example 3

Screening of the Library

The arrayed clones of the library were plated a) onto LB-agar to grow the cells for a subsequent preparation of fosmid-pools as a resource for sequence-based screenings (using PCR and degenerate primers to generate metagenome sequence tags e.g. as probes for hybridisation) and b) onto LB-agar containing specific substrates for the detection of enzymatically active colonies e.g. through scoring of clearing zones around the colonies (FIG. 7) and c) onto LB-agar for growth and subsequent overlay with a lawn of indicator organisms to score for recombinants producing antibiotics.

Example 4

Purification of Soil Metagenomic DNA by use of a 2-Phase Gel-Permeation/Affinity Column Metagenome DNA from soil was extracted by gentle chemical lysis as described before (Zhou et al., (1996) lod. cit.). Crude DNA extract was passed over a 2-phase column by gravity-flow using a borosilicate glass column (BIORAD #737-0717). The column (7×150 mm) was packed with a lower phase of 1 ml PVPP (SIGMA #P-6755) and an upper layer of Sepharose 2B (SIGMA #2B-300) to a final volume of 5 ml. After equilibrating the column with 20 ml of running buffer (100 mM NaCl, 10 mM Tris, 1 mM EDTA; pH 8.0) separation of DNA from humic and fulvic acids was initiated by applying crude DNA extract (ideally 1-5% resin volume) to the top of the column. Eluting fractions of 300 μl were collected dropwise (6 drops) and subsequently analysed. Relative DNA content was quantified by comparing the fluorescence of DNA bands in each fraction after electrophoresis on a 1% agarose gel containing ethidium bromide (FIG. 8) and documentation using a CCD camera system (GeneGenius) and GeneTools software package (both Syngene, UK). The spectral absorption of fractions at 230 nm and 260 nm was measured spectrophotometrically. Fractions 8 and 9 contain pure clonable DNA. Analysis of later eluting fractions 10-12 show humic acid contamination as can be seen in the decrease in the ratio OD260/OD230. This is due to the significant rise of the OD230 values—the maximum absorption for humic acids. As humic substances also absorb at longer wavelengths the OD260 values increase similarly. The separation of fractions containing pure DNA and fractions containing humic substances can be improved further by adjusting the ratio of the loaded volume of crude DNA extract to the resin volume of the column in a way known to those skilled in the art and by adjusting the DNA content of the loaded samples.

Example 5

Exemplified Identification of Genes of a Microorganism as Part of a Metagenome in Accordance with the Invention Traditionally, soil microbiology has focused on the description of cultivable microorganisms, while functional aspects of soil microbial communities have mainly been restricted to bulk studies that involved the monitoring of substrates and levels of end products. The application of molecular techniques to microbial ecology revealed that many of the microbial transformations in the environments might be performed by organisms that have not yet been cultivated and thus far remained uncharacterized (Pace (1997) *Science* 276, 734-740, Hugenholtz et. al. (1998) *J. Bacteriol.* 180:4765-74). Soil was confirmed to be particularly rich in microbial diversity based on phylogenetic studies with 16S rRNA genes directly amplified from environmental samples (see e.g. Hugenholtz et. al. (1998) loc. cit., Borneman et al. (1996) *Appl. Environm. Microbiol.* 62, 1935-1943, Barns et. al. (1999) *Appl. Environm. Microbiol.* 65, 1731-1737, Dunbar et. al. (1999) *Appl. Environm. Microbiol.* 65, 1662-1669). Frequently, evidence was even found for the existence of microorganisms from divisions that were not previously associated with soil habitats and of which no cultivated relatives. Among one of the most striking discoveries was the frequent detection of non-thermophilic members of the archaeal kingdom Crenarchaeota (DeLong (1998) *Curr. Opin. Genet. Dev.* 8, 649-654). 16S rDNA sequences of these archaea were first identified in marine picoplancton (DeLong (1992) *Proc. Natl. Acad. Sci. USA* 89, 5685-9, Fuhrman et. al. (1992) *Nature* 356, 148-9) and then found in freshwater habitats (Hershberger et. al. (1996) *Nature* 384, 420, Schleper et. al. (1997a) *Appl. Env. Microbiol.* 63, 321-323, McGregor et. al. (1997) *Appl. Env. Microbiol.* 63, 1178-1181, Jurgens et. al. (2000) *FEMS Microbiol. Ecol.* 34, 45-56) and in soils from various locations in the United States (Bintrim, et. al. (1997) *Proc. Natl. Acad. Sci. USA* 94, 277-282, Buckley et. al. (1998) *Appl. Environ. Microbiol.* 64, 4333-4339), Finland (Jurgens et. al. (1997) *Appl. Environ. Microbiol.* 63, 803-805), Japan (Ueda et. al. (1995) *Eur. J. Soil Sci.* 46, 415-421, Kudo et. al. (1997) *Biosci. Biotechnol. Biochem.* 61, 917-20) and Germany (Sandaa, et. al. (1999) *Appl. Environ. Microbiol.* 65, 3293-3297, Ochsenreiter et. al., in preparation). The ubiquitous ecological distribution of crenarchaeota was very surprising, because their cultivated relatives are exclusively (hyper)thermophiles isolated from terrestrial and marine hot springs.

Quantitative estimates have demonstrated the significant occurrence of non-thermophilic crenarchaeota in marine habitats (Massana et. al. (1997) *Appl. Environ. Microbiol.* 63, 50-6, Karner et. al. (2001) *Nature* 409, 507-510), in freshwater sediments (McGregor et. al. (1997) loc. cit.) and in soil (14, 19). Some crenarchaeotal lineages were shown to be specifically associated with plant roots, indicating that the organisms might play a role in the ecology of the rhizosphere (Simon et. al. (2000) *Environ. Microbiol.* 2, 495-505, Chelius & Triplett (2001) *Microb. Ecol.* 41, 252-263). While 16S rRNA studies have provided insights into the huge extent of microbial diversity novel approaches are being sought to be able to functionally characterize those microorganisms that have escaped classical cultivation approaches.

Inspired by the rapid advances in microbial genomics of cultivated organisms, a novel approach has recently been initiated to characterize uncultivated organisms that have solely been predicted in rRNA gene surveys. It involves the construction of complex habitat-specific gene libraries by direct cloning of genomic fragments from environmental samples into cloning vectors (DeLong (2001) *Curr. Opin. Microbiol.* 4, 290-295). With the help of phylogenetically relevant gene markers, such as e.g. rDNA genes, large genomic fragments of specific phylotypes can be isolated from these libraries. Yet at present the full potential of this approach cannot be realized as technical constraints severely hamper the cloning of large DNA inserts, particularly from microbial consortia of inhibitor-rich environments like soils or sediments. The approach has successfully been applied to characterize uncultivated, marine microorganisms: Several genome fragments of the symbiotic crenarchaeote *Cenarchaeum symbiosum* and of marine archaea representing abundant components of the picoplancton in North Pacific and Antarctic waters were retrieved from BAC and fosmid libraries (Stein et. al. (1996) *J. Bacteriol.* 178, 591-599, Schleper et. al. (1998) *J. Bacteriol.* 180, 5003-5009, Béjà et. al. (2000a) *Environ. Microbiol.* 2, 516-529, Beja et. al. (2002a) *Nature* 415:630-633, Béjà et. al. (2002b) *Appl. Environ. Microbiol.* 68, 33545). A comparison of crenarchaeotal fosmids revealed significant genomic divergence even in clones with identical 16S rRNA sequences (Béjà et. al. (2002b) loc. cit.). The diversity of large photosynthetic gene clusters of proteobacteria was analyzed from marine planctonic genomic samples (Beja et. al. (2002a) loc. cit.). A novel type of rhodopsin, termed proteorhodopsin that functions as a light-driven proton pump was discovered in the genomic fragment of an uncultivated marine γ-proteobacterium (Béjà et. al. (2000b) *Science* 289, 1902-1906). The analyses of large genomic regions of hitherto uncultivated organisms also provided the basis for functional studies, including the monitoring of protein activities in the environment (Beja et. al. (2002a) loc. cit., Beja, et. al. (2001) *Nature* 411, 786-9) and the characterization of proteins after expression in the surrogate host *E. coli* (Béjà et. al. (2000b) loc. cit., Schleper et. al. (1997b) *J. Bacteriol.* 179, 7803-7811). The colocalization of functional, metabolic genes with phylogenetically ascribable genetic markers like rRNA genes provides insights into the physiological potential of uncultivated microorganisms. Clearly the likelihood of a physical colocalization of such markers on a contiguous cloned DNA stretch will be directly linked to DNA fragment size. This highlights the relevance of cloning large uninterrupted DNA fragments which is technically very difficult to achieve particularly from microbial consortia of inhibitor-rich environments like soils or sediments. We have developed procedures for the efficient purification of large DNA fragments by eliminating the polyphenolic compounds that heavily contaminate soil DNA. We have constructed complex genomic libraries and used these to isolate fragments from non-thermophilic crenarchaeota. While direct cloning of large DNA from soil samples has been demonstrated earlier (Rondon et. al. (2000) *Appl. Environ. Microbiol.* 66, 2541-2547), our study represents the first genomic characterization of a lineage of soil microorganisms that has solely been predicted by PCR-based studies.

5.1 Experimental Procedures

Preparation of DNA from Soil

Soil was collected from the upper layer (0 to 5 cm) of a partially ruderalized sandy ecosystem ("Am Rotböll") near Darmstadt (Germany) in early Spring 2001. DNA was prepared as described in Example 1.1, supra. About 50 g were suspended in 300 ml of buffer (20 mM Tris pH 8, 10 mM ϵ-aminocaproic acid, 10 mM EDTA) and incubated at 4° C. for 15 h with gentle shaking. The sample was filtered to remove larger particles, and the microbial fraction was centrifuged and embedded into agarose plugs (0.5% low-melting SEAPlaque, FMC Bioproducts). These plugs were incubated at 37° C. for 1 hour in 100 mM EDTA, 10 mM Tris-HCl pH 8, 50 mM NaCl, 0.2% deoxycholate, 1% lauroyl sarcosine, 1 mg/ml lysozyme, then transfered into ESP buffer (2 mg/ml proteinase K, 1% lauroyl sarcosine, 0.5 M EDTA) and incubated at 50° C. for 24 h with gentle rotation and with one exchange of buffer. Agarose plugs were placed in a 1% agarose gel (Sigma A-2929) which contained 2% polyvinylpyrrolidone (VP-360, Sigma) in the first half and no PVP in the second half. Pulse field gel electrophoresis was performed at 10° C., 6 V cm-1 for 20 h with 1 to 4 sec pulses in a CHEF-DR II (BioRad). DNA of >30 kb was extracted from the gel and submitted to a second size selection using a regular agarose gel. After electroelution the resulting DNA was dialyzed and concentrated in a microconcentrator.

Library Construction

Purified DNA (0.5 μg) was enzymatically treated to prepare 5' phosphorylated blunt ends and was ligated into fosmid vector pEpiFOS-5 (pEpiFOS™, Epicentre). After in vitro packaging into lambda phages, the infected cells were plated on $LB^+$ medium (containing 12.5 μg/ml chloramphenicol). The colonies were transferred to 384-well microtitre plates containing 50 μl of $LB^+$ medium and 7% glycerol (v/v). The plates were incubated at 37° C. for 24 hours.

16S rDNA Diversitystudies

Primers specific for the domain Archaea (20F/958R, DeLong (1992) *Proc Natl Acad Sci USA* 89: 5685-9) and Bacteria (27F/1391R, Reysenbach and Pace (1995) Archaea: a laboratory manual (Cold spring Harbor Laboratory Press)) were used to amplify 16S rDNA fragments from the DNA used for constructing the large-insert library. The fragments were subsequently cloned into pGEM-T-easy (Promega) and sequenced. The ARB-software package (Ludwig et al. (1998) Electrophoresis 19: 554-568.) was used for alignments and phylogenetic analyses of the partial 16S rDNA genes.

Screening and Sequence Analysis of Fosmid Clone 29i4

Plasmid DNA from the library was prepared from pools of 384 clones and screened by PCR with archaea-specific 16S rDNA primers (DeLong (1992) loc. cit.). A product of correct size (950 bp) was obtained from pool 29. It was randomly labelled with digoxyenin (Roche Biochemicals) and used as a probe in colony hybridization to identify the individual clone (i4). A subclone library was prepared from the fosmid DNA by mechanical shearing and cloning of 2-3 kbp fragments into pGEM-T-easy (Promega). The ends of the cloned DNA fragments were sequenced with vector primers using ABI3700 capillary sequencers. Remaining sequence gaps were closed by primer walking with sequence-derived oligonucleotides.

Sequence Annotation

The ORF identification and automatic gene annotation were done with the help of the MAGPIE program package (Gaasterland and Sensen (1996) *Biochimie* 78: 302-310). The Wisconsin Package (Heidelberg Unix Sequence Analysis Server, HUSAR) was used for additional searches with GCG-BLAST, identification of PFAM domains and transmembrane segments, for secondary structure prediction and peptide motifs. A tRNA gene was identified using the tRNA scan server (http://www.genetics.wustl.edu/eddy/tRNAscan-SE/). Multiple alignments were done with PILEUP and CLUSTAL and manually corrected in SEQLAB. The sequence was deposited in EMBL under the accession no. AJ496176.

Phylogenetic Analyses

The ARB-software package (Ludwig et al. (1998) loc. cit.) was used for alignments and phylogenetic analyses of full-length 16S and 23S rDNA genes from Archaea and from the marine environmental clones of a euryarchaeote 37F11 (Béjà et al. (2000a) loc. cit.), and of two crenarchaeota (4B7, Stein et al. (1996) loc. cit., Béjà et. al. (2002b) loc. cit.). The topologies of the 23S rDNA tree were evaluated using the maximum parsimony (parsimony interactive) and the distance matrix (Felsenstein correction) method with different alignment filters (gap-filter, positional variability filter, maximum frequency filter). The topologies of the corresponding 16S rDNA tree were evaluated using the same methods and in addition the maximum likelihood (fastDNAml) method with different alignment filters as described above. Phylogenetic analysis of the putative FixA gene (ORF12/SEQ ID NO: 24) was performed using the protein parsimony (PROTPARS) and neighbor-joining (NEIGHBOR) programs from PHYLIP version 3.6 and PAUP version 3.1.1. The same overall topology was found with both methods based on 211 conserved positions from a sequence alignment of 33 FixA/ETFβ (flavoprotein containing electron transport chain) homologs.

5.2 Results

Construction of a Fosmid Library from Soil DNA

For preparation of high molecular weight DNA biomass from a soil sample was embedded into agarose plugs prior to lysis. The resulting DNA appeared heavily contaminated with polyphenolic compounds (i.e. humic and fulvic acids) as indicated by a dark brownish appearance. In the process of optimizing the subsequent purification steps, a pulse field electrophoresis procedure was developed that involved an agarose gel with two phases. It allowed purification of the DNA from soil substances through a PVP (polyvinylpyrrolidone) containing phase. In a second phase the PVP was subsequently eliminated, while a first size selection of the DNA was achieved. Highly concentrated, pure and clonable DNA in the size range of 30 to 100 kb was recovered in this one-step electrophoresis procedure, thereby minimizing shearing effects that tend to occur in repeated electrophoresis procedures. The approach has been successfully applied to different soil samples, like ruderal, agricultural and forest soils, for rapid preparation of pure and concentrated high molecular weight DNA (data not shown). After blunt-end cloning into the fosmid vector about 50,000 colonies were obtained per μg of soil DNA. Our final library contained 25,278 clones.

Figure 10:
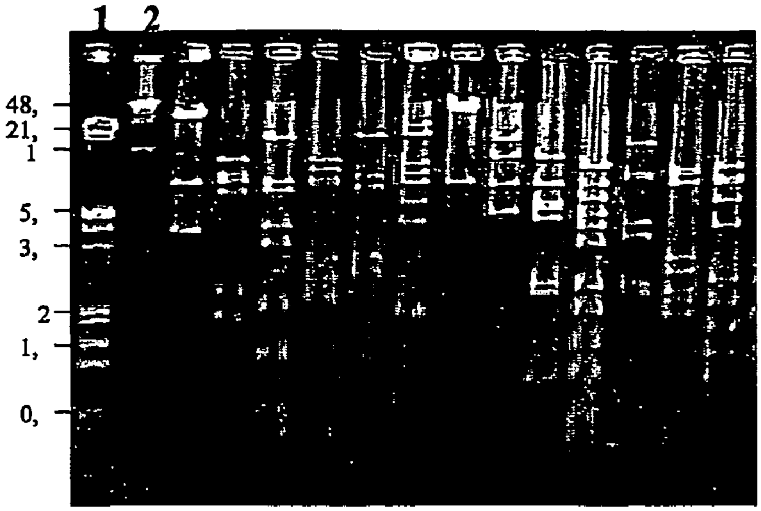

Restriction analysis of 30 randomly chosen clones using NotI showed insert sizes between 32.5 and 43.5 kb. The library therefore contained approximately 0.9 Gbp of environmental genomic soil DNA. 27 of 30 inserts analyzed exhibited complex patterns after NotI digestion, suggesting that these clones contained DNA with high G+C content (NotI recognition sequence: GCGGCCGC; FIG. 10).

Sequencing of insert ends from 2688 clones revealed in about 25% of the sequences significant similarities to protein genes from the data bases (e-values of $<10^{-10}$ in blastx searches). Among these were homologs of proteins from lineages that are typically found in soils, i.e. streptomycetes, clostridia and bacilli (data not shown). However most of the sequences did not show significant similarities to known protein genes. Together, these results confirmed that a great diversity of genomic DNAs was contained in the library.

To further monitor the diversity of the DNA used for construction of the library, a PCR-based 16S rDNA survey was performed using a primer set specific for Bacteria. 16S rRNA gene fragments affiliated with eight different bacterial phyla were identified in a random sample of 50 different sequences, many of which are typical for soil microbial assemblages, i.e. Actinobacteria, Chloroflexi, α,β,ϵ Proteobacteria, Planctomycetes, Acidobacterium/Holophaga, Cytophaga.

Identification and Analysis of a Genomic Clone from Non-Thermophilic Crenarchaeota in Soil.

Using a multiplex PCR approach and 16S rDNA-specific probes, an archaeal fosmid clone was identified in the library. The insert of clone 29i4/SEQ ID NO: 1 was entirely sequenced and comprised 33,925 bp with an average G+C content of 40%. It encoded a complete 16S and 23S ribosomal RNA operon, one tRNA gene and 17 predicted protein-encoding genes. The 16S RNA gene was 97% identical over 711 positions (*E. coli* positions 8-719) to sequences previously recovered in a PCR study from the same soil (Ochsenreiter and Schleper, manuscript in preparation) and 95-97% identical to sequences obtained from a soil in Wisconsin (Bintrim et al. (1997) loc. cit.). The ribosomal RNA operon of clone 29i4 consisted only of the 16S and 23S rRNA genes, without linked 5S rRNA or tRNA genes similar to cultivated thermophilic and uncultivated marine crenarchaeota. Phylogenetic analyses with the complete 16S rRNA and 23S rRNA genes confirmed the affiliation of clone 29i4 with the crenarchaeota (FIG. 11). As predicted by phylogenetic analyses with partial 16S rRNA sequences, it formed a sister group to the uncultivated marine organisms. The phylogenetic tree in FIG. 11 is based on complete 23S rRNA genes from known archaeal genomes and from environmental genomic fragments of marine archaea. The same branching orders were found in 16S rRNA phylogenies (see legend to FIG. 11).

Ten of the 17 predicted protein-encoding genes showed significant similarity to genes of known function, two were conserved hypothetical genes, five open reading frames did not show any similarity to sequences in the databases (February 2002). Eight of the predicted proteins showed highest similarities to archaeal homologs (Table 1 and FIG. 12). A family B DNA polymerase shared 46% identical positions with its closest homolog from *Cenarchaeum symbiosum* (Schleper et al. (1997) J. Bacteriol. 179, 7803-11). Although the C-terminal end of about 90 amino acids was not encoded on fosmid 29i4, all conserved exonuclease and polymerase motifs typically found in this class of DNA polymerases were identified in the deduced amino acid sequence.

Two other predicted proteins belonging to conserved archaeal protein families were an asparagine synthetase and a phosphoserine phosphatase, both involved in amino acid metabolism. Two putative glycosyl transferases (ORF07/SEQ ID NO.: 14 and 10/SEQ ID NO.: 20) shared significant similarities with homologs from the crenarchaeote *Sulfolobus solfataricus* and from the euryarchaeote *Pyrococcus* ssp., repectvely. In contrast, a putative polyhydroxyalkanoate synthase (ORF04/SEQ ID NO.: 8) and a second α/β-hydrolase (ORF02/SEQ ID NO.: 4) were most closely related to bacterial proteins.

A gene cluster was identified with high similarity in structure and sequence to the fixABCX operons found in many symbiotic nitrogen-fixing soil bacteria. Based on its similarity to the components of the flavoprotein-containing electron transport chain (ETF) that is involved in β-oxidation of fatty acids in mitochondria and some bacteria, the operon was proposed to encode a flavoprotein-containing electron transport chain (Weidenhaupt et al. (1996) *Arch Microbiol* 165: 169-178). In symbiotic bacteria the operon is co-regulated with other genes involved in nitrogen fixation (Gubler and Hennecke (1998) *J Bacteriol* 170: 1205-1214). FixABCX genes have also been identified in the genomes of several other bacteria and some thermophilic and hyperthermophilic archaea, i.e. in *Sulfolobus solfataricus, Thermoplasma acidophilum, Pyrobaculum aerophilum* and *Aeropyrum pernix*. Phylogenetic analyses of the putative FixA gene from 29i4 and homologs from completely sequenced microbial genomes indicated a close affiliation of FixA from 29i4 with other archaeal proteins. Together with FixA proteins from nitrogen fixing bacteria they formed a distinct subgroup within the Etfβ/FixA superfamily (FIG. 13).

A sensory histidine kinase was identified in close proximity but oriented in opposite direction to the fixABCX operon on clone 29i4. While the C-terminal half of the protein exhibited the conserved motifs typically found in sensory histidine kinases, no similarities to known proteins that might give hints to its specific role in sensing were found in the 350 amino-acid long N-terminal part.

Using PCR primers targeting the ends of the insert of clone 29i4 and internal protein coding genes, no contiguous genomic fragments overlapping clone 29i4 could thus far be detected in the library. However, additional archaeal clones were identified from non-thermophilic crenarchaeota in a second library that contained another 1.5 Gbp of DNA from the same soil sample. One of these clones was identified with archaea-specific 16S rRNA probes (as used for clone 29i4) and two other clones were identified through sequencing of insert ends from 768 randomly chosen clones. The sequence analysis of these genomic fragments is under way.

5.2 Discussion

The direct cloning of high-molecular weight DNA from soil is particularly difficult due to the occurrence of polyphenolic compounds that co-purify with DNA and severely inhibit PCR amplification reactions, hydrolysis by restriction enzymes, ligation and cloning procedures (Trevors and Van Elsas (1995) *Nucleic Acids in the Environment: Methods and Applications*, Springer Verlag, Berlin; Young et al. (1993) loc. cit.). Therefore, any purification protocol for DNA from soil samples must remove the phenolic compounds. Protocols have been developed that involve the addition of hexadecylmethylammoniumbromide (CTAB, Zhou et al. (1996) loc. cit.) or polyvinylpyrrolidone (PVP, Trevors and Van Elsas (1995) loc. cit.) in the extraction buffers, because these compounds complex polyphenolics or reduce their electrophoretic mobility when included in electrophoresis procedures (Young et al. (1993) loc. cit.). However, such compounds in turn have to be efficiently eliminated (e.g. by extraction, electrophoresis or affinity chromatography) because they inhibit enzymatic treatments of the isolated nucleic acids. Due to these difficulties most purification procedures either result in high quality DNA suitable for PCR amplification of gene fragments but too highly degraded for cloning of large fragments or it results in high molecular weight DNA that is not pure enough for cloning procedures. (refs above and own observations). Therefore, the device of the invention was developed for the electrophoresis procedure described herein above (two phases in which the DNA is first purified from polyphenolics in a PVP containing phase and subsequently cleaned in a second phase, thereby minimizing shearing effects that occur in repeated electrophoresis procedures). This technique allows reproducible obtainment of highly concentrated and pure, high molecular weight DNA. While purification techniques similar to those described by Zhou et al. (1996) loc. cit.) that was used by Rondon et al. (2000) loc. cit.) for cloning large DNA fragments were not applicable to many of our samples, the novel PVP electrophoresis procedure yielded reliable results with different soil samples of varying organic and humic acid content. Successful purification of the DNA was independent of the lysis procedures that we used, i.e. direct lysis of soil samples as in Zhou et al. (1996) loc. cit.) or lysis of microbial fractions as described here.

The complex environmental libraries constructed exemplarily by using the device and method of the invention contain a large fraction of the total genomic content of a soil microbial population, which has been referred to as the soil "metagenome" (Rondon et al. (2000) loc. cit.). The library characterized here was constructed in a BAC-derived fosmid containing cos-sites for in vitro packaging with lambda phages. Said vector yielded significantly larger clone numbers than using classical BAC-vectors (data not shown) and it allowed the direct cloning of undigested DNA by blunt-end ligation, thereby avoiding any bias introduced by restriction digests. Using 50 g of soil, a library with 0.9 Gbp of environmental DNA was constructed which represents approximately 225 genome equivalents assuming a 4 Mbp average genome size. Using archaea-specific 16S rDNA probes the fosmid clone 29i4 was identified. Sequence analysis demonstrated that a contiguous genomic fragment of non-thermophilic soil crenarchaeota was isolated: (i) Phylogenetic analyses based on the complete ribosomal 16S and 23S RNA genes indicated the specific affiliation with the crenarchaeotal clade as predicted in PCR-based studies. (ii) genes affiliated with archaea were found dispersed over the entire clone insert (iii) G+C content and codon usage of the predicted protein genes were similar over the entire insert and (iv) the deduced aminoacid sequence of a DNA polymerase gene showed greatest similarity to its homolog from the uncultivated marine symbiont *Cenarchaeum symbiosum*. Functional and biochemical analysis of the latter protein had confirmed the predicted non-thermophilic phenotype of this crenarchaeote (Schleper et al. 1997) J Bacteriol. 179, 7803-11).

On the other hand, significant differences to the content and structure of genomic fragments from uncultivated nonthermophilic marine archaea revealed that crenarchaeota from soil have significantly diverged from their relatives in other environments. An unusually large gap in the 16S-23S RNA operon and the lack of a GSAT gene (glutamate semialdehyde aminotransferase), which was consistently found to be directly linked to the ribosomal operon on all marine crenarchaeotal genome fragments (Béjà et al. (2002) loc. cit.) indicates the difference. Direct comparison of the soil fosmid clone to the genomic clones obtained from marine planctonic crenarchaeota and from the symbiont *C. symbiosum* revealed only one related protein encoding gene, i.e. the putative DNA polymerase. Genes on clone 29i4/SEQ ID NO: 1 appeared to be less densely packed than in genomes of other archaea. Only 69% of the sequence encoded RNA or protein genes. There was the large intergenic region in the 16S/23S rRNA cluster of 830 bp, which is atypical for ribosomal operons in crenarchaeota. Another large non-coding region of 2787 bp was found between ORF10/SEQ ID NO: 20 and fixA. No apparent genes or distinctive structural features, e.g. repetitive elemens were identified in the non-coding regions.

The genomic information contained on fosmid 29i4/SEQ ID NO: 1 gives first insights into metabolic properties of crenarchaeota from soil and can serve as a basis for functional genomic studies. Beside genes encoding proteins for "housekeeping" functions (replication, aminoacid metabolism), two a/β type hydrolases so far seem to be particularly found in soil crenarchaeota. One of them encodes a putative protein involved in the synthesis of polyhydroxyalcanoates. The operon encoding FixABCX revealed a putative flavoprotein containing electron transport chain that is commonly found in symbiotic nitrogen-fixing bacteria. A detailed phylogenetic analysis indicated that the putative FixA protein of 29i4 is most closely affiliated with archaeal FixA homologs and not with the FixA proteins of Bacteria or the paralogous ETF proteins from other species of Archaea, Eucarya or Bacteria. Therefore, it seems unlikely that the fixABCX genes of 29i4 have been acquired by horizontal gene transfer e.g. from symbiotic nitrogen-fixing bacteria which might reside in the same soil habitat. They rather seem to originate from a common ancestor of the Archaea. None of the obligately aerobic archaea that contain the fixABCX genes is known to be capable of fixing nitrogen. Expression analysis of this operon in well-studied thermophilic model organisms, such as *Sulfolobus solfataricus* might shed light on its physiological role in crenarchaeota.

Example 6

Separation of DNA Extracts on a PVPP/Sepharose 2B Column

Metagenome DNA from soil was extracted by gentle chemical lysis. Crude DNA extract was separated by gravity-flow gel filtration using a borosilicate glass column (BIO-RAD #737-0717). The column (7×150 mm) was packed with ⅙ volume PVPP (SIGMA # P-6755) and an upper layer of Sepharose 2B (SIGMA # 2B-300) to a final volume of 5 ml. Equilibration and removal of storage buffer was done by passing 5 reservoir volumes of TEN buffer (100 mM NaCl, 10 mM Tris, 1 mM EDTA; pH 8.0) by gravity flow. Separation of DNA and humic acids was initiated by applying crude DNA extract (ideally 1-5% resin volume) to the column. Approximately 300 μl fractions were collected dropwise (6 drops per fraction) and subsequently analysed. Relative DNA contents was quantified by fluorescence intensity comparison of DNA bands of each fraction on 1% agarose. Absorption at 230 nm and 260 nm was measured spectrophotometrically. Fractions 7-10 represent pure DNA. Analysis of later fractions 11-22 show humic acid content with a maximum in fraction 16. As humic substances also absorb at longer wavelengths the OD260 values increase in a similar extent as those of OD230 which could mislead to assume high DNA concentrations. The specialist is able to discriminate pure DNA fractions from those contaminated by humic acids by increasing absorption at 230 nm and a low ratio OD260/OD230.

Example 7

Validation of the Purifying Effect of the 2-Phase Gel on High Molecular Weight Soil DNA Pellets of uncultivated bacteria isolated from soil were embedded in agarose plugs and treated appropriately to liberate their genomic DNA in situ. The DNA plugs were embedded either in an ordinary preparative PFGE (pulsed field gel electrophoresis) gel (FIG. 14 A) or a 2-phase PFGE gel (FIG. 14 C) for sizing and eventual purification. After completion of the PFGE, agarose plugs containing high molecular weight DNA in the compression zones were cut out and subjected to digestion with the restriction endonuclease Hind III to create DNA ends compatible with common cloning sites in suitable DNA vectors. After terminating the digestion the DNA plugs were inserted into analytical PFGE gels to analyse the success of the digestion.

As seen in FIG. 14 B soil DNA separated in a conventional agarose PFGE gel was highly resistant to digestion even with large amounts of restriction enzyme whereas high molecular weight DNA purified in the 2-phase PFGE gel was readily fragmented with very little restriction enzyme (FIG. 14D) proving its high degree of purity and consequently clonability. Cloning DNA fragments with compatible ends into suitably prepared DNA vectors like BAC, Plasmid, Lambda, Fosmid, Cosmid, YAC and PAC are standard procedures known to those skilled in the art.

TABLE 1

Predicted RNA and protein encoding genes in the archaeal fosmid 29i4.

| ORF | Nt range | protein size | putative function | most similar ortholog* | Phyl. aff.# | Comments |
|---|---|---|---|---|---|---|
| 01 | 1-2367 | 789 aa (C-termi. truncated) | Family B DNA polymerase pfam00136 | AAC62689 *Cenarchaeum symbiosum* (0.0) | AEB | |
| RNA | 3548-5018 | | 16S RNA | 85% identity to 16S RNA of *Cenarchaeum symbiosum* | | |
| RNA | 5847-8818 | | 23S RNA | 77% identity to 23S RNA of *Cenarchaeum symbiosum* | | |
| 02 | 8968-9849 | 293 aa | α/β hydrolase pfam00561 | AAD02150 *Pseudomonas stutzeri* (e-17) | AEB | Catalytic triade Ser/Asp/His; close homologs are from bacteria |
| 03 | 9888-10205 | 105 aa | Hypothetical | none | | |
| 04 | 10219-11304 | 361 aa | PHA Synthase (α/β hydrolase, pfam00561) | P45366 *Thiocystis violacea* (e-66) | B | No homolog in archaea but PHB production has been described in Halobacteriaceae |
| 05 | 11285-11866 | 193 aa | Hypothetical | none | | |
| RNA | 12414-12502 | | $tRNA^{Arg}$ | | | |
| 06 | 13017-13454 | 145 aa | Hypothetical | none | | |
| 07 | 14324-15238 | 304 aa | Glycosyl transferases group 1, pfam00534 | AAK41834 *Sulfolobus solfataricus* (e-11) | AEB | Transfer of ADP, UDP, GDP, CMP linked sugars |
| 08 | 15716-17407 | 563 aa | Asparagine synthetase pfam 00310 | AAB99117 *Methanococcus janaschii* (e-67) | AEB | |
| 09 | 17492-18157 | 221 aa | Phosphoserin phosphatase pfam00702 | AAB86099 *Methanothermobacter thermautotrophicus* (e-14) | AEB | |
| 10 | 18377-19588 | 403 aa | Conserved hypothetical | CAB50138 *Pyrococcus abyssi* (e-91) | A | Homologs only found in *P. abyssi, P. horikoschii, A. pernix*, Glycosyltransferase group 2 domain; pfam 00535 |
| 11 | 20630-21793 | 387 aa | Transmembrane protein | BAB50489 *Mesorhizobium loti* (e-31) | B | Domain pfam 01173 |
| 12 | 24580-25461 | 293 aa | Fix A pfam01012 | P53576 *Azotobacter vinelandii* (e-23) | AB | Paralogs of ETFβ: electron transfer flavoprotein β subunit |
| 13 | 25458-26741 | 427 aa | Fix B pfam00766 | P53578 *Clostridium saccharobutylicum* (e-45) | AB | Paralogs of ETFα: electron transfer flavoprotein α subunit |
| 14 | 26738-28615 | 625 aa | Fix CX | NP_454687 *Salmonella enterica* (e-36) FixX: *Thermoplasma volcanium* (e-08) | AB | Fused protein of FixC and FixX |
| 15 | 29228-31465 | 745 aa | Sensory transduction histidine kinase, pfam00512 | BAB73503 *Nostoc* sp. PCC 7120 (e-12) | AEB | |
| 16 | 32505-33023 | 172 aa | Hypothetical protein | none | | |
| 17 | 32918-33925 | 335 aa (truncated) | hypothetical | none | | |

*proteins are designated by their gene identification numbers followed by the species name. The e-values of blastx searches are added in brackets.
#Phyl. aff. = Phylogenetic affinity, denotes occurrence of homologs in Archaea (A), Bacteria (B) or Eucarya (E).

The invention claimed is:

1. A device for the isolation and/or purification of nucleic acid molecules comprising at least two layers, a first layer being adapted to bind or inactivate inhibitors of the activity of reagents or enzymes used in nucleic acid manipulation, wherein said first layer comprises polyvinylpyrrolidone (PVP) or polyvinylpolypyrrolidone (PVPP), and wherein said first layer further comprises a sample loading means in an array in an upper portion of the first layer, defining an array of columns, each column being capable of isolating nucleic acid molecules, and a second layer being adapted to separate a plurality of nucleic acid molecules with respect to their size, and wherein said first layer is a first phase of a gel and said second layer is a second phase of said gel, wherein said first layer is arranged above the second layer, and wherein said second layer is substantially free of PVP when said first layer comprises PVP, and wherein said second layer is substantially free of PVPP when said first layer comprises PVPP.

2. The device of claim 1, wherein said gel is an agarose gel or a polyacrylamide gel.

3. The device of claim 1, wherein said first layer further comprises CTAB, EDTA, EGTA, cyclodextrins, proteins, (poly)peptides, antibodies, aptamers, lectins, nucleic acids or an ion-exchanger.

4. The device of claim 1, wherein said second layer is substantially free of CTAB, EDTA, EGTA, cyclodextrins, proteins, (poly)peptides, aptamers, antibodies, lectins, nucleic acids or an ion-exchanger.

5. The device of claim 1, wherein the device is electrically biased to enhance flow of at least one sample through the layers.

6. The device of claim 1, wherein said first or second layer further comprises agarose, dextran, an acrylamide based resin or acrylamide.

7. The device of claim 1, wherein said nucleic acid molecule is DNA or RNA.

8. The device of claim 7, wherein said DNA is genomic DNA.

9. The device of claim 7, wherein said nucleic acid molecules represent a fraction of the metagenome of a given habitat.

10. The device of claim 7, wherein said nucleic acid molecule is derived from (micro)organisms of soil, sediments, water or symbiotic/parasitic consortia.

11. The device of claim 10, wherein said (micro)organisms are (micro)organisms of aquatic plancton, microbial mats, clusters, sludge flocs, or biofilms.

12. The device of claim 10, wherein said (micro)organism are isolated as consortia of coexisting species.

13. A method for the isolation of a nucleic acid molecule comprising applying a sample to the device as defined in claim 1 and isolating a nucleic acid molecule.

* * * * *